US011994528B2

(12) United States Patent
Vlassov et al.

(10) Patent No.: US 11,994,528 B2
(45) Date of Patent: May 28, 2024

(54) SYSTEMS, METHODS, AND DEVICES FOR AUTOMATED NUCLEIC ACID AND PROTEIN ISOLATION

(71) Applicant: LIFE TECHNOLOGIES CORPORATION, Carlsbad, CA (US)

(72) Inventors: Alexandre Vlassov, Austin, TX (US); Timothy Barta, Austin, TX (US); Justin Inslee, Broomfield, CO (US); Ethan Gentert, Longmont, CO (US); Robert Smith, Louisville, CO (US); Sara Thiele, Lafayette, CO (US); Carolyn Adams, Boulder, CO (US); Kraig Kruger, Boulder, CO (US); Robert Schneider, Erie, CO (US); Wade Lukianow, Boulder, CO (US); Jay Greco, Arvada, CO (US); Jason Jones, Erie, CO (US); David Cerrone, Broomfield, CO (US); Sumonto Ghosh, Longmont, CO (US); Brian Vajda, Boulder, CO (US); Andrew Basta, Erie, CO (US); Allan Evans, Golden, CO (US); Christopher Crowley, Golden, CO (US); Robert Setterquist, Austin, TX (US); Anne Cox, Golden, CO (US); Mark Mayernick, Lafayette, CO (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 430 days.

(21) Appl. No.: 17/122,324

(22) Filed: Dec. 15, 2020

(65) Prior Publication Data
US 2021/0190809 A1 Jun. 24, 2021

Related U.S. Application Data

(60) Provisional application No. 62/949,917, filed on Dec. 18, 2019.

(51) Int. Cl.
*G01N 35/10* (2006.01)
*B01D 61/58* (2006.01)
(Continued)

(52) U.S. Cl.
CPC ......... *G01N 35/1016* (2013.01); *B01D 61/58* (2013.01); *B01D 69/02* (2013.01);
(Continued)

(58) Field of Classification Search
CPC .. G01N 35/1016; G01N 1/405; G01N 1/4077; G01N 21/59; G01N 35/00584;
(Continued)

(56) References Cited

U.S. PATENT DOCUMENTS 10,820,847 B1 11/2020 Andeshmand et al.
2008/0153078 A1 6/2008 Braman et al.
(Continued)

FOREIGN PATENT DOCUMENTS

AU 2017235971 A1 10/2017
WO 2008/101196 A1 8/2008
(Continued)

OTHER PUBLICATIONS

International Preliminary Report on Patentability received for PCT Patent Application No. PCT/US2020/065055, mailed on Jun. 30, 2022, 18 pages.
(Continued)

*Primary Examiner* — Jill A Warden
*Assistant Examiner* — John McGuirk
(74) *Attorney, Agent, or Firm* — BakerHostetler

(57) ABSTRACT

Purifying target biomolecules, such as nucleic acids or proteins, from a biological source is a time intensive process and is typically performed by a skilled technician or scientist owing to the highly technical nature of the work. Systems, devices, and methods disclosed herein enable the automated
(Continued)

bioprocessing and purification of target biomolecules from a biological source. For example, an instrument and disposable cartridge are provided for automatedly isolating and purifying nucleic acids (such as plasmid DNA from a bacterial culture) or for isolating protein from any biological sample. Such an exemplary instrument and cartridge can work in concert to timely release, mix, and move the target biomolecule and various reagents and buffers through a target biomolecule purification process, resulting in a purified target biomolecule with less manual oversight than traditional approaches.

18 Claims, 41 Drawing Sheets

(51) Int. Cl.
*B01D 69/02* (2006.01)
*G01N 1/40* (2006.01)
*G01N 21/59* (2006.01)
*G01N 35/00* (2006.01)

(52) U.S. Cl.
CPC .......... *G01N 1/405* (2013.01); *G01N 1/4077* (2013.01); *G01N 21/59* (2013.01); *G01N 35/00584* (2013.01); *G01N 35/1081* (2013.01); *B01D 2311/2642* (2013.01); *B01D 2313/44* (2013.01); *B01D 2313/50* (2013.01); *B01D 2313/58* (2013.01); *B01D 2319/025* (2013.01); *B01D 2325/42* (2013.01); *G01N 2001/4088* (2013.01); *G01N 2035/1025* (2013.01); *G01N 2035/1053* (2013.01)

(58) Field of Classification Search
CPC ....... G01N 35/1081; G01N 2001/4088; G01N 2035/1025; G01N 2035/1053; G01N 35/00; G01N 2035/00316; G01N 2035/0436; G01N 2035/0491; G01N 35/1095; G01N 35/00029; G01N 2035/00475; B01D 61/58; B01D 69/02; B01D 2311/2642; B01D 2313/44; B01D 2313/50; B01D 2313/58; B01D 2319/025; B01D 2325/42; C12M 47/06; C12M 47/10; C12M 47/12; C12N 15/1003; C12N 15/1017; C07K 1/16; C07K 1/18; C07K 1/22; C07K 1/34; C07K 1/36; C12Q 1/6806

See application file for complete search history.

(56) References Cited

U.S. PATENT DOCUMENTS

| 2008/0213872 A1* | 9/2008 | Regan | G01N 35/08 422/255 |
| 2010/0120129 A1* | 5/2010 | Amshey | B01L 3/50273 435/270 |
| 2012/0168305 A1* | 7/2012 | Hunter | B01L 3/502715 422/68.1 |
| 2016/0305972 A1* | 10/2016 | Ogg | C12Q 1/686 |
| 2018/0021783 A1* | 1/2018 | Arlett | G01N 35/1002 435/287.2 |
| 2018/0280975 A1 | 10/2018 | Kilcoin et al. | |
| 2021/0047678 A1* | 2/2021 | Andeshmand | C12Q 1/689 |

FOREIGN PATENT DOCUMENTS

| WO | 2010/025302 A2 | 3/2010 |
| WO | 2011/094577 A2 | 8/2011 |
| WO | 2012/122458 A2 | 9/2012 |
| WO | 2015/073999 A1 | 5/2015 |
| WO | 2018/232167 A1 | 12/2018 |

OTHER PUBLICATIONS

International Search Report and Written Opinion received for PCT Patent Application No. PCT/US2020/065055, mailed on Mar. 23, 2021, 20 pages.
Londo, T., et al., "Accelerated recombinant protein purification process development—Automated, robotics-based integration of chromatographic purification and analysis", Journal of Chromatography A, Elsevier, Amsterdam, NL, vol. 798, No. 1-2, Mar. 6, 1998 (Mar. 6, 1998), pp. 73-82, XP004112342.

* cited by examiner

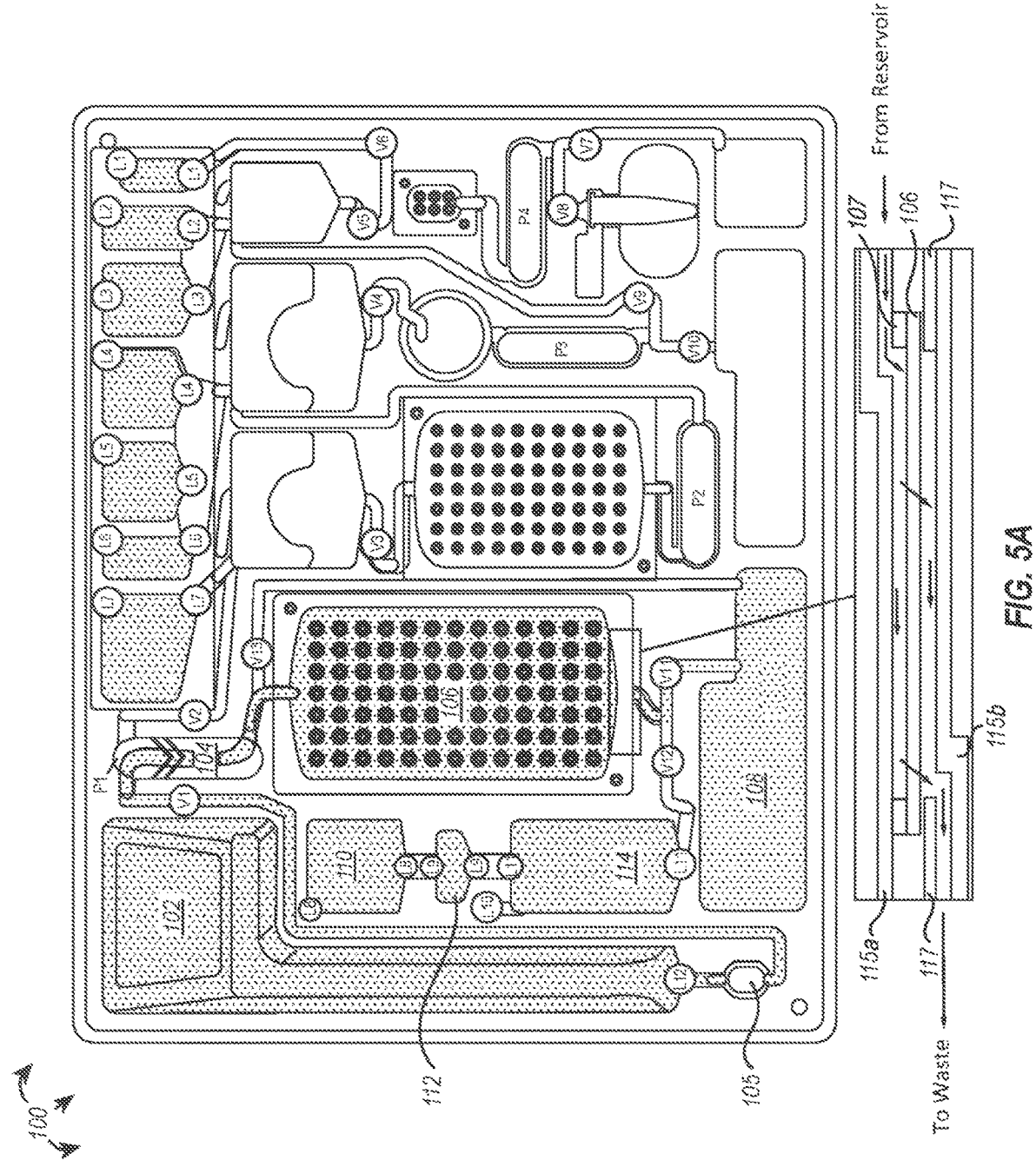

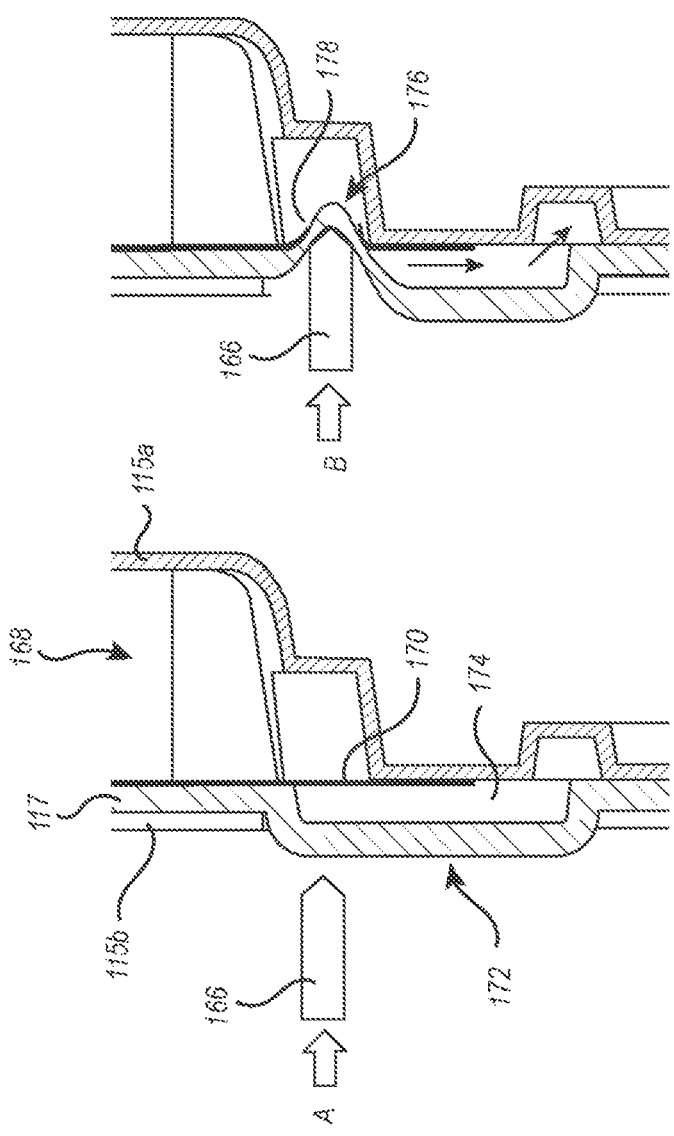

180 degrees (2nd revolution)

270 degrees (2nd revolution)

SYSTEMS, METHODS, AND DEVICES FOR AUTOMATED NUCLEIC ACID AND PROTEIN ISOLATION

CROSS-REFERENCE TO RELATED APPLICATIONS

This application claims benefit of U.S. Provisional Application No. 62/949,917, filed Dec. 18, 2019, which is incorporated herein by reference in its entirety.

BACKGROUND

Technical Field

This disclosure generally relates to systems, methods, and devices for processing biological samples. More specifically, the present disclosure relates to systems, methods, and devices for automated isolation of nucleic acid and/or protein from biological and/or environmental sources.

Related Technology

Certain laboratory procedures remain predominantly carried out using inefficient manual methods which require individual attention by the scientist or lab technician performing the procedure. Many of these procedures would benefit from automation. For example, nucleic acid purification or isolation protocols, such as large-scale plasmid preparation from bacterial culture, are currently a time consuming, inefficient tasks that have not been completely automated. Prior attempts at automating similar protocols, such as commercialized embodiments of systems disclosed in U.S. Pat. Nos. 8,404,198 and 9,808,799 and similar products, suffer from numerous drawbacks, including, for example, not being fully automated and/or not being operable for large volume samples. Gradual improvements such as the introduction of precipitation filters have reduced the hands-on time required. However, even the most advanced nucleic acid purification kits still require substantial time investment, for instance purification of endotoxin free plasmid on maxi, mega or giga scale takes several hours and individual attention.

This is due, at least in part, to the highly technical nature of nucleic acid purification and the variety of disparate tasks that need to be performed during such process. For example, many nucleic acid purification protocols move and route fluids of varying viscosities and densities and do so at different times during the purification protocol. Further, during the process of purifying nucleic acid from a biological sample, it is important for the buffers and reagents to be homogenously mixed with the biological sample and/or filtrates as this can improve the purity and final concentration of the target nucleic acid. It has thus far proven difficult to incorporate these various fluids into an automated process that can provide for timed release, and particularly in a manner that enables mixing of the fluids to create a homogenous solution.

Additionally, supplying each of the various buffers and reagents in an automated system can prove problematic and expensive. The materials housing each of the buffers/reagents should ideally be made of a material that is chemically compatible (e.g., nonreactive or inert) with the solution being stored so that the solution maintains its efficacy and activity through periods of nonuse or storage and until such time that these fluids are implemented for their intended purpose.

The various filtration steps utilized in many nucleic acid purification protocols provide an additional layer of complexity and difficulty to implement in an automated process. For example, different steps within nucleic acid purification protocols require the selective filtration of solutions based on mechanical and/or ionic means and the subsequent washing or purification of components bound to the filters/membranes. This can generate volumes of waste many times greater than the initial volume of biological sample, and the sequestration or disposal of these waste products is a complicating factor to automation.

When performed in the traditional hands-on manner, a technician or scientist uses a variety of different machines and instruments to perform the nucleic acid purification protocol. This can include, for example, using a centrifuge and pipette to concentrate the biological sample and to add measured amounts of buffers with intermittent agitation or vortexing to homogenize each buffer/reagent within the solution. A number of different filters/membranes, columns, or magnetic beads are used with centrifugation or under vacuum to further conduct the nucleic acid purification protocol, and many of these steps generate waste products to be disposed of between centrifugation/vacuuming steps.

The foregoing problems are compounded as the volume of biological sample increases. Larger volumes of buffers and reagents and more robust filters and membranes and columns are generally required when processing large volume biological samples. This can call for more stringent demands on the structural integrity and filtering capacity of the various filter/membranes and provides problems incorporating and monitoring such filter/membranes in any automated process. Further, the larger volumes of buffers and reagents used when processing large volume biological samples generates more waste. Having the capacity and ability to account for this waste presents an additional, unique technical hurdle for any automated process.

Further, because the current nucleic acid purification protocols are dependent upon hands-on, human interaction, there is an inherent risk of contamination, less consistency between sample preparation and processing runs, and an ongoing need for skilled technicians to perform these processes. Importantly, the nucleic acid purification on large scale is an extremely time-consuming procedure, distracting scientists from a central project or task. These factors, among others, are costly and inefficient—whether in an academic or clinical laboratory setting or within commercial enterprises.

Accordingly, there are a number of disadvantages and problems that can be addressed in automating nucleic acid purification, and there is an outstanding need for systems, methods, and devices that can automate the process of nucleic acid purification, particularly those that can incorporate all stages of the purification process into a single consumable element that limits or eliminates user intervention during the nucleic acid purification process.

Similarly, many analogous technical issues need to be addressed for automated protein purification as well. In protein purification, in addition to removing other cellular debris and materials from a protein of interest, there is also a need for the isolated/purified protein to maintain its biological activity. This often requires use of conditions and techniques that do not disrupt the tertiary structure of proteins, that retain any native posttranslational modifications of proteins (e.g. phosphorylation, glycosylation, cysteine disulfide bonds), and that do not introduce non-natural protein modifications (e.g. oxidation, deamidation). While this is difficult to achieve during hands on processes, the technical difficulties in automating protein purification are substantially more.

There is an outstanding need for systems, methods, and devices that can automate the process of protein purification, particularly those that can incorporate all stages of the purification process into a single consumable element that limits or eliminates user intervention during the protein purification process.

BRIEF SUMMARY

Implementations of the present disclosure solve one or more of the foregoing or other problems in the art with automated isolation of target biomolecules, such as a target nucleic acid and/or a target protein, from biological and/or environmental sources.

In particular, one or more implementations can include an apparatus for automated purification of a target biomolecule, such as a target nucleic acid and/or a target protein, from a biological sample. The apparatus can include, for example, (i) an input reservoir for receiving the biological sample, (ii) a first bioprocessing assembly in fluid communication with the input reservoir and a lysis buffer reservoir, (iii) a second bioprocessing assembly in fluid communication with the first bioprocessing assembly and a first elution buffer reservoir, and (iv) a receptacle in fluid communication with the second bioprocessing assembly. The first bioprocessing assembly can be configured to generate a lysate comprising the target biomolecule. The second bioprocessing assembly can include a target-biomolecule binding filter configured to retain the target biomolecule from the first bioprocessing assembly, and the receptacle can be configured to receive an output container for receiving the target biomolecule in purified form from the second bioprocessing assembly. Non-limiting examples can comprise at least two or more than two bioprocessing assemblies.

The apparatuses for automated purification of a target biomolecule, such as a target nucleic acid and/or a target protein, can be associated with any number of reservoirs containing reagents and/or buffers appropriate for use in the automated isolation of target biomolecules from the biological sample. For example, the apparatus can have one or more reservoirs containing resuspension buffer, RNase A (or other enzyme such as proteinase K, Tobacco Etch Virus (TEV) protease, or a universal nuclease), lysis buffer, neutralization buffer, endotoxin removal buffer, chaotropic salt buffer, wash buffer, elution buffer, refolding buffer, isopropanol, 70% ethanol, and/or TE buffer. The contents of these reservoirs can be selected based on the type of target biomolecule to be purified (e.g., whether automatedly purifying a target nucleic acid or a target protein).

In some embodiments, an apparatus of the disclosure is used to purify a target biomolecule from a biological sample. In some embodiments, the biological sample comprises a bacterial culture, a cell culture, a prokaryotic cell culture, an eukaryotic cell culture, an environmental sample, a food or beverage sample, and/or a clinical sample (e.g., urine, blood, plasma, saliva, nasal fluids, aqueous solution of fecal matter, cerebrospinal fluids, or other bodily fluid or exudate). Target biomolecule can be a target nucleic acid, such as genomic DNA, plasmid DNA, or an RNA, or a target protein, such as antibodies, cytokines, viral proteins, or other recombinant pharmaceutical proteins, streptavidin, Protein A, C-reactive protein (CRP), or any naturally-occurring or recombinant protein to be used in functional, structural, or protein interaction assays. As a non-limiting example, a target biomolecule can be plasmid DNA isolated from a bacterial culture, cell culture, biological sample etc. (i.e., the biological sample). As an alternative, non-limiting example, the target biomolecule can be a recombinant or monoclonal antibody isolated from a eukaryotic culture (i.e., the biological sample). In some non-limiting embodiments, the biological sample comprises a large volume bacterial culture, a large volume cell culture, a large volume prokaryotic cell culture, a large volume eukaryotic cell culture, a large volume environmental sample, a large volume food or beverage sample, or a large volume clinical sample. In some further non-limiting embodiments, a biological sample can be a small volume, a medium volume or a large volume sample.

In some embodiments where the target biomolecule is a target nucleic acid, an embodiment of an apparatus for automated purification of a target nucleic acid from a biological sample, comprises: an input reservoir for receiving the biological sample; a first bioprocessing assembly in fluid communication with the input reservoir and a lysis buffer reservoir, the first bioprocessing assembly configured to generate a lysate comprising a target nucleic acid; a second bioprocessing assembly in fluid communication with the first bioprocessing assembly and a first elution buffer reservoir, the second bioprocessing assembly including a nucleic-acid-binding filter configured to retain the target nucleic acid; and a receptacle in fluid communication with the second bioprocessing assembly, the receptacle configured to receive an output container for receiving the target nucleic acid in purified form.

In some embodiments where the target biomolecule is a target nucleic acid, an embodiment of an apparatus for automated purification of a target nucleic acid from a biological sample can additionally, or alternatively, include (i) a first bioprocessing assembly configured to receive the biological sample, the first bioprocessing assembly comprising a waste separation filter and a plurality of reservoirs fluidically coupled to the waste-separation filter; (ii) a second bioprocessing assembly comprising an anion exchange membrane, a washing solution reservoir fluidically coupled to the anion exchange membrane and a first elution buffer reservoir fluidically coupled to the anion exchange membrane; (iii) and a third bioprocessing assembly comprising a precipitation filter and a second elution buffer reservoir fluidically coupled to the precipitation filter.

Apparatuses or devices of the present disclosure can also include a consumable cartridge for use in an automated biomolecule purification system, such as an automated target nucleic acid purification system or an automated target protein purification system. An exemplary embodiment consumable cartridge can include an input reservoir for receiving a bacterial culture, a cell culture, or eukaryotic cell culture, a first bioprocessing assembly in fluid communication with the input reservoir and with a lysis buffer reservoir, a second bioprocessing assembly in fluid communication with the first bioprocessing assembly and with an elution buffer reservoir, and an output container in fluid communication with the second bioprocessing assembly. The first bioprocessing assembly can be configured to generate a lysate from the bacterial or eukaryotic cell culture where the lysate includes, for example, a target nucleic acid. In such an embodiment, the second bioprocessing assembly can include a silica-based filter configured to retain the target nucleic acid, and the output container can be configured to receive the target nucleic acid in purified form from the second bioprocessing assembly. The consumable cartridge can be configured to associate with an automated nucleic acid purification system to automatedly purify the target nucleic acid without human interaction.

Methods of the present disclosure can include a method for automated purification of a target biomolecule, such as a target nucleic acid and/or target protein, from a biological sample. Such an exemplary method can include the steps of receiving the biological sample at an input reservoir and without further human interaction, generating a lysate from the biological sample containing the target biomolecule, such as a target nucleic acid and/or a target protein, at a first bioprocessing assembly, receiving a target-biomolecule-containing portion of the lysate, such as a target-nucleic-acid-containing portion of the lysate and/or a target-protein-containing portion of the lysate, at a second bioprocessing assembly, retaining the target biomolecule on a biomolecule binding filter (e.g., a nucleic-acid binding filter and/or a target protein binding filter) at the second bioprocessing assembly, and eluting a purified form of the target biomolecule from the biomolecule binding filter into an output container.

In some embodiments, the methods can additionally include capturing a cellular content of the biological sample at a first membrane of the first bioprocessing assembly and resuspending at least a portion of the cellular content in one or more of a resuspension buffer, an RNAse solution, or a lysis buffer. Resuspending at least a portion of the cellular content can include, for example, backwashing the first membrane by transferring a resuspension solution, which can include one or more of a resuspension buffer, an RNAse solution, or a lysis buffer, from a fluidic channel disposed on a second side of the first membrane and through the first membrane.

The methods can additionally include target-biomolecule-specific processing steps. For example, in embodiments where the target biomolecule comprises a target nucleic acid, the methods can additionally include mixing the lysate with a neutralization buffer to form a neutralized lysate and separating the target-nucleic-acid-containing portion from a waste portion of the neutralized lysate. The methods can also/optionally include mixing an endotoxin removal buffer with the target-nucleic-acid containing portion of the lysate. In some instances, retaining the target nucleic acid on the nucleic-acid binding filter at the second bioprocessing assembly includes passing the target-nucleic-acid containing portion of the lysate through an anion exchange membrane and removing the target-nucleic-acid containing portion of the lysate from the anion exchange membrane and precipitating the target nucleic acid to desalt and/or concentrate the target nucleic acid. The precipitated target nucleic acid can be further captured at a precipitator membrane, in accordance with some disclosed methods.

Alternatively, retaining the target nucleic acid on the nucleic-acid binding filter at the second bioprocessing assembly can include passing the target-nucleic-acid containing portion of the lysate through a silica-based or advanced silica-based filter. In such exemplary methods, the target-nucleic-acid containing portion of the lysate can be mixed with a chaotropic salt buffer prior to passing the target-nucleic-acid containing portion of the lysate through the silica-based filter.

Some embodiments are directed toward a nucleic acid purification instrument that may be utilized in an automated nucleic acid purification process. The instrument may interface with an inserted nucleic acid purification cartridge to control movement and routing of fluids within the cartridge, to control the actuation of seals and valving, and to control the timing of purification process steps, among other features.

In one embodiment, a purification instrument comprises a casing having an internal compartment configured in size and shape for receiving a purification cartridge, a selectively closable access door providing access to the internal compartment, and a pump assembly disposed within the interior chamber and configured to provide pumping action through peristaltic motion. The instrument, in some embodiments, can further comprise a clamping mechanism disposed within the internal compartment and configured to move between an open position in which the internal compartment is accessible and a closed position in which the clamping mechanism compresses an inserted purification cartridge. The clamping mechanism can thereby assist in maintaining the integrity of fluid seals of the cartridge during the relatively high pressures it may be subjected to during a purification process.

The instrument can include one or more sensors for determining component positions, an operational state of the instrument, process status, and/or other indications. For example, one or more position sensors may be utilized to ensure proper insertion of a cartridge, proper cartridge status, and/or safe enclosure of the cartridge prior to initiation of automated moving parts. The one or more sensors may be communicatively coupled to a controller, and the controller may be configured to automatedly control instrument operation based at least in part on information received from the one or more sensors. For example, the controller may be configured to prevent initiation of a purification process and/or provide a notification/alarm to the user if it determines that a cartridge is improper, has been inserted improperly, is unable to effectively collect a purified product, is loaded with an unsuitable sample, and/or is not properly and safely enclosed within the instrument.

The instrument may also include one or more actuators for interacting with an inserted cartridge to provide fluid pumping, seal opening and fluid release, air vent opening, valve control, and/or fluid mixing, for example. In some embodiments, a pump assembly for interfacing with one or more fluid channels of an inserted cartridge includes a camshaft and a plurality of cam members extending transversely from the camshaft. Cam element tips engage with an associated fluid channel. The pump assembly is configured such that rotation of the camshaft causes a linear peristaltic motion of the cam element tips that thereby peristaltically compresses the fluid channel and drives fluid movement through the channel.

In one embodiment, a method for automated purification of a target nucleic acid from a biological sample comprises the steps of providing a nucleic acid purification apparatus (i.e., instrument), loading a purification cartridge through the access door and into the interior compartment of the apparatus, and initiating a purification procedure using the instrument. The initiation of the purification procedure causes the instrument to automatedly purify the target nucleic acid without the need for further human interaction.

In some embodiments, the method further comprises closing the access door of the instrument and the instrument actuating the clamping mechanism such that it moves to the closed position to compress the inserted cartridge and thereby assist in fluidically sealing the loaded purification cartridge. The method may also comprise the step of determining that the purification cartridge is fully loaded and/or determining that the access door is fully closed prior to initiating the purification procedure, such as through the use of one or more position sensors to detect the position of the cartridge. The method may also comprise the step of determining that an output container is properly positioned at the cartridge and issuing an alarm/notification and/or preventing initiation of the purification procedure if it is determined that the output container is absent.

In some embodiments, the method may include the step of determining an optical density of a biological sample within the purification cartridge. The instrument may operate as a "smart" instrument capable of varying one or more process parameters in response to received input and/or sensor data. For example, an optical density measurement may be utilized to adjust one or more parameters of the purification procedure such as a volume of one or more reagents used in the purification procedure, duration of pumping via the pump assembly, or speed of pumping via the pump assembly.

In some embodiments, an initial optical density reading is taken prior to initiating the purification procedure to determine whether the purification cartridge has been previously used. For example, where an optical density reading is substantially equal to an air blank reading, it may be taken to indicate that a culture input reservoir of the biological sample cartridge remains unbroken and the cartridge is thus unused.

The systems and apparatuses disclosed herein can additionally include or be associated with a fluid release system for holding and selectively releasing a fluid. Such an exemplary system can include a flexible gasket, a reservoir disposed on a first side of the flexible gasket that is configured to hold the fluid, a frangible seal disposed between the flexible gasket and the fluid reservoir, and an actuator disposed on a second side of the flexible gasket that is operable to deflect the flexible gasket and cause the frangible seal to breach, thereby selectively releasing the fluid from the reservoir.

Additionally, in some embodiments, the fluid release system includes a flexible air vent, a frangible air seal disposed on a first side of the flexible air vent, and a venting actuator disposed on a second side of the flexible air vent. The venting actuator is operable to selectively deflect the flexible air vent toward the frangible air seal and thereby breach the frangible air seal to vent air into the reservoir.

The fluid release system may be associated with any number or type of mixing chamber or reservoir disclosed herein and may enable the selective release of fluids from these chambers/reservoirs at an appropriate time to effect different processes and fluidic movement within the nucleic acid purification systems and associated cartridges. Accordingly, embodiments of the present disclosure additionally include an automated system for selectively releasing a fluid that includes an automated nucleic acid purification system comprising at least one component of the disclosed fluid release systems and a biological sample cartridge for use with the automated nucleic acid purification system and that includes at least one other component of the disclosed fluid release systems.

Methods for selectively releasing a fluid from a reservoir in an automated process can include contacting a flexible gasket with an actuator, moving the actuator to deflect the flexible gasket toward a frangible seal associated with the reservoir, and causing the flexible gasket to breach the frangible seal, thereby releasing the fluid from the reservoir.

The methods for selectively releasing a fluid from a reservoir can additionally include contacting a flexible air vent with a venting actuator, moving the venting actuator to deflect the flexible air vent toward a frangible air seal, and causing the flexible air vent to breach the frangible air seal.

The systems, methods, and apparatuses of the present disclosure can also include an apparatus for controlled movement of fluids. The apparatus can include a first external layer having a first side that includes a series of channels and a second side. The apparatus can additionally include a second external layer disposed opposite the first side of the first external layer and an elastomer layer disposed between the first and second external layers. The elastomer layer can include an arrangement of sealing ribs that corresponds to the series of channels and can be configured to fluidically separate the channels when the elastomer layer is compressed between the first and second external layers.

In some embodiments, the apparatus can additionally include a nominal gap between the elastomer layer and one or both of the first external layer or the second external layer such that when the elastomer layer is compressed between the first and second external layers, a compressed portion of the sealing ribs is displaced within the nominal gap. Additionally, or alternatively, the apparatus can include a valve associated with the series of channels, the valve being selectively moveable between a closed position and an open position to respectively restrict or allow fluid flow across the valve.

The aperture of the apparatus can, in some embodiments, provide access to a deflectable portion of the elastomer layer, the deflectable portion comprising a valve sealing rib extending from the elastomer layer toward the first external layer. The valve sealing rib may contact the first external layer when the valve is in the closed position and may be separated from the first external layer when the valve is in the open position. Additionally, or alternatively, the apparatus can include a plunger in contact with the deflectable portion of the valve. In such embodiments, the plunger may be configured in size and shape to be passable into the aperture to deflect the deflectable portion and move the valve toward the closed position.

In one embodiment, the apparatus is configured to withstand at least 500 lbf, preferably up to 15,000 lbf, applied across an entire length of the arrangement of sealing ribs. Additionally, the arrangement of sealing ribs can be compressed to withstand at least 30 psi, preferably at least 60 psi, of fluid pressure before leaking, and/or when the elastomer layer is compressed between the first and second external layers, the sealing ribs are compressed at least 20%, preferably at least 30%.

Embodiments of the present disclosure additionally include methods for controlling movement of fluid. An exemplary method can include providing the apparatus for controlled movement of fluids disclosed herein to a system for automated purification of a target nucleic acid or a target protein, causing one or more plungers to open a valve within the apparatus such that the open valve allows fluid communication between an upstream and downstream section of the series of channels, and causing a pump to move fluid from the upstream section to the downstream section. The disclosed methods for controlling movement of fluid may additionally include the step of providing a biological sample comprising the target nucleic acid or target protein to the apparatus, and as provided throughout the application, the biological sample may be, in some embodiments, a bacterial culture and the target nucleic acid may be plasmid DNA (or a cell culture and the target protein can be any cellular protein).

Accordingly, systems, methods, and devices for automated purification of a target biomolecule, such as nucleic acid or protein, from a biological sample are disclosed.

Implementations of the present disclosure solve one or more of the foregoing or other problems in the art with automated isolation of target biomolecules, such as target nucleic acids or proteins, from biological, clinical, and/or environmental sources.

In particular, one or more implementations can include an apparatus for automated purification of a target protein from a biological sample, the apparatus comprising: an input reservoir for receiving the biological sample; a first bioprocessing assembly in fluid communication with the input reservoir and a lysis buffer reservoir, the first bioprocessing assembly configured to generate a lysate comprising a target protein; a second bioprocessing assembly in fluid communication with the first bioprocessing assembly and a first elution buffer reservoir, the second bioprocessing assembly including a protein-binding support configured to retain the target protein; and a receptacle in fluid communication with the second bioprocessing assembly, the receptacle configured to receive an output container for receiving the target protein in purified form.

In one embodiment, the apparatus comprises a consumable cartridge for use in an automated protein purification system. In some instances, a consumable cartridge for use in an automated protein purification system comprises: an input reservoir for receiving a biological sample comprising a target protein or protein of interest; a first bioprocessing assembly in fluid communication with the input reservoir and with a lysis buffer reservoir, the first bioprocessing assembly configured to generate a lysate from the biological sample, the lysate comprising a target protein; a second bioprocessing assembly in fluid communication with the first bioprocessing assembly and with an elution buffer reservoir, the second bioprocessing assembly comprising a support or filter configured to retain the target protein; and an output container in fluid communication with the second bioprocessing assembly, the output container configured to receive the target protein in purified form, wherein the consumable cartridge is configured to associate with an automated protein purification system and automatedly purify the target protein without human interaction. The cartridge can additionally comprise in the second bioprocess chamber or in additional bioprocessing chambers one or more components for column chromatography, affinity chromatography, gel filtration chromatography, ion exchange chromatography, fast protein liquid chromatography or any combination thereof. In some instances, these components can be located upstream of the target protein binding support. In some instances, one or more of these components may comprise the target protein binding support.

In some embodiments, an automated protein purification system can additionally comprise one or more controller or controllers including computerizes systems that control a variety of fluid movement, sample movement, reagent distribution and other processes.

Automated protein purification apparatus, systems and consumable cartridges of the disclosure are compatible for use with a variety of samples such as but not limited to sample comprises a biological sample, a tissue, a biopsy, a cell-line, a cell culture, a cell, a cell suspension, urine, saliva, cerebrospinal fluid, blood, serum, plasma, an aqueous solution of fecal matter, other bodily fluids or exudates, eukaryotic cells selected from the group consisting of rodent, insect, primate, and human cells, prokaryotic cells or cell suspensions comprising prokaryotic cells, bacterial cells, yeast cells and the like.

In some embodiments, the first bioprocessing assembly comprises a clarification filter. In some instances, the clarification filter is in fluid communication with the input reservoir and the lysis buffer reservoir, the clarification filter being configured to separate a target-protein-containing portion of the biological sample from a first waste portion of the biological sample.

In instances where the biological sample is a cell-line or tissue comprising a plurality of cells, the target-protein-containing portion comprises a protein in the cell-line or tissue and the first waste portion comprises lysed cells and optionally culture media.

In some embodiments, the first bioprocessing assembly comprises a cell capture or concentration filter. In some embodiments, the cell capture or concentration filter is disposed upstream of a clarification filter. In instances where the cell capture or concentration filter is in fluid communication with the input reservoir and the lysis buffer reservoir, the cell capture or concentration filter being configured to separate a target-protein-containing portion of the biological sample from a first waste portion of the biological sample.

In some embodiments, the apparatus further comprises one or more additional bioprocessing chambers having reagents for protein purification. In some instances, one or more filters within the apparatus comprises a hollow fiber filter.

For example, exemplary automated protein purification apparatuses, systems, and consumable cartridges of the present disclosure can include a lysis buffer having at least one lysis agent and a DNase. In some embodiments, automated protein purification systems disclosed herein can additionally include a cleavage buffer and proteolytic enzyme (e.g., TEV protease) to remove affinity tags from a target protein. For example, a DNase-treated lysate can be passed over a column or filter that binds a given affinity tag, and after washing the column, the cleavage buffer and proteolytic enzyme can be used to release the target protein from the column/filter. The digested target protein can be further purified or collected.

The protein purification systems and apparatuses disclosed herein can additionally include or be associated with a fluid release system for holding and selectively releasing a fluid. Such an exemplary system can include a flexible gasket, a reservoir disposed on a first side of the flexible gasket that is configured to hold the fluid, a frangible seal disposed between the flexible gasket and the fluid reservoir, and an actuator disposed on a second side of the flexible gasket that is operable to deflect the flexible gasket and cause the frangible seal to breach, thereby selectively releasing the fluid from the reservoir.

Additionally, in some embodiments, the fluid release system includes a flexible air vent, a frangible air seal disposed on a first side of the flexible air vent, and a venting actuator disposed on a second side of the flexible air vent. The venting actuator is operable to selectively deflect the flexible air vent toward the frangible air seal and thereby breach the frangible air seal to vent air into the reservoir.

The fluid release system may be associated with any number or type of mixing chamber or reservoir disclosed herein and may enable the selective release of fluids from these chambers/reservoirs at an appropriate time to effect different processes and fluidic movement within the protein purification systems and associated cartridges. Accordingly, embodiments of the present disclosure additionally include an automated system for selectively releasing a fluid, at least one component of which is operable by an automated protein purification system and at least one other component of the disclosed fluid release systems included within a biological sample cartridge configured for use with the automated protein purification system.

Methods for selectively releasing a fluid from a reservoir in an automated process can include contacting a flexible gasket with an actuator, moving the actuator to deflect the flexible gasket toward a frangible seal associated with the reservoir, and causing the flexible gasket to breach the frangible seal, thereby releasing the fluid from the reservoir.

The methods for selectively releasing a fluid from a reservoir can additionally include contacting a flexible air vent with a venting actuator, moving the venting actuator to deflect the flexible air vent toward a frangible air seal, and causing the flexible air vent to breach the frangible air seal.

The systems, methods, and apparatuses of the present disclosure can also include an apparatus for controlled movement of fluids. The apparatus can include a first external layer having a first side that includes a series of channels and a second side. The apparatus can additionally include a second external layer disposed opposite the first side of the first external layer and an elastomer layer disposed between the first and second external layers. The elastomer layer can include an arrangement of sealing ribs that corresponds to the series of channels and can be configured to fluidically separate the channels when the elastomer layer is compressed between the first and second external layers.

In some embodiments, the apparatus can additionally include a nominal gap between the elastomer layer and one or both of the first external layer or the second external layer such that when the elastomer layer is compressed between the first and second external layers, a compressed portion of the sealing ribs is displaced within the nominal gap. Additionally, or alternatively, the apparatus can include a valve associated with the series of channels, the valve being selectively moveable between a closed position and an open position to respectively restrict or allow fluid flow across the valve.

The aperture of the apparatus can, in some embodiments, provide access to a deflectable portion of the elastomer layer, the deflectable portion comprising a valve sealing rib extending from the elastomer layer toward the first external layer. The valve sealing rib may contact the first external layer when the valve is in the closed position and may be separated from the first external layer when the valve is in the open position. Additionally, or alternatively, the apparatus can include a plunger in contact with the deflectable portion of the valve. In such embodiments, the plunger may be configured in size and shape to be passable into the aperture to deflect the deflectable portion and move the valve toward the closed position.

In one embodiment, the apparatus is configured to withstand at least 500 lbf, preferably up to 15,000 lbf, applied across an entire length of the arrangement of sealing ribs. Additionally, the arrangement of sealing ribs can be compressed to withstand at least 30 psi, preferably at least 60 psi, of fluid pressure before leaking, and/or when the elastomer layer is compressed between the first and second external layers, the sealing ribs are compressed at least 20%, preferably at least 30%.

Embodiments of the present disclosure additionally include methods for controlling movement of fluid. An exemplary method can include providing the apparatus for controlled movement of fluids disclosed herein to a system for automated purification of a target biomolecule, such as a target nucleic acid and/or target protein, causing one or more plungers to open a valve within the apparatus such that the open valve allows fluid communication between an upstream and downstream section of the series of channels, and causing a pump to move fluid from the upstream section to the downstream section. The disclosed methods for controlling movement of fluid may additionally include the step of providing a biological sample comprising the target biomolecule, and as provided throughout the application, the biological sample may be, in some embodiments, a cell in a cell-line, a cell culture, a tissue, a biopsy sample, blood, serum, plasma, in a eukaryote, in a prokaryote, or any other biological material and the target biomolecule may be any target nucleic acid and/or target protein from these cells.

Some embodiments describe methods comprising automatedly isolating or purifying a target protein from the cellular lysate using an apparatus or system as described herein. Such an exemplary method can include the steps of receiving the biological sample at an input reservoir and without further human interaction, generating a lysate from the biological sample containing the target protein at a first bioprocessing assembly, receiving a target-protein-containing portion of the lysate at a second bioprocessing assembly, retaining the target protein on a protein binding filter or protein binding support at the second bioprocessing assembly, and eluting a purified form of the target protein from the support or filter into an output container.

In some embodiments, the methods can additionally include capturing a cellular content of the biological sample at a first membrane of the first bioprocessing assembly and resuspending at least a portion of the cellular content in one or more of a resuspension buffer, a DNase solution an RNAse solution, or a lysis buffer. Resuspending the at least a portion of the cellular content can include, for example, backwashing the first membrane by transferring a resuspension solution, which can include one or more of a resuspension buffer, an RNAse solution, a DNase solution, or a lysis buffer, from a fluidic channel disposed on a second side of the first membrane and through the first membrane.

The methods can additionally include mixing the lysate with a neutralization buffer to form a neutralized lysate and separating the target-protein-containing portion from a waste portion of the neutralized lysate. In some embodiments, the methods include mixing an endotoxin removal buffer with the target-protein containing portion of the lysate.

The method can additionally include one or more additional steps of contacting the target-protein containing lysate with additional protein purification/isolation reagents and capturing the target protein on a support or filter that can bind to the target protein. Additional steps of the method to isolate a target protein can comprise one or more of column chromatography, affinity chromatography, gel filtration chromatography, ion exchange chromatography, fast protein liquid chromatography or any combination thereof. Target protein can then be eluted from the support or filter for further downstream processing or use.

Accordingly, systems, methods, and devices for automated purification of a target protein from a biological sample are disclosed.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are therefore not to be considered as limiting the scope in any way.

In the drawings, a drawing number may include separate letters appended thereto. For example, FIG. 2 may include FIG. 2A and FIG. 2B. In that case, the drawing number may be used without the appended letter (e.g., FIG. 2) to generally refer to every instance of the drawing, while the drawing label will include an appended letter (e.g., FIG. 2A) to refer to a specific instance of the drawing. The disclosure will be described and explained with additional specificity and detail through the use of the accompanying drawings in which:

FIGS. 5A through 5K illustrate sequentially the movement of a sample and various fluids through an exemplary purification cartridge when acted upon by an associated purification instrument;

FIGS. 8A through 8C illustrate an exemplary embodiment of a fluid release system for holding and selectively releasing fluid from a reservoir or mixing chamber within a purification cartridge;

DETAILED DESCRIPTION

Figure 1:
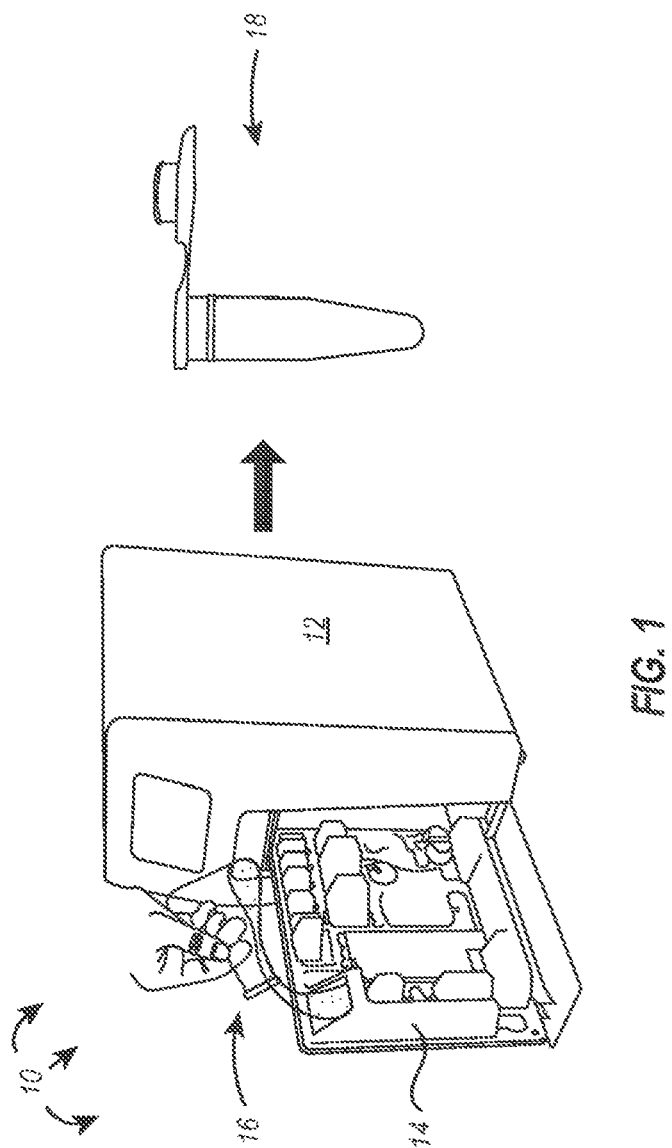
FIG. 1 illustrates a general system for the automated purification of a target biomolecule, such as a target nucleic acid and/or a target protein, from a biological sample.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Any headings and subheadings used herein are for organizational purposes only and are not meant to be used to limit the scope of the description or the claims.

Overview and Advantages of Exemplary Target Biomolecule Purification Systems

As provided above, there are a number of disadvantages and problems that can be addressed automating purification of target biomolecules, such as target nucleic acids and/or target proteins, in particular for processing large sample volumes. There is an outstanding need for systems, methods, and devices that can automate the process of target biomolecule purification, such as the respective processes for purifying target nucleic acids and/or target proteins. In particular, there is an outstanding need for systems, methods, and devices that can incorporate all stages of the purification process into a single consumable element that limits or eliminates user intervention during the purification process.

Embodiments of the present disclosure solve one or more of the foregoing problems in the art of automated target biomolecule purification. For example, as shown in FIG. 1, a system 10 for the automated purification of a target biomolecule (such as a target nucleic acid and/or target protein) can employ the combined use of a purification instrument 12 and a purification cartridge 14 to isolate and purify the target biomolecule from a biological sample with limited user interaction. In a preferred embodiment, a user adds a biological sample 16 containing the target biomolecule to the purification cartridge 14 and loads the purification cartridge 14 into the purification instrument 12 where the target biomolecule is then automatedly isolated, purified, and deposited into an output container 18 associated with the system 10—all without further user interaction with the system. In this way, target biomolecule purification systems of the present disclosure (such as the nucleic acid purification systems and protein purification systems disclosed herein) can include a self-contained system. In some embodiments, target biomolecule purification apparatus and systems of the disclosure enable a fully automated large-scale target biomolecule purification (e.g., endotoxin free maxi-scale plasmid DNA purification from 100-200 mL bacterial culture input or recombinant pharmaceutical protein purification from 500 mL eukaryotic cell culture input) in reduced time compared to manual methods. In some instances, the disclosed systems can automatedly isolate and purify a target biomolecule in less than an hour (e.g., purifying a target nucleic acid with a total runtime of about 45 min and only about 2 min setup time).

Additional benefits can be realized through implementation of the disclosed systems, methods, and devices. For example, the systems disclosed herein can include a walk-away benchtop instrument that is robust and capable of processing a biological sample (e.g., bacterial cultures, eukaryotic cell cultures, clinical samples, food/beverage samples, or environmental samples) of varying input densities and can achieve high purity of the target biomolecule, such as a high purity nucleic acid ("low endo" or "endotoxin free" in case of plasmid DNA purified from bacterial culture). In some embodiments, the purification instrument can be cloud-enabled and "smart" with a built-in optical density sensor and communication hardware and software configured to notify the user of the density of input culture and/or dynamically trigger different purification protocols depending on the optical density (e.g., A600) readout and/or type of input sample received.

Additional benefits of the disclosed systems, methods, and devices include, for example, a one-piece purification cartridge design that integrates all the reagents, filters, pumps, fluid channels, input reservoir, waste reservoir, and final output container into a single cartridge. This limits the user's interaction to a single component of the system, thereby reducing errors, increasing consistency, and significantly reducing hands-on time during the target biomolecule purification process. The disclosed systems are additionally much easier to use and can therefore reduce the technical expertise or know-how required to purify a target biomolecule from a biological sample.

This contrasts strongly with manual kits, which require the technically specialized user to obtain and manipulate several reagents, purification columns, centrifuges, pipettes, pipette tips, intermediate containers, and the final output container. Similarly, manual and semiautomated systems require a large number of consumable elements to be manipulated by the user in order to accomplish purification of biomolecules, such as nucleic acids and/or proteins. Unlike the manual processes, which require users to interact with open reagent containers, the disclosed purification cartridges allow the reagents to remain sealed during the setup and purification steps. Some embodiments of the present disclosure also enable the automated release of reagents at various, appropriate times in the purification process, which is an improvement over prior manual and semiautomated processes that require the user to break the reagent seal or directly access reagents prior to and/or during execution of the protocol.

In some embodiments, the purification cartridge is a consumable, disposable element within the system, and in some instances, this can result in a lower cost consumable compared to prior art kits and systems. For example, in some embodiments, the cartridge is made with or incorporates thermoformed plastics, and the use of thermoform plastics instead of costlier injection molding processes enables a lower cost, high volume solution for the generation of consumable purification cartridges. Thermoformed plastics have been traditionally used as packaging materials because of the reduced cost associated with their manufacture. Within embodiments of the present disclosure where the purification cartridge is made with or includes thermoformed plastics, such design criteria represent a significant departure from typical applications, as the product is made from thermoformed plastic rather than the packaging for the product, which is the norm. Unexpectedly, the use of thermoformed plastics yielded a suitable, nonreactive purification cartridge system at a reduced cost and without a substantial loss of utility.

As an additional example, some embodiments use a combination of the purification instrument and the purification cartridge to form fluid tight seals within the purification cartridge. This form of sealing can allow for less expensive and simpler manufacturing methods because, for example, the purification cartridge does not incorporate traditional, lengthy fluid tight seals often formed by costly, complex ultrasonic welds. This, in isolation from or combination with the significantly lower cost of thermoforming, can greatly reduce the cost and manufacturing time of the purification cartridge.

Further, embodiments of the purification cartridge can include an elastomer layer sandwiched between two thermoformed outer layers. Within such embodiments that utilize an elastomer layer between two thermoformed layers, the elastomer layer can be used for valving purposes, allowing for a simpler assembly of the consumable in manufacturing as only one component is used for the valves instead of individual components for every valve. This design also allows for a very simple, reliable, single-axis actuator. For example, the elastomer's natural elasticity and inclination to rebound to its former shape also allows the actuator to effect a change (e.g., valving or releasing of fluids within the cartridge) by pressing against the elastomer or by releasing pressure from the elastomer—and without applying an opposing force and/or in the absence of an opposing actuator—which simplifies the valving, fluid flow control, and actuation within the system.

Purification Cartridges

The following disclosure relates to exemplary embodiments of a purification cartridge that may be utilized to provide automated purification of a target biomolecule, such as a target nucleic acid and/or a target protein, from a biological sample. The purification cartridge may be utilized with other components and/or instruments described herein. For example, the cartridge may be configured to be received and interface with a purification instrument such as the instrument 12 described and illustrated in FIG. 1 or any of the other purification instruments described herein.

Cartridge Overview

As provided above, conventional target biomolecule purification procedures, such as nucleic acid purification and/or protein purification procedures, are manual lab processes requiring relatively high levels of lab technician know-how and time. While a well-trained lab technician may be able to handle the various operational parameters involved in the process, there is an outstanding need for systems, methods, and devices that can automate the process of target biomolecule purification, such as nucleic acid purification and/or protein purification, particularly those that can incorporate all stages of the target biomolecule purification process into a single consumable element that limits or eliminates user intervention during the purification process.

Designing a disposable cartridge capable of effectively automating large portions of the process is challenging for several reasons. For example, a cartridge configured to carry out all stages of the nucleic acid and/or protein purification process should be capable of storing and timely dispensing (or otherwise acquiring and dispensing on demand) the various reagents and buffers associated with the respective purification protocols. The cartridge should additionally be capable or configured to move and route fluids of varying viscosities and densities, often in conjunction with dispensing appropriate reagents and/or buffers, mix disparate fluids together, and control the passage of fluids over and/or through appropriate filters or membranes. Such a cartridge should also be safe for users to operate and be able to maintain appropriate fluid separation/seals throughout the biomolecule purification process.

As described in more detail below, the purification cartridges described herein are capable of meeting one or more of the above-mentioned challenges. For example, the purification cartridges may be configured to associate with a purification instrument such that a user loads the biological sample containing the target biomolecule, such as a target nucleic acid and/or target protein, into the cartridge and inserts the cartridge into the instrument whereupon the target biomolecule is isolated and purified without further user interaction from the user, thereby providing a cartridge configured to carry out all stages of the biomolecule purification process.

As an additional example, the purification cartridges disclosed herein may be self-contained solutions incorporating each of the many and varied buffers and reagents required for biomolecule purification, such as nucleic acid purification and/or protein purification, in separate reservoirs and in such a way that each may be selectively released at the appropriate time during the biomolecule purification process. Additionally, the purification cartridges disclosed herein can be configured with a plurality of interconnected and cooperative conduits, valves, and pumps to move and route fluids of varying viscosities and densities throughout the cartridge during the biomolecule purification process. The cartridges may additionally include mixing chambers outfitted with magnetic stir bars and that are in fluid communication with the cartridge conduits and reservoirs to provide homogenous mixtures throughout the purification process. Additionally, as provided below, cartridges of the present disclosure can be safely sealed as a self-contained consumable, which increases safety to users, decreases the risk of contamination of reagents/buffers, and provides for increased ease-of-use in the automated biomolecule purification process.

Figure 2:
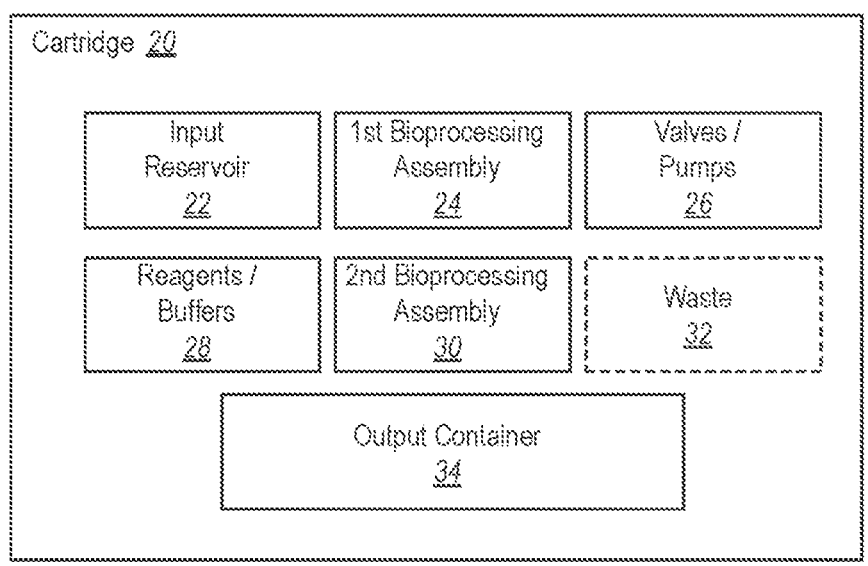
FIG. 2 illustrates various components of an exemplary cartridge configured for use within a system for the automated purification of a target biomolecule, such as a target nucleic acid and/or a target protein, from a biological sample.

FIG. 2 illustrates a schematic of the general features and components of an exemplary cartridge 20 configured for use within a system for the automated purification a target biomolecule (e.g., a target nucleic acid and/or target protein) from a biological sample. As shown, the cartridge 20 includes an input reservoir 22 that is configured to receive the biological sample containing the target biomolecule. In some embodiments, purification cartridges disclosed herein, including cartridge 20 illustrated in FIG. 2, are preferably configured to process large-volume samples. Accordingly, the input reservoir 22 can be sized and shaped to receive between about 5 mL-5 L of biological sample. In some embodiments, the input reservoir can be configured to receive at least 10 mL of biological sample, at least 50 mL of biological sample, at least 100 mL of biological sample, at least 150 mL of biological sample, at least 200 mL of biological sample, at least 250 mL of biological sample, or at least 500 mL of biological sample. In the same or alternative embodiments, the input reservoir can be configured to receive less than 50 mL, less than 100 mL of biological sample, less than 150 mL of biological sample, less than 200 mL of biological sample, less than 250 mL of biological sample, less than 500 mL, less than 1 L of biological sample, less than 2 L of biological sample, or less than 5 L of biological sample. It should be appreciated that the input reservoir can be sized and shaped to receive a volume of biological sample that falls within a range of volumes having a lower bound and an upper bound selected from the foregoing minimum and maximum volumes. It should also be appreciated that systems, apparatus, and cartridges of the disclosure can be scaled down and sized and shaped for processing smaller sample volumes than those disclosed above.

In a preferred embodiment, the input reservoir is configured in size and shape to receive 50 mL-250 mL of bacterial culture containing plasmid DNA—the target nucleic acid. The input reservoir 22 can additionally, or alternatively, be configured to receive other biological samples, such as other cell cultures, eukaryotic cell cultures, clinical samples or environmental samples. In one embodiment, the input reservoir 22 is configured to receive up to 1 L, up to 1.5 L, up to 2 L, or any range of volumes recited above of a clinical sample, such as urine, an aqueous solution of fecal matter, or other bodily fluid or exudate. The input reservoir 22 can additionally, or alternatively, be configured to receive a large volume environmental sample, such as a water sample or the like.

In addition to the input reservoir 22, the cartridge 20 may additionally include at least two bioprocessing assemblies 24, 30. A first bioprocessing assembly 24 can be in fluid communication with the input reservoir 22 and can be configured to generate a lysate from the biological sample that includes the target biomolecule. For example, the first bioprocessing assembly 24 can be in fluid communication with a lysis buffer reservoir such that the biological sample in the input reservoir 22 can be joined with lysis buffer at the first bioprocessing assembly 24 to generate the lysate containing the target biomolecule. The second bioprocessing assembly 30 can be in fluid communication with the first bioprocessing assembly 24 can include a biomolecule-binding filter (e.g., target-nucleic-acid binding filter and/or target-protein-binding filter) for retaining the target biomolecule.

The cartridge 20 can additionally include a plurality of reagents and buffers 28 fluidically coupled to the first and/or second bioprocessing assembly 24, 30 and a series of valves and pumps 26 for coordinating movement of various fluids throughout the cartridge 20 during the automated purification process. It should be appreciated that, when used, pumps of the present disclosure are operable to coordinate movement of various fluids throughout the cartridge by, for example, pushing and/or pulling fluids (e.g., operable to apply a positive and/or negative pressure) through channels connecting components of and within bioprocessing assemblies within the cartridge. This can be achieved by strategically placing the pump within and/or between bioprocessing assemblies such that the pump is located upstream and/or downstream of the fluid to be moved. For example, a pump placed upstream of a fluid can push the fluid through the cartridge, and a pump placed downstream of a fluid can pull the fluid through the cartridge. As it should be appreciated, a single pump may be operable to pull a fluid at one step in the purification process and push a fluid at another step. For example, a valve may be positioned within the cartridge to pull fluid through a filter/membrane at a first step of the purification process and may, at a later step in the purification process, act to push fluid through the same or different filter/membrane.

With continued reference to FIG. 2, the cartridge 20 may also include a receptacle in fluid communication with the second bioprocessing assembly that is configured to receive an output container 34 for collecting the target biomolecule in purified form.

The cartridge 20 of FIG. 2 is shown as optionally including a waste reservoir 32. In some embodiments, the waste generated during the purification process can be captured and stored on the cartridge itself. This can beneficially allow the cartridge 20 to be a single, self-contained disposable cartridge, and by collecting all the waste within the cartridge that is produced during the purification process, it can beneficially reduce user exposure to these waste products and sequester the various chemicals and solutions and transferable container. Additionally, by collecting the waste products in the cartridge, the purification instrument is not exposed to and does not contact the waste, which reduces the likelihood of cross-contamination between samples using the same instrument.

Figure 3A:
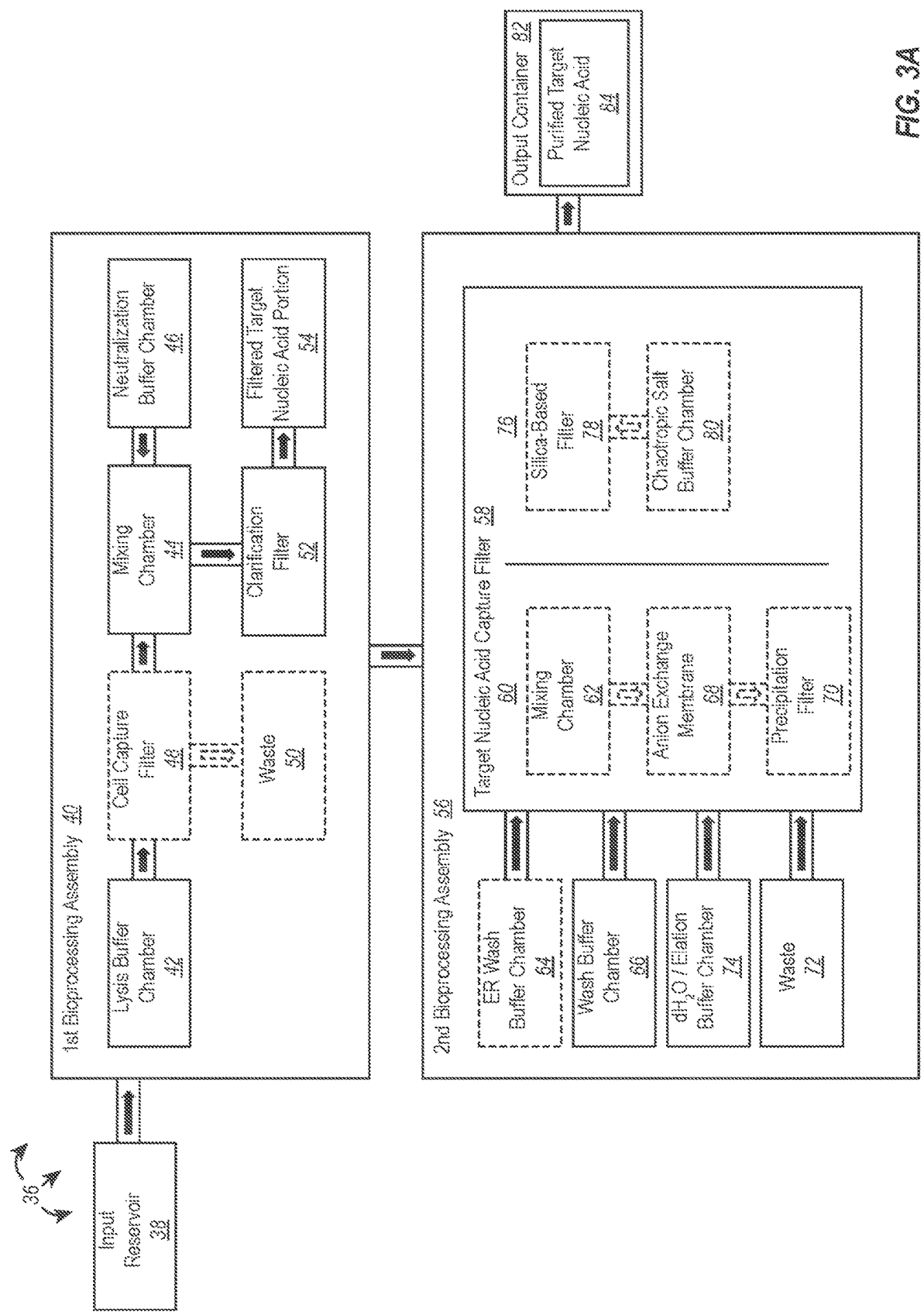
FIG. 3A illustrates various components of exemplary cartridges configured for use within a system for the automated purification of a target nucleic acid from a biological sample.

Referring now to FIG. 3A, various components of another exemplary cartridge 36 configured for use within a system for the automated purification of a target nucleic acid are illustrated. Similar to the cartridge 20 of FIG. 2, the cartridge 36 of FIG. 3A includes an input reservoir 38, a first bioprocessing assembly 40, a second bioprocessing assembly 56, various reagents and buffers (e.g., lysis buffer, neutralization buffer, RNAse A, resuspension buffer, IPA, ethanol, TE buffer, ER wash buffer, wash buffer, elution buffer, chaotropic salt buffer), and an output container 82. Although not shown, it should be appreciated that the cartridge 36 of FIG. 3A may additionally include a series of valves and pumps for coordinating movement of various fluids throughout the cartridge 36 during the automated purification process. As described above with respect to FIG. 2, the valves and pumps may be used to push and/or pull fluid through the cartridge, which some embodiments, can include a series of valves spatially configured upstream and downstream of a pump and filter/membrane such that operation of the pump can cause fluid to be pushed through the filter/membrane at one step in the purification process and pulled through the membrane at a different step in the purification process.

With continued reference to FIG. 3A, the illustrated cartridge 36 represents a collection of various exemplary cartridge configurations envisioned within the scope of this disclosure. It should be appreciated that the spatial configuration and flow between components illustrated within the cartridge 36 are not intended to be dispositive of the only way to structure and organize cartridges disclosed herein. Instead, the disclosed configurations are exemplary in nature and are intended to serve as schematics to aid in the description of possible representative configurations and components of cartridges envisioned within the scope of this disclosure. As shown in FIG. 3A, dashed boxes and arrows indicate potential additions or selections of components that may be used in exemplary cartridges disclosed herein. Some exemplary selections and configurations are provided within FIGS. 3B-3E to more particularly illustrate that which is disclosed in FIG. 3A.

In general, the various possible cartridge configurations broadly characterized in FIG. 3A and detailed within each of FIGS. 3B-3E follow a similar processing protocol. As shown in FIG. 3A, the first bioprocessing assembly 40 is fluidically coupled to the input reservoir 38. Through activation of a series of valves and pumps, a biological sample received within the input reservoir 38 can be transferred into and processed within the first bioprocessing assembly 40. It should be appreciated that in some embodiments, the input reservoir 38 is one component of the first bioprocessing assembly 40 and one or more purification steps performed within the first bioprocessing assembly 40 may be performed within or using the input reservoir 38. For example, an initial purification step may include homogenizing the biological sample. The biological sample may contain solid or particulate matter, and the purification process could benefit from the solid or particulate matter being reduced in size or more homogenously mixed within the supplied media and/or an applied aqueous buffer/solvent.

Accordingly, in some embodiments, the biological sample is homogenized within the input reservoir 38 and/or as a pre-processing step within the first bioprocessing assembly 40. This can be accomplished by any means known in the art, including for example, using a magnetic stir bar, high power bead beating, shaking, vortexing, or similar. For example, a stool or soil sample can be added to the input reservoir (concurrently with, or by subsequently adding, media and/or aqueous buffer/solvent) where the biological sample is homogenized and transferred to the first bioprocessing assembly. Additional, or alternative, homogenization steps can be implemented within the first bioprocessing assembly 40 and can be coupled with lysing of the cellular contents of the biological sample. The biological sample can be combined with lysis buffer housed within a lysis buffer chamber 42 to effect lysis of the cellular contents, and in some embodiments, a homogenization component is activated to homogenize the lysed sample.

Within the first bioprocessing assembly 40, target nucleic acid from the biological sample is partially purified from cellular content and waste media through the use of one or more filters/membranes. Generally, this includes the separation of the target nucleic acid after lysis and neutralization of cellular material. For example, lysis buffer held within the lysis buffer chamber 42 can be joined with the biological sample in a mixing chamber 44 to form a lysate. Neutralization buffer from the neutralization buffer chamber 46 can be combined, for example in the mixing chamber 44, with the lysate and passed through a clarification filter 52 to thereby separate a target-nucleic-acid-containing portion 54 of the biological sample from a waste portion of the biological sample.

As used herein, the term "filter" or "membrane" includes any size selection and/or charged semi-permeable barrier that is operable to select or separate one or more components from a solution. This can include, for example, a film or column of size selection filter paper or material. It can additionally include other forms or means of filtering, such as affinity columns, beads (e.g., steel, glass, zirconia, or other suitable material at any suitable size, preferably between 0.1-2 mm in diameter), or by other means known in the art.

The partially purified target nucleic acid can then be transferred to the fluidically coupled second bioprocessing assembly where the partially purified target nucleic acid is further purified and/or concentrated to be finally collected within an output container 82 as a purified target nucleic acid. The purification steps within the first and second bioprocessing assemblies can advantageously be accomplished with little to no user interaction.

The foregoing generalized purification process will now be described in greater detail in the context of the various exemplary cartridges, which are illustrated in FIGS. 3B-3E.

Figure 3B:
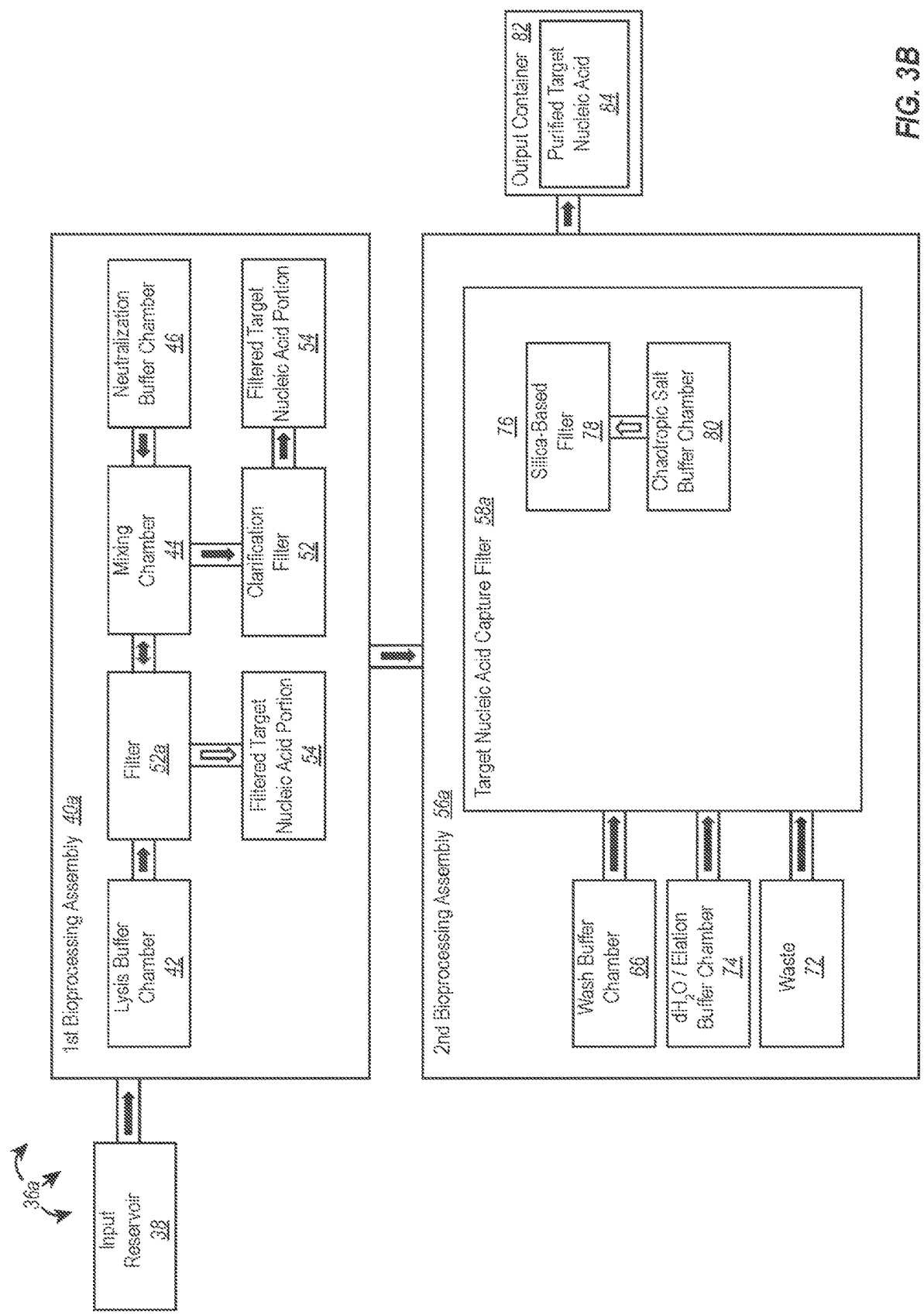
FIG. 3B illustrates one exemplary cartridge, based on the cartridge of FIG. 3A, configured with a single filter in each of the first and second bioprocessing assemblies.

One embodiment of a cartridge configured for use with a system for the automated purification of target nucleic acid from a biological sample is illustrated in FIG. 3B. The cartridge 36a is configured with a single filter in each of the first and second bioprocessing assemblies 40a, 56a. In particular, the first bioprocessing assembly 40a of the illustrated cartridge 36a includes a single filter 52a configured to filter a target-nucleic-acid-containing portion of the biological sample from cellular components and media. The filter can be, for example, a size selection filter having a selection size and material suitable for isolation of the particular target nucleic acid. A non-limiting example of the foregoing includes a 5 µm nylon filter.

During an exemplary implementation of the cartridge 36a of FIG. 3B, the biological sample can be passed from the input reservoir 38 and through the filter 52a of the first bioprocessing assembly 40a in a first step to remove media from the sample. In doing so, the cellular fraction of the biological sample is retained on the filter 52a. The cells associated with the filter 52a can be lysed using lysis buffer held within the lysis buffer chamber 42 of the cartridge 40a to form a lysate. It should be appreciated that the lysis buffer can elute the cells from the filter 52a by applying the cells to the cell capture side of the filter 52a. Alternatively, the lysis buffer can be pushed through the back side (e.g., the opposite side of the filter 52a elute the cells from the filter 52 can then is joined with the biological sample in a mixing chamber 44 to form a lysate. A neutralization buffer from the neutralization buffer chamber 46 can be combined, for example in the mixing chamber 44, with the lysate and passed through the filter 52a to thereby separate a target-nucleic-acid-containing portion 54 of the biological sample from a waste portion of the biological sample.

As further illustrated in FIG. 3B, the target-nucleic-acid-containing portion 54 of the biological sample can be transferred (e.g., using pumps and valves associated with the infrastructure of the cartridge 36a) to the second bioprocessing assembly 56a where it is bound to a single filter/membrane system 76. For example, the single filter/membrane system 76 can include a silica-based filter 78. In such an embodiment, the target-nucleic-acid-containing portion 54 of the lysate can be preprocessed with a chaotropic salt buffer that is automatedly obtained from a chaotropic salt buffer chamber 80 to promote binding of the target nucleic acid to the silica-based filter 78. Once bound to the silica-based filter 78, the target nucleic acid can undergo a series of washes via automated release and transfer of wash buffers from the wash buffer chamber 66 through the silica-based filter 78. The waste products from the aforementioned wash steps can be transferred to a waste reservoir 72. The washed target nucleic acid can be eluted from the silica-based filter 78 and into the output container 82 in the form of a purified target nucleic acid 84 using any appropriate low-salt elution buffer as known in the art.

In some embodiments, the first bioprocessing assembly can have more than one filter. For example, FIG. 3C illustrates another exemplary cartridge 36b that is configured with two filters 48, 52 in the first bioprocessing assembly 40b coupled to the same second bioprocessing assembly 56a (having a single filter) described above with respect to FIG. 3B.

Figure 3C:
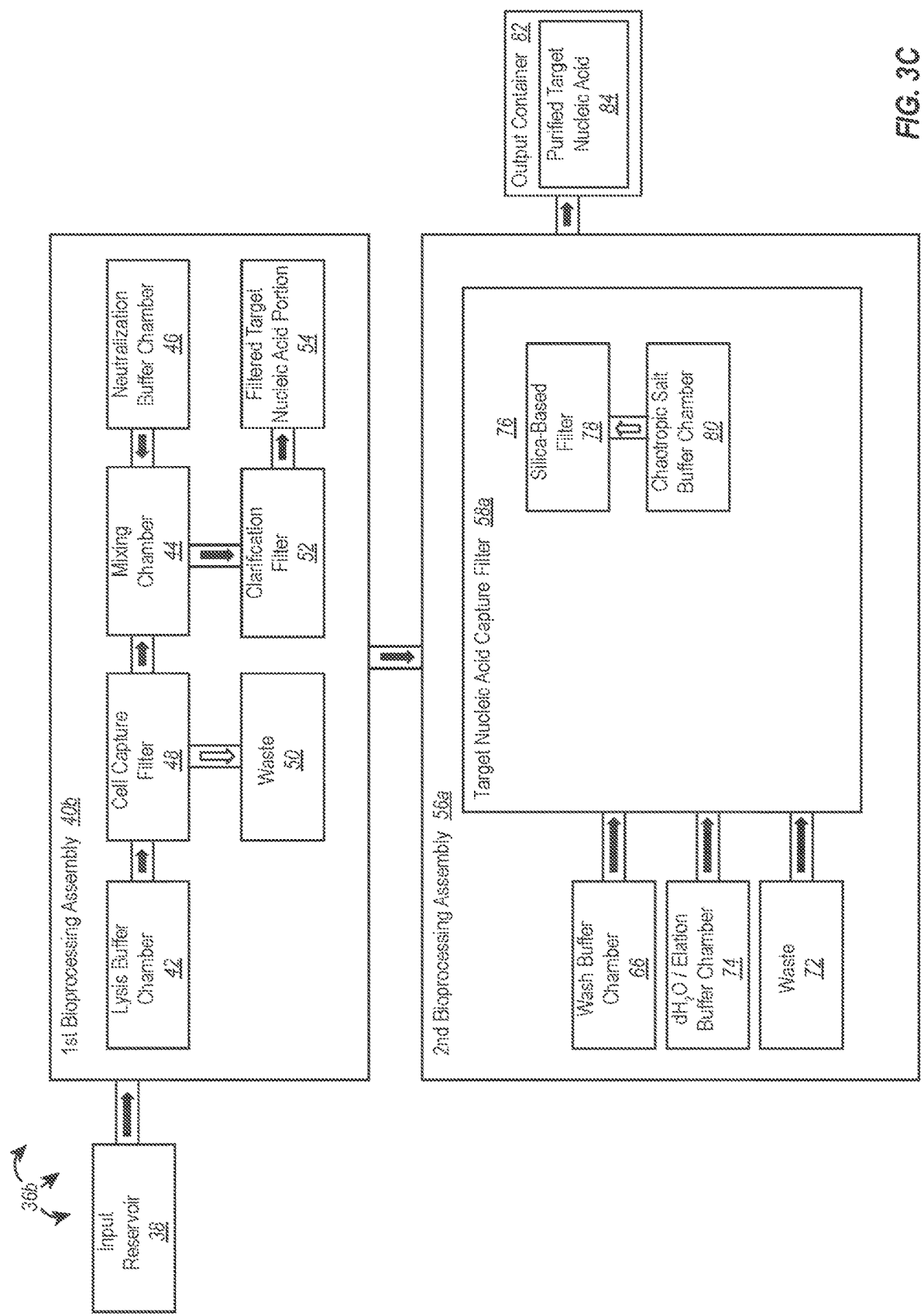
FIG. 3C illustrates another exemplary cartridge, based on the cartridge of FIG. 3A, configured with two filters in the first bioprocessing assembly and a single filter in the second bioprocessing assembly.

As shown in FIG. 3C, the first bioprocessing assembly 40b can additionally include a cell capture filter 48. The biological sample received at the first bioprocessing assembly 40b can be passed through the cell capture filter 48 to remove a non-target-nucleic-acid-containing portion of the biological sample. For example, in embodiments where the biological sample is a bacterial culture, the cell capture filter 48 can retain the bacterial cells at the cell capture filter 48 while allowing the culture supernatant to be passed to a waste reservoir 50. Lysis buffer and/or resuspension buffer from the lysis buffer chamber 54 can be passed over the cell capture filter 48 to remove and transfer the cells from the filter 48 to the mixing chamber 44 where a lysate is formed from the cell-containing solution. The neutralization buffer chamber 46 can be in fluid communication with the mixing chamber 44, and neutralization buffer can be subsequently transferred into the mixing chamber 44 where the lysate is neutralized. The neutralized lysate can then be passed through the clarification filter 52 to separate a target-nucleic-acid-containing portion 54 of the lysate from a waste portion of the lysate. In the running example of a bacterial culture, the foregoing waste portion of the lysate can include, among other things, cellular components of lysed bacterial cells, including bacterial genomic DNA.

It should be appreciated that although the biological sample is exemplified as a bacterial culture, this example is being used for the ease of illustrating the structural features of the disclosed cartridges. The biological sample can be other samples, such as a dirt sample, clinical or forensic sample (e.g., stool, blood, saliva, urine, etc.), water sample, or other sample having a target nucleic acid.

The first bioprocessing assembly 40b of cartridge 36b is fluidically coupled to the second bioprocessing assembly 56a, and as described above, the target-nucleic-acid-containing portion 54 of the biological sample can be transferred from the first bioprocessing assembly 40b to the second bioprocessing assembly 56a where it is bound to, washed, and eluted from the single filter/membrane system 76 as a purified target nucleic acid 84.

Figure 3D:
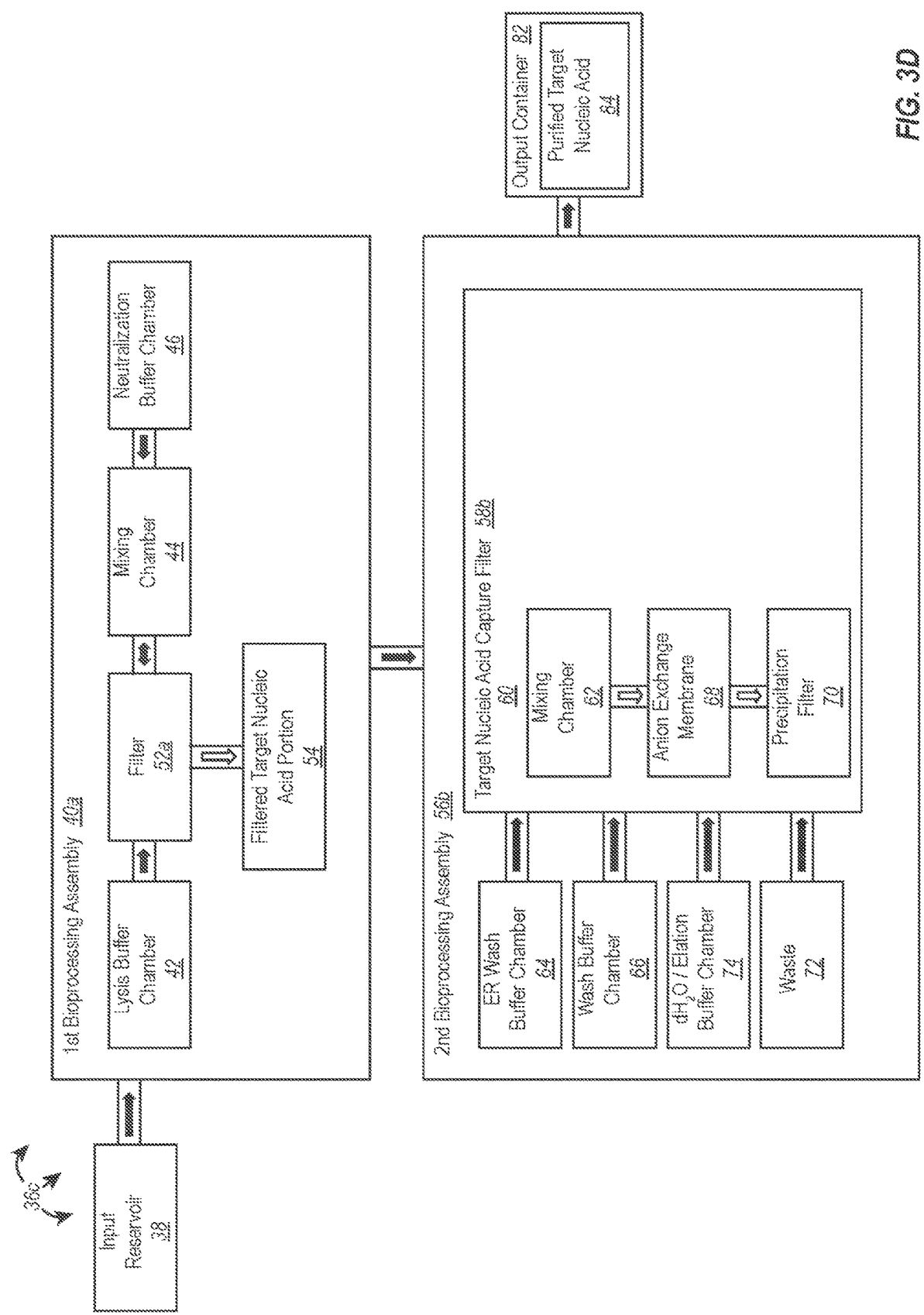
FIG. 3D illustrates yet another exemplary cartridge, based on the cartridge of FIG. 3A, configured with a single filter in the first bioprocessing assembly and two filters in the second bioprocessing assembly.

FIG. 3D illustrates yet another exemplary cartridge 36c. The illustrated cartridge 36c is configured with a single filter 52a in the first bioprocessing assembly 40a (similar to that illustrated and discussed in FIG. 3B) and two filters in the second bioprocessing assembly 58b. The target-nucleic-acid-containing portion 54 of the lysate is bound to a target nucleic acid capture filter 58b within the second bioprocessing assembly 56b. Prior to binding to the filter 58b, the target-nucleic-acid-containing portion 54 of the lysate can be optionally preprocessed with an endotoxin removal (ER) buffer (e.g., from the ER wash buffer chamber 64) in a "low-endotoxin" or "endotoxin free" purification protocol. Once bound to the target nucleic acid capture filter 58b, target nucleic acid is washed and eluted into the output container 82 in the form of a purified target nucleic acid 84. Washing the target nucleic acid bound to the capture filter 58 can include, for example, passing various wash buffers or aqueous solutions containing isopropyl alcohol or ethanol through the capture filter 58b and into a waste reservoir 72. These wash buffers are automated of the released from one or more wash buffer chamber 66 that are in fluid communication with the capture filter 58b. In a similar fashion, the washed target nucleic acid can be eluted from the capture filter 58b through the automated release of, for example, distilled water or in elution buffer obtained from the dH₂O/elution buffer chamber 74 fluidically coupled to the capture filter 58b.

As shown in FIG. 3D, the capture filter 58b can include a series of filters/membranes 60. The target-nucleic-acid-containing portion 54 of the lysate can be bound and washed along the series of filters/membranes 60 before being eluted into the output container 82. In some embodiments, the target-nucleic-acid-containing portion 54 of the lysate can be preprocessed with a wash buffer prior to binding the series of filter/membranes 60. The wash buffer can be automatedly released from wash buffer chamber 66 and into a mixing chamber 62 to mix with the target-nucleic-acid-containing portion 54 of the lysate. The preprocessed target nucleic acid can then be bound to an anion exchange membrane 68 where additional washing steps can be performed by automatedly passing wash buffers (e.g., from one or more different wash buffer chamber 66) over the anion exchange membrane 68. The target nucleic acid can then be eluted from the anion exchange membrane 68 and bound to a precipitation filter 70 for additional washing and purification steps.

In some embodiments, the target nucleic acid is eluted from the anion exchange membrane 68 and transferred to a mixing chamber where the target nucleic acid is mixed with isopropanol and precipitated from solution. The precipitated target nucleic acid is then transferred and bound to the precipitation filter 70 where it is desalted via a number of ethanol-based (e.g., 70% ethanol) washes prior to elution into the output container 82.

Figure 3E:
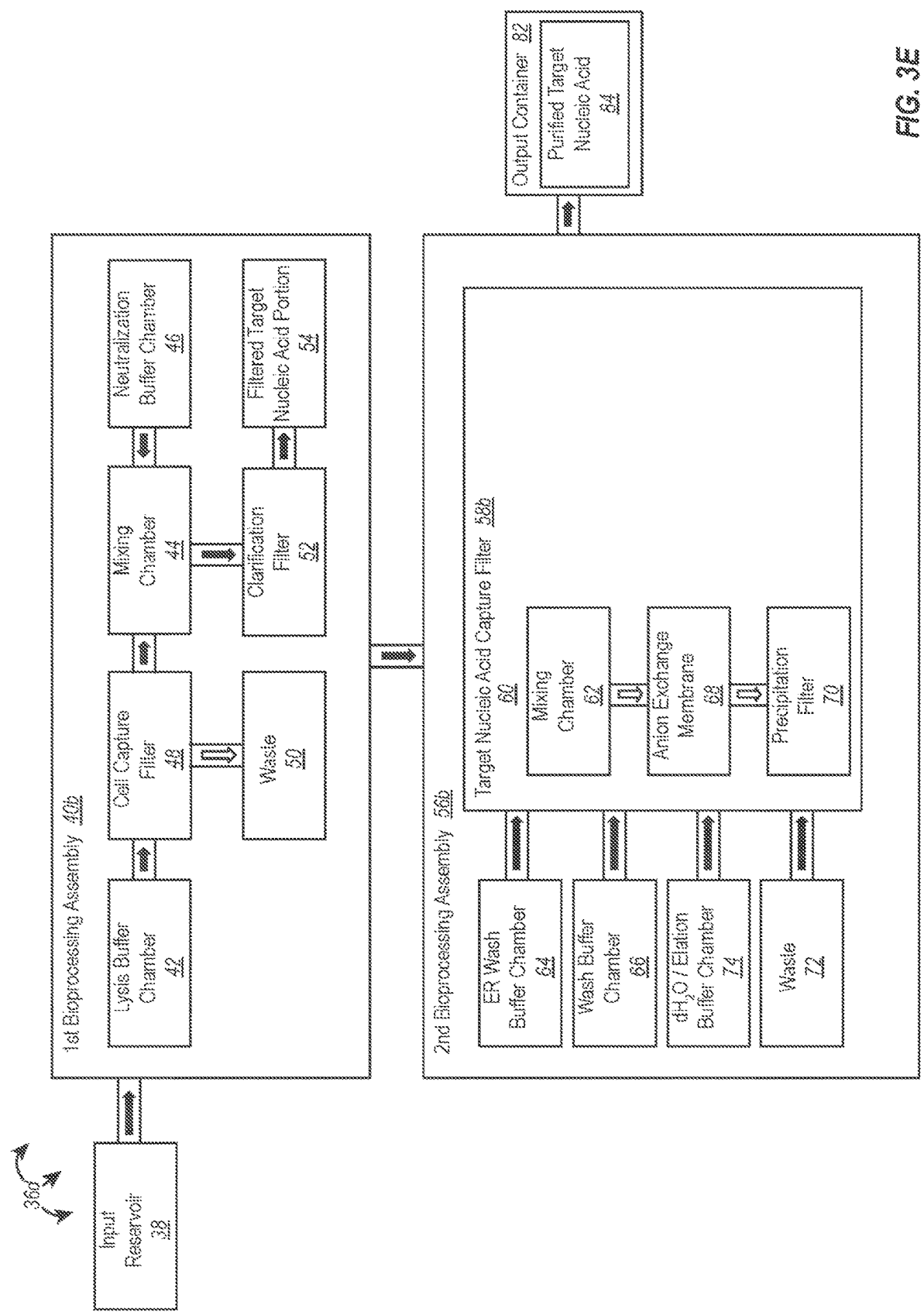
FIG. 3E illustrates still another exemplary cartridge, based on the cartridge of FIG. 3A, configured with two filter in each of the first and second bioprocessing assemblies.

FIG. 3E illustrates still another exemplary cartridge 36d. The cartridge 36d is configured with two filter in each of the first and second bioprocessing assemblies 40b, 36b. For example, the first bioprocessing assembly 40b can include the same first bioprocessing assembly 40b of cartridge 36b described and shown in FIG. 3C, and the second bioprocessing assembly 56b can include the same second bioprocessing assembly 56b of cartridge 36c described and shown in FIG. 3D.

Accordingly, cartridges for use in the automated purification of nucleic acid from a biological sample can include two or more bioprocessing assemblies that are each associated with at least one filter/membrane. In some embodiments, a first bioprocessing assembly can include a single clarification filter, or alternatively, the first bioprocessing assembly can include a cell capture filter and a clarification filter. Similarly, the second bioprocessing assembly can include a single silica-based filter, or alternatively, the second bioprocessing assembly can include a precipitator membrane disposed downstream of the anion exchange membrane. Stated another way, the second bioprocessing assembly can include an anion exchange membrane, and the cartridge can additionally include a third bioprocessing assembly that includes a precipitation filter for receiving the eluted target nucleic acid from the anion exchange membrane.

Sample Processing through an Exemplary Purification Cartridge

Figure 4:
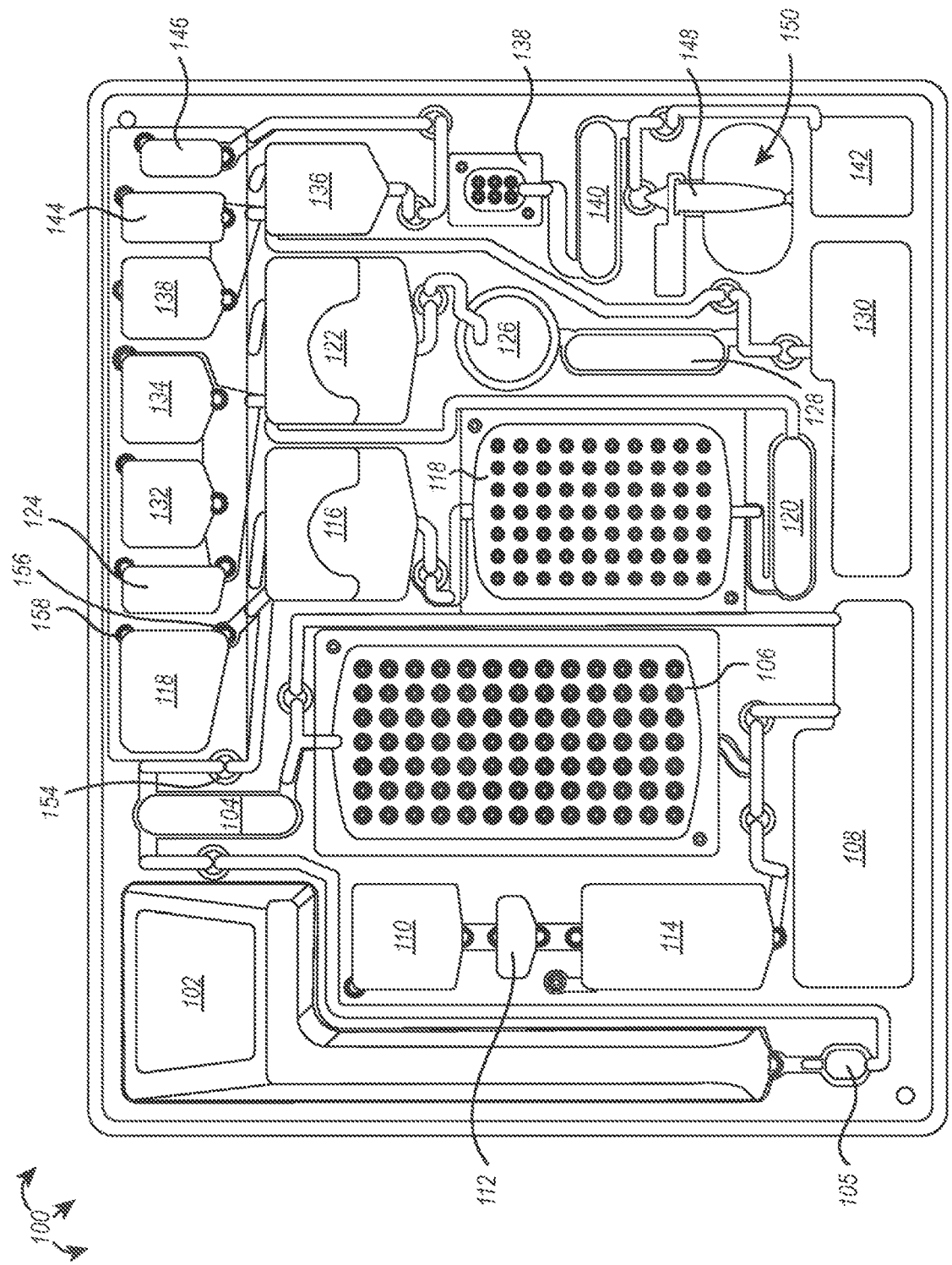
FIG. 4 illustrates an exemplary layout of a purification cartridge for the automated purification of a target nucleic acid from a biological sample, including an input reservoir, various bioprocessing assemblies and associated membranes, filters, mixing chambers, buffer/reagent reservoirs, pumps, valves, conduits, and output container for receiving the target nucleic acid of the input biological sample in purified form.

The cartridges shown and described in FIGS. 2 and 3 can be specifically embodied as the exemplary cartridge 100 of FIG. 4. In particular, FIG. 4 illustrates a partial cross-sectional view of the various bioprocessing assemblies, filters/membranes, buffer/reagent reservoirs, fluidic conduits, valves (e.g., valve 154, among others; also shown as numbered "V" elements in FIGS. 5A-5K), seals (e.g., seal 156 and seal 158, among others; also shown as numbered "L" elements in FIGS. 5A-5K), waste reservoirs, and output container associated with the illustrated cartridge 100. Each of the various components of the cartridge 100 illustrated in FIG. 4 will be discussed in the context of an exemplary automated nucleic acid purification process shown stepwise in FIGS. 5A-5K. It should be appreciated that the mechanisms for sealing and releasing fluids throughout the automated nucleic acid purification process described with reference to FIGS. 5A-5K are discussed in more detail below.

In an exemplary embodiment, the cartridge 100 of FIGS. 5A-5K can be used in conjunction with a purification instrument described herein to provide an automated "hands-off" bioprocessing of biological samples while delivering performance that is at least as good, if not better than, similar manual processing methods. As alluded to above, the scientist or lab technician that is tied to the bench while performing the manual nucleic acid purification protocol of biological samples introduces human error and a lack of reproducibility. When used as a part of an automated nucleic acid purification system, cartridge 100 (and other cartridges disclosed herein) can eliminate or reduce the human error in lack of reproducibility plaguing the manual nucleic acid purification processes. Additionally, the cartridges provided herein can increase convenience of use, reduce labor time, reduce contamination, and increase the efficiency and flexibility of performing nucleic acid isolation and purification protocols.

Figure 5B:
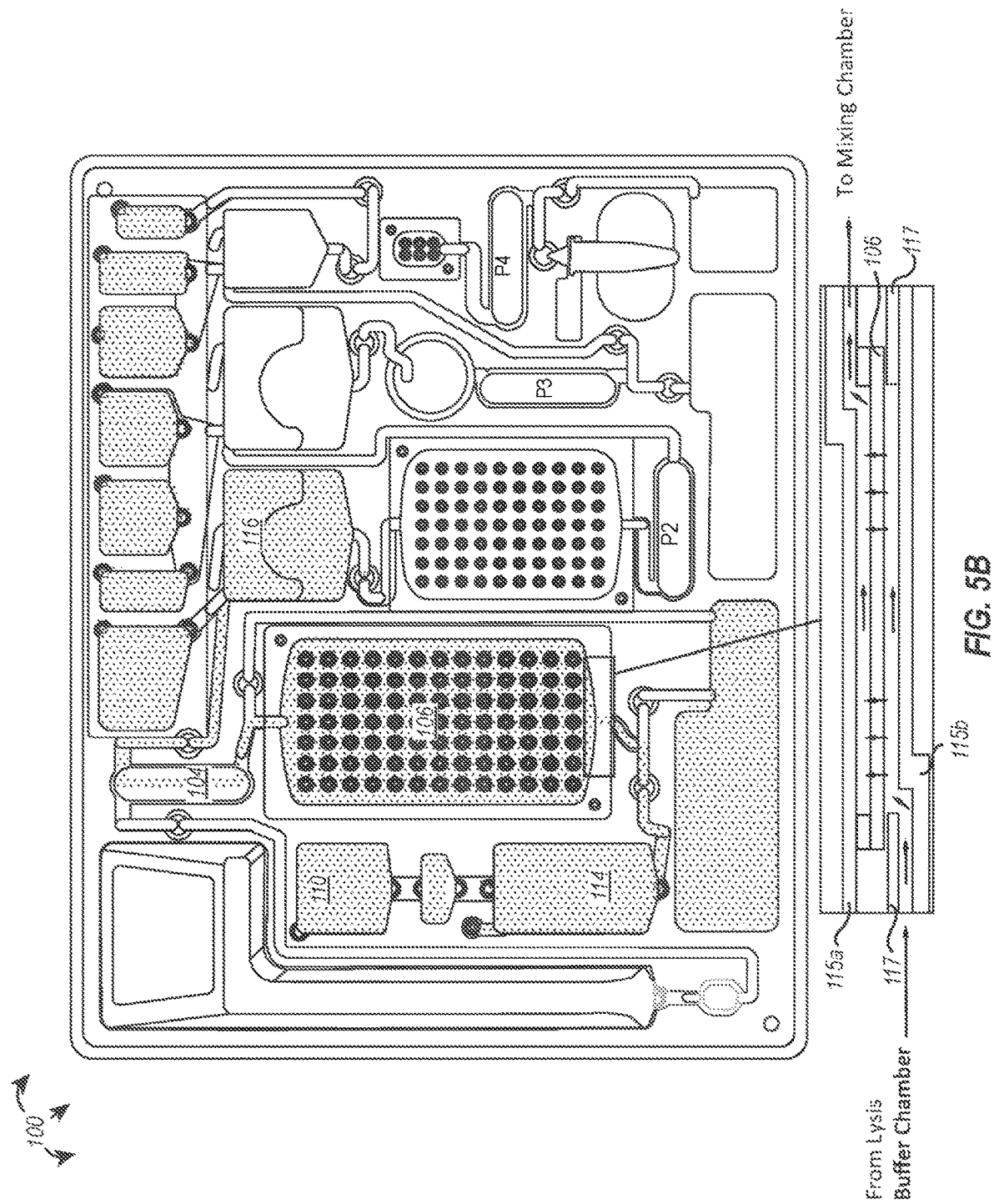

For example, with reference to FIG. 5A, a biological sample, such as a bacterial culture or other cell culture containing plasmid DNA, can be added to the culture reservoir 102 by a technician, scientist, or other user. The cartridge 100 can be inserted into a purification instrument where a nucleic acid purification protocol is initiated. The following steps discussed with respect to FIGS. 5A-5K can be performed without further human interaction in an automated process. For the ease of illustration and description, the components and processing steps in FIGS. 5A-5K will be made with reference a bacterial culture as the biological sample and plasmid DNA as the target nucleic acid. It should be appreciated that other biological samples and target nucleic acids can be processed using the automated nucleic acid purification systems, methods, devices disclosed herein and are included within the scope of the disclosure. It should additionally be appreciated that within the disclosed embodiment of FIGS. 4 and 5A-5K, each of the buffers and reagents discussed and used in the exemplary nucleic acid purification protocol are contained within the cartridge 100. Similarly, each of the filters/membranes discussed and used in the forthcoming exemplary nucleic acid purification protocol are contained within the cartridge 100. The release, sealing, and movement of fluids within the cartridge can be generally controlled and/or initiated by the purification instrument, as described in greater detail below.

With continued reference to FIG. 5A, the bacterial culture containing plasmid DNA is present within the culture reservoir 102. In some embodiments, air can be pumped through the culture reservoir 102 to disperse any settled cells and/or to homogenize the culture prior to release from the culture reservoir 102. This can be particularly advantageous in embodiments where, following release from the culture reservoir 102, the optical density (e.g., A600) of the culture is measured at an optical density window 105 because a more accurate reading can be obtained from a homogenous culture. The optical density of the culture can be, for example, reported to the user and/or used by the instrument to indicate an anticipated low yield due to insufficient input material (low OD) or to indicate low yield due to an overburdened system (high OD).

Regardless of whether an optical density measurement is taken, the culture reservoir 102 is opened (e.g., by puncturing a frangible seal between the culture reservoir and fluidic channel), and the contents of the culture reservoir 102 are pumped (e.g., via pump 104) through a fluidic channel within the cartridge 100 to a cell capture filter 106. At the cell capture filter 106, the culture media within the biological sample is passed through the filter 106 and into a waste reservoir 108. The plasmid DNA containing bacterial cells within the biological sample are retained at the cell capture filter 106. In some embodiments, the cell capture filter 106 can be a size selection filter having a pore gradient between 0.65 μm-1.2 μm (e.g., a 7.5 mil thick nylon cell capture filter). Additionally, in some embodiments the cell capture filter should desirably withstand pressures greater than 20 psi, greater than 30 psi, greater than 40 psi, or greater than 60 psi without leaking as the build-up of cells on one side of the filter can lead to low flow conditions and increase the pressure on the filter. In some embodiments, a compliant support gasket (e.g., an elastomer layer localized to the cell capture filter) can be added around the perimeter of the filter opposite the resident elastomer layer between the external layers of the cartridge to provide a better sealing interface between the cartridge and the instrument.

As shown in the simplified cross-sectional schematic of the cell capture filter 106 of FIG. 5A (support gasket shown as element 107), the filter 106 is sandwiched between external layers 115a, 115b of the cartridge 100. The biological sample can be pulled from the culture reservoir 102 and between a first external layer 115a and a first side of the filter 106. Suction or pumping action from the pump 104 causes the culture media within the biological sample to pass through the filter 106 and into a space provided between a second side of the filter 106 and the second external layer 115b. The culture media is then directed along a fluidic conduit and through an open valve to the waste reservoir 108.

As shown in FIG. 5B, RNase A can be passively mixed with resuspension buffer and lysis buffer by piercing frangible seals separating the resuspension buffer reservoir 110 from the RNase A reservoir 112 and the lysis buffer reservoir 114. In some embodiments, the lysis buffer reservoir 114 may have a larger volume overhead to accommodate the volumes of RNase A and resuspension buffer and gravity flow from the resuspension buffer reservoir 110 through the RNase A reservoir 112 and into the lysis buffer reservoir 114 can allow for the passive mixing of these buffers and reagents in the lysis buffer reservoir 114 to create a combined resuspension/lysis buffer.

As shown in the inset cross-sectional schematic of the cell capture filter 106 of FIG. 5B, the combined resuspension/lysis buffer solution can be backwashed over the filter 106 to recapture the cells from the filter 106, entrain them within the resuspension/lysis buffer solution, and transfer the cell-containing solution to a first active mixing chamber 116. As shown in FIG. 5B, the pump 104 can be reversed to allow for backwashing over the filter 106 and transferring to the active mixing chamber 116.

Figure 5C:
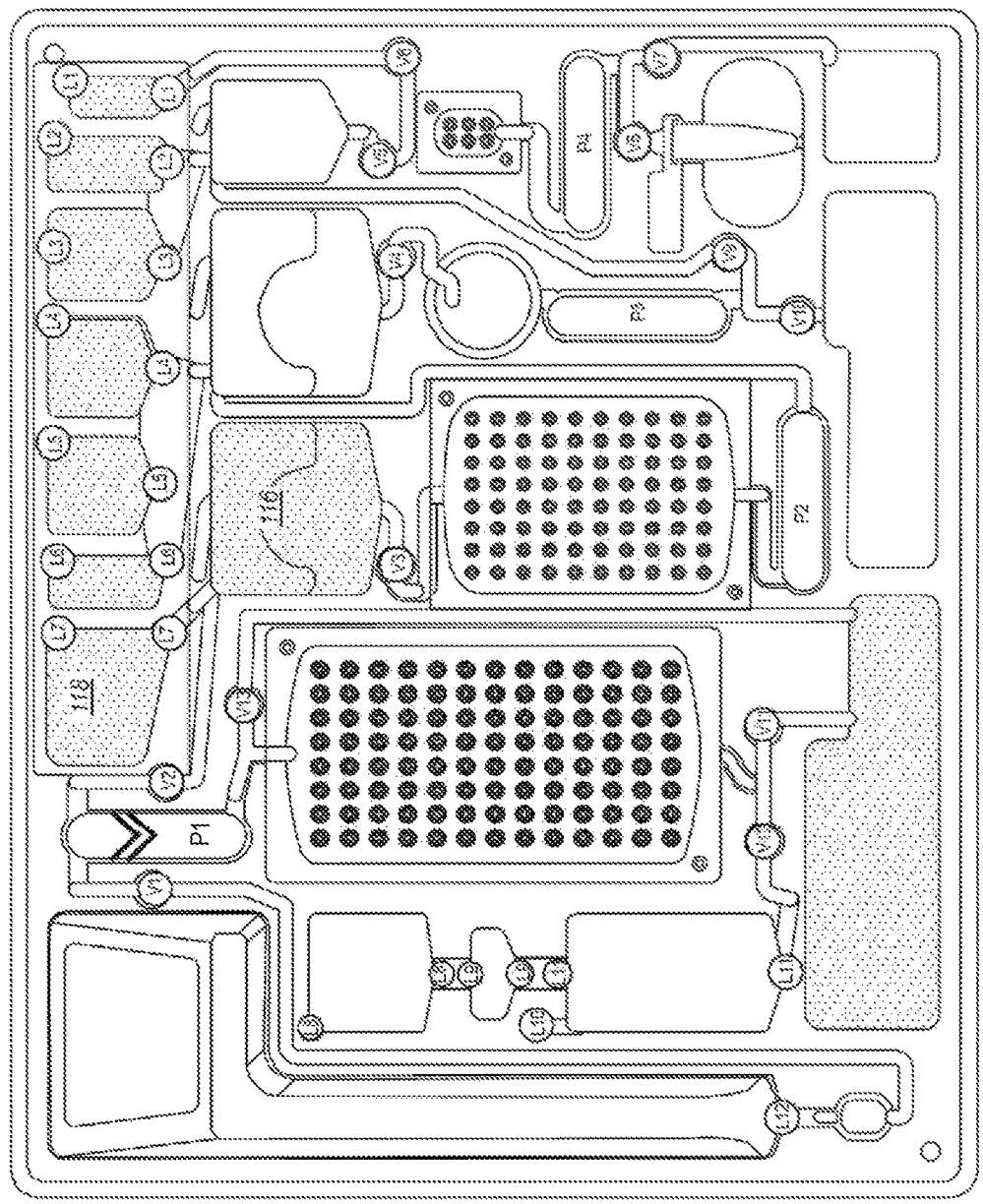

As shown in FIG. 5C, the cells within the resuspension/lysis buffer solution can be lysed under active mixing in the mix chamber 116. As with other active mixing chambers discussed below, the first active mixing chamber 116 can include a magnetic stir bar (or other means of agitating and/or mixing the solution within the chamber 116) that is operable by the purification instrument to actively mixed contents of the mixing chamber 116. In some embodiments, the magnetic stir bar can agitate the mixture up to or greater than 1,000 rpm.

Following formation of the cellular lysate within the mixing chamber 116, neutralization buffer can be automatedly released from the neutralization buffer reservoir 118 and into the mixing chamber 116 (e.g., by piercing frangible seals associated with the neutralization buffer reservoir 118 and allowing passive transfer from the neutralization buffer reservoir 118 to the mixture chamber 116). Actively mixing the neutralization buffer with the lysate can bring the lysate pH back to normal, leading to precipitation of protein from the lysate and renaturing of the genetic material. Because of its circular nature, plasmid DNA can renature properly and remain soluble, whereas genomic DNA crashes out of solution due to random association of strands. The precipitated cell debris and tied genomic DNA becomes insoluble within the solution and consequently separable therefrom.

Figure 5D:
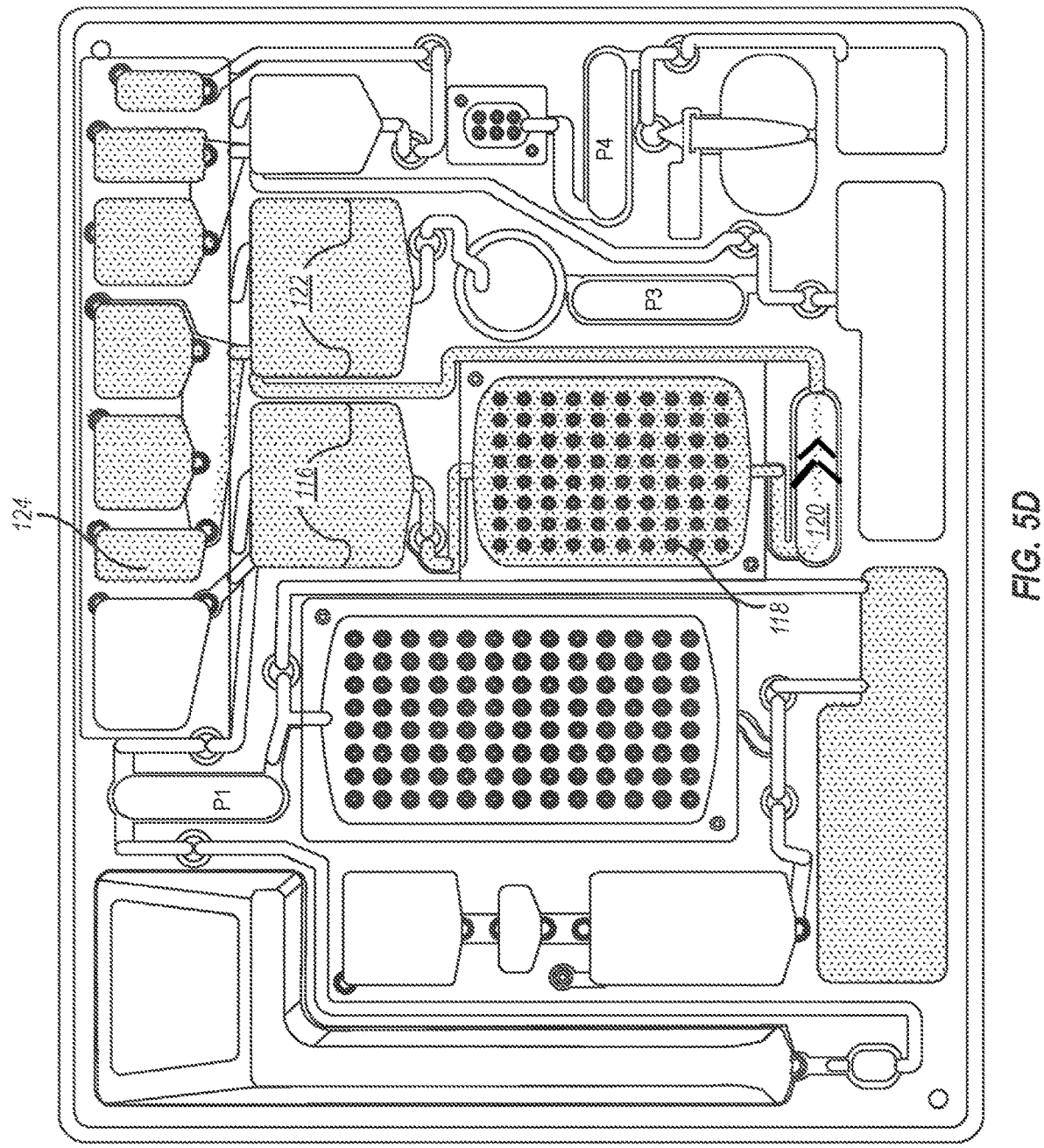

Referring now to FIG. 5D, smaller volume ER buffer can be pre-released from the ER buffer reservoir 124 into a second active mixing chamber 122 to improve later contact with subsequent fluids. At the same time or within a short duration before or after release of the ER buffer, the neutralized lysate can be passed through a clarification filter 118. The clarified lysate (i.e., the target-nucleic-acid-containing portion of lysate) is pulled through the clarification filter 118 and pumped into the second active mixing chamber 122 by pump 120. The waste-containing portion of the neutralized lysate remains bound within the clarification filter 118.

In some embodiments, the clarification filter can be prone to collapsing on itself and closing off its porous structure during flow, thereby preventing the filter from performing its desired function. To prevent this, some embodiments may include a thin semi-rigid, porous backing structure in place of a perimeter support gasket to provide support across the extent of the clarification filter and to prevent the clarification filter from collapsing during flow, thereby allowing the filter to perform its desired function. The clarification filter can be any clarification filter known or used in the art that is suitable for separating the waste-containing portion of the neutralized lysate from the nucleic-acid-containing portion of the neutralized lysate. For example, the clarification filter can include a glass-fiber-based filter with a pore size greater than about 1 μm and/or less than about 5 μm and that is greater than 30-mil thick. For example, a clarification filter used within cartridges of the present disclosure can include a Glass Fiber A filter having a 4.3 μm pore size and 45-mil thickness or a glass fiber filter having a 1 μm pore size in a thickness ranging between 43-mil-53-mil. The glass-fiber-based clarification filters can be paired with any suitable semi-rigid clarification support, such as, for example, a 1/16" thick polyethylene clarification support filter having a pore size greater than 15 μm (e.g., between 15 to 45 μm pore size).

After the clarified lysate is pulled through the clarification filter 118 and pumped into the second active mixing chamber 122, it is actively mixed therein with the ER buffer. The clarified lysate/ER buffer solution can be actively mixed within the second active mixing chamber 122 using a magnetic stir bar—as provided above with respect to the first active mixing chamber 116 or the like—to remove contaminants from the clarified lysate for increased sample purity.

Figure 5E:
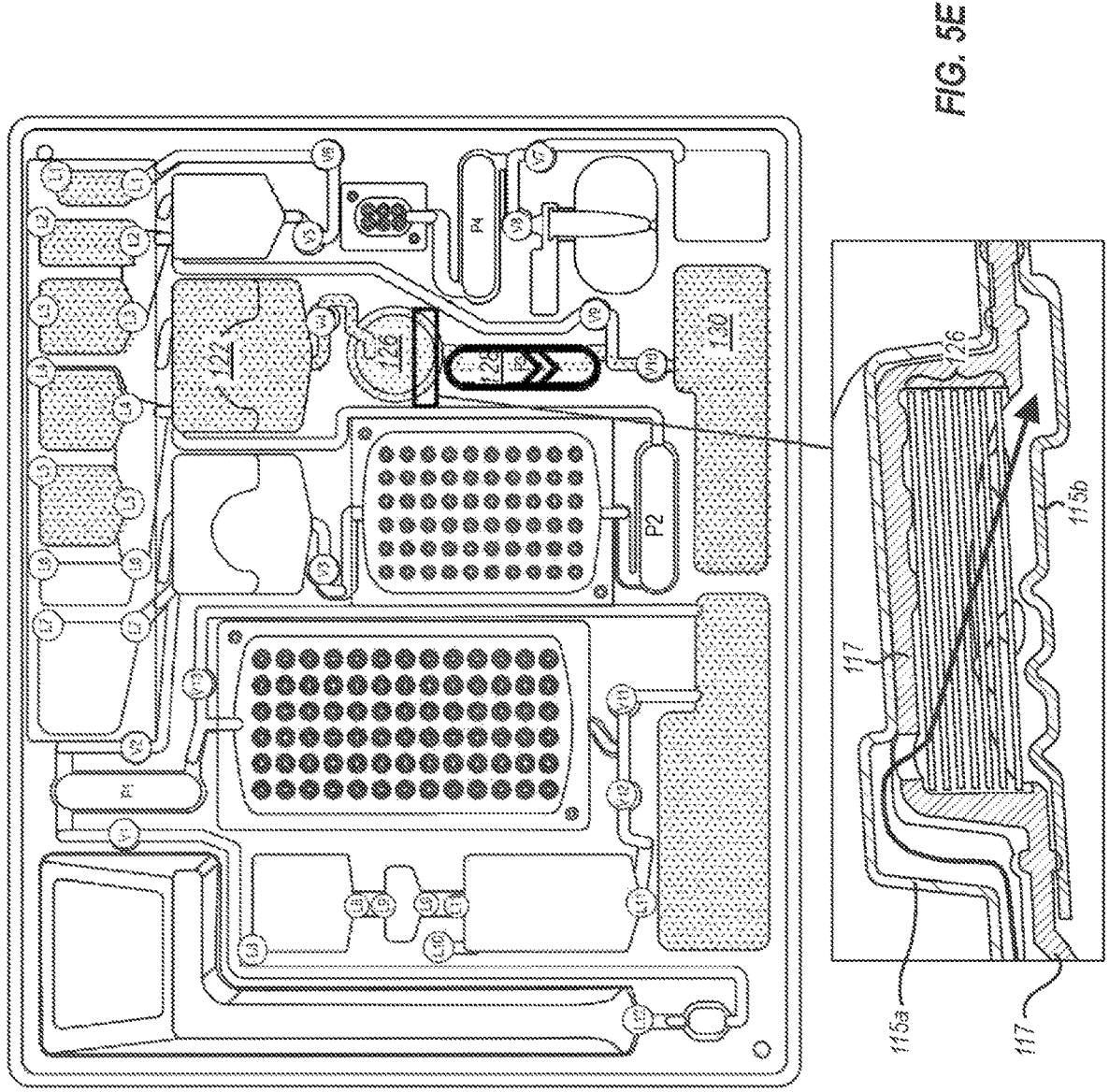

Referring now to FIG. 5E, the clarified lysate is pumped from the second active mixing chamber 122 and through an anion exchange membrane structure 126 via pump 128. The plasmid DNA within the clarified lysate is bound to the anion exchange membrane structure 126 due to favorable ionic interactions with the charged column, and the waste-containing portion (i.e., the non-target-nucleic-acid containing portion) of the clarified lysate passes through the anion exchange membrane structure 126 and is deposited within the waste reservoir 130.

As shown in the inset cross-sectional schematic of FIG. 5E, the anion exchange membrane 126 is structured in an attempt to create an axial flow through a stack of anion exchange membranes. As shown in the exemplary cross-sectional schematic, a near-vertical wall approximately 9 mm tall is created by the intermediate layer 117 and a first external layer 115a on the inlet side. An aperture formed by the intermediate layer creates an inlet from the fluid channel formed by the external and intermediate layers of the cartridge and into the housing that holds a stack of anion exchange membranes 126. As the fluid is pulled through the membrane stack 126, the membranes can ionically capture the plasmid DNA while allowing waste portions to pass through the filter stack 126 and into the waste reservoir 130. It should be appreciated that an axial flow through the anion exchange membrane 126 can be made in different ways or by using different heights of stacked membranes.

In some embodiments, the anion exchange membrane is a silicone treated glass fiber membrane. The glass-fiber-based anion exchange membranes can be paired with any suitable semi-rigid support, such as, for example, a 1/16" thick polyethylene support filter having a pore size greater than 15 μm (e.g., between 15 to 45 μm pore size).

Figure 5F:
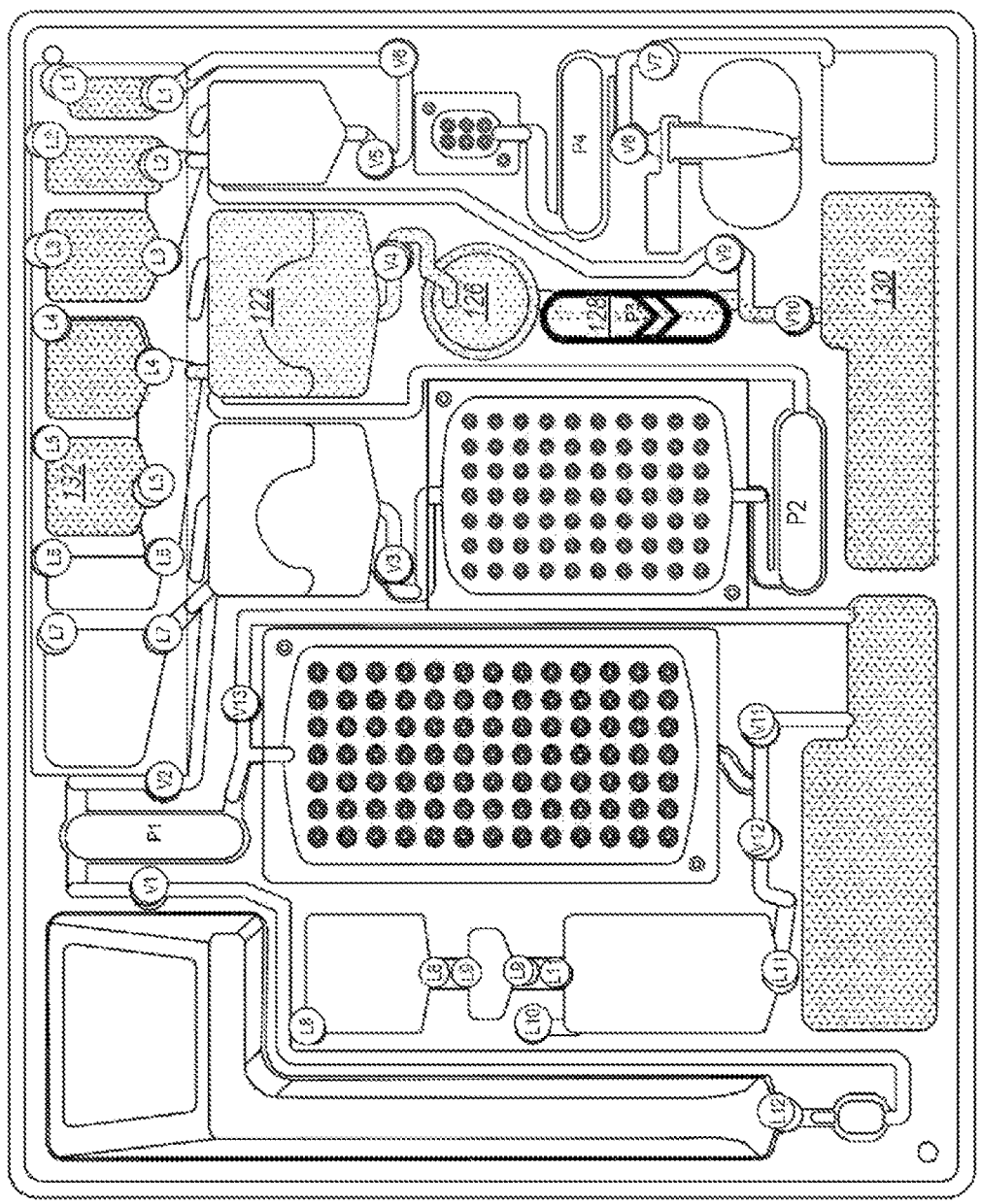

After passing the neutralized lysate through the anion exchange membrane 126, wash buffer from the wash buffer reservoir 132 is automatically released and pulled through the anion exchange membrane structure 126 via the pump 128, as shown in FIG. 5F. Any wash liquid that passes through the anion exchange membrane 126 is collected within waste reservoir 130. In a preferred embodiment, the wash solution is selected so as not to interfere with membrane-bound plasmid DNA and acts to remove superfluous substances from association with the plasmid DNA and/or the filter 126.

Figure 5G:
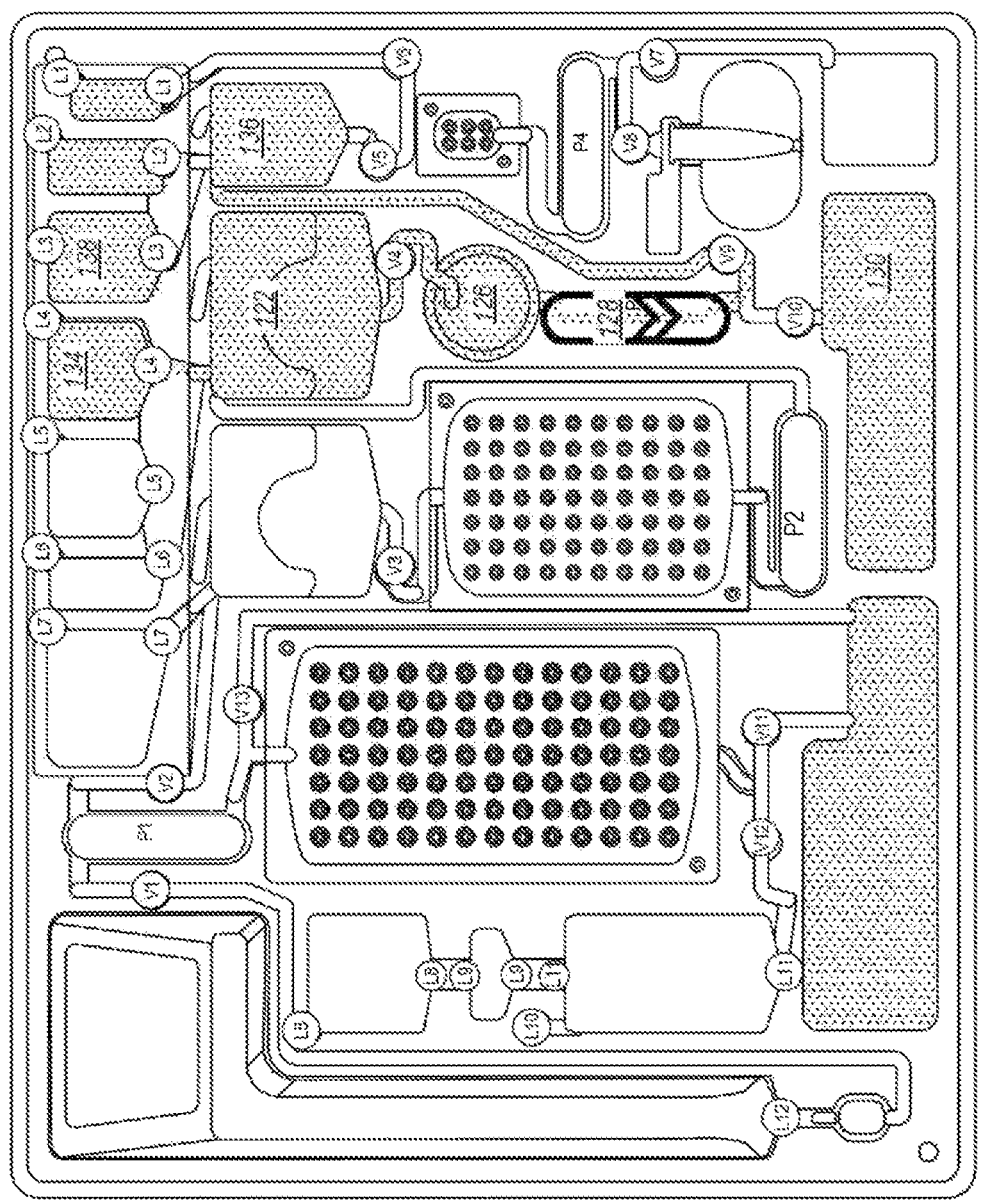

Referring now to FIG. 5G, isopropanol can be automatedly released from the isopropanol reservoir 138 and into a third active mixing chamber 136 to improve contact with subsequent fluids. At the same time or within a short duration before or after release of the isopropanol, elution buffer can be automatedly released from the elution buffer reservoir 134 and through the anion exchange membrane structure 126 via pump 128. The elution buffer can provide a more favorable chemical interaction with the plasmid DNA than the anion exchange membranes, which causes the plasmid DNA to disengage from the membranes and elute into the passing elution buffer. This eluent is pumped through the anion exchange membrane structure 126 and into the third active mixing chamber 136. Within the third active mixing chamber 136, the eluent, consisting of the elution buffer and plasmid DNA, mixes with isopropanol, and the plasmid DNA, along with several salts, precipitate from the elution buffer solution.

Figure 5H:
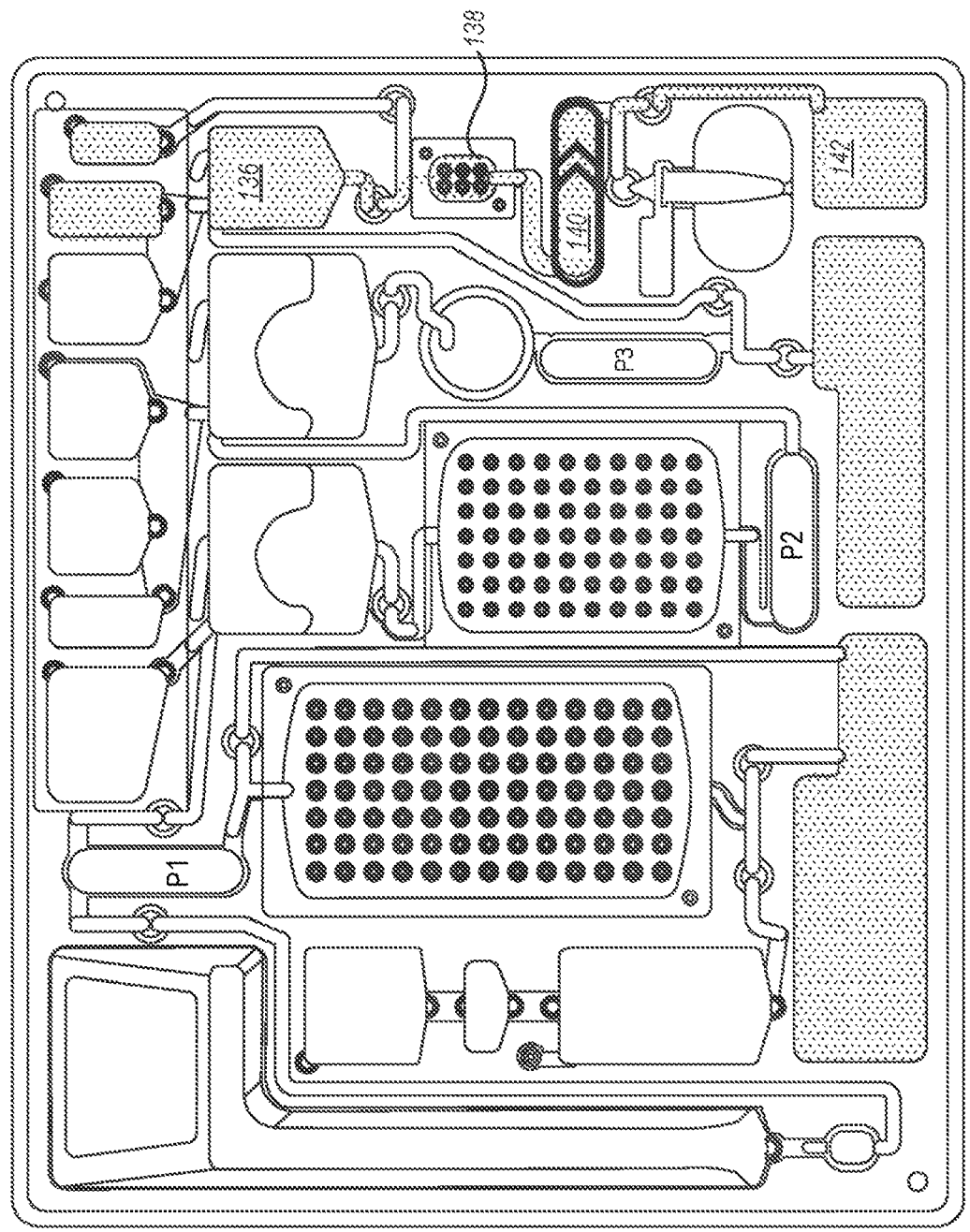

The precipitation mixture formed within the third active mixing chamber 136 is subsequently passed over precipitator membrane 138, as shown in FIG. 5H. The plasmid DNA within the precipitation mixture becomes bound within the precipitator membrane (e.g., based on pore size of the precipitator membrane), and smaller soluble components as well as the elution buffer as through the precipitator membrane and are collected within waste reservoir 142. In some embodiments, the precipitator membrane as a pore size greater than equal to 1 μm and can be made of or include glass fiber. For example, a precipitator filter can include a glass fiber filter with 1 μm pore size or a 16-mil thick Glass Fiber D filter.

In some embodiments, the precipitator filter may not be subjected to the same or similarly high pressures as the cell capture filter, but to ensure that little or essentially no fluid wicks out to inactive areas of the precipitator filter, a perimeter seal can be associated with the precipitator filter. For example, an O-ring (or other functionally similar gasket) can be positioned between the external layers of the cartridge and on an opposite side of the precipitator filter as the intermediate layer of the cartridge.

Figure 5I:
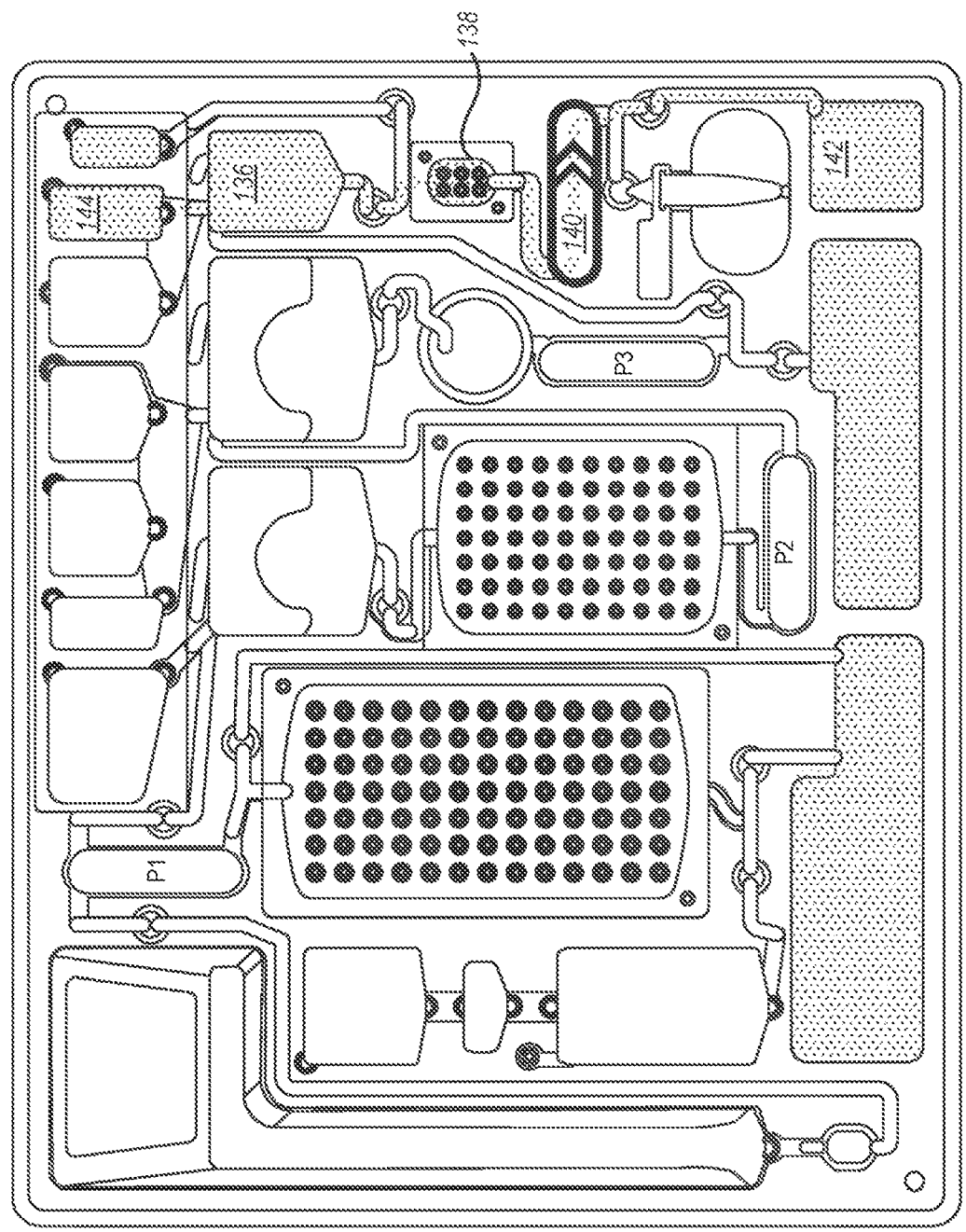

The precipitator membrane 138 can be washed with ethanol-based solutions to solubilized and remove salts (i.e., desalt) the plasmid DNA. As shown in FIG. 5I, a 70% ethanol solution can be automatedly released from an ethanol reservoir 144 and pulled through the precipitator membrane 138 via pump 140. The ethanol wash can pass through the precipitator membrane 138 along with any solubilized salts and past into waste reservoir 142.

Figure 5J:
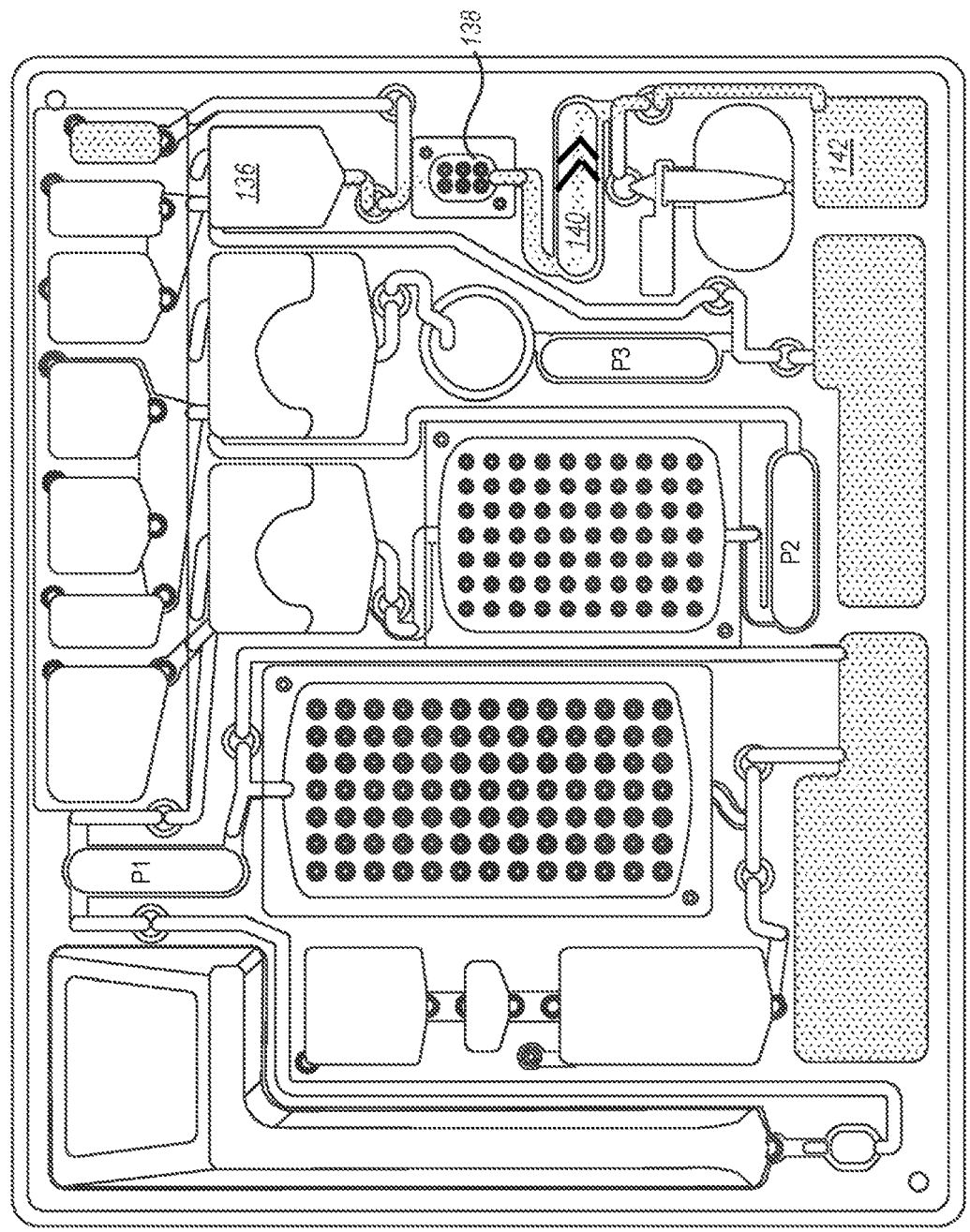

Referring now to FIG. 5J, the pump 140 can continue to operate after the ethanol wash has passed through the precipitator filter 138. This can cause air to move over the precipitator filter 138 drying the plasmid DNA and causing evaporation of excess fluids (especially alcohols).

Figure 5K:
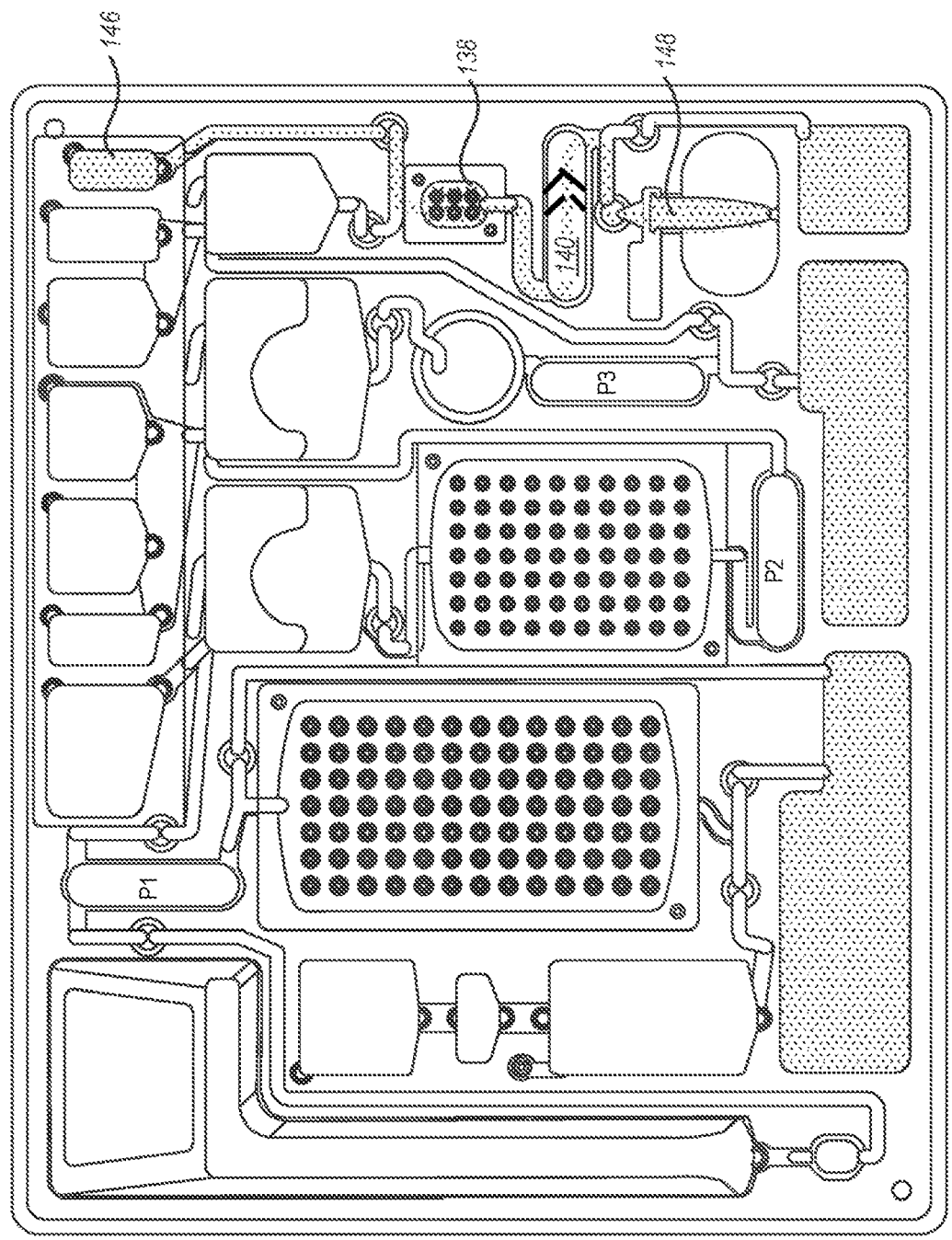

The washed and dried plasmid DNA can be eluted from the precipitator membrane 138 and transferred to an output container 148, as shown in FIG. 5K. During this final process, TE buffer can be automatedly released from a TE buffer reservoir 146 and pulled over precipitator membrane 138 via the continued action of pump 140 where the plasmid DNA is eluted from the precipitator membrane 138 and into the passing TE buffer. By closing and opening different valves within the cartridge 100, the eluted plasmid DNA can be routed from the precipitator membrane 138 into the output container 148 instead of into the waste reservoir 142 like the previous fluids passing through the precipitator membrane 138.

Figure 6:
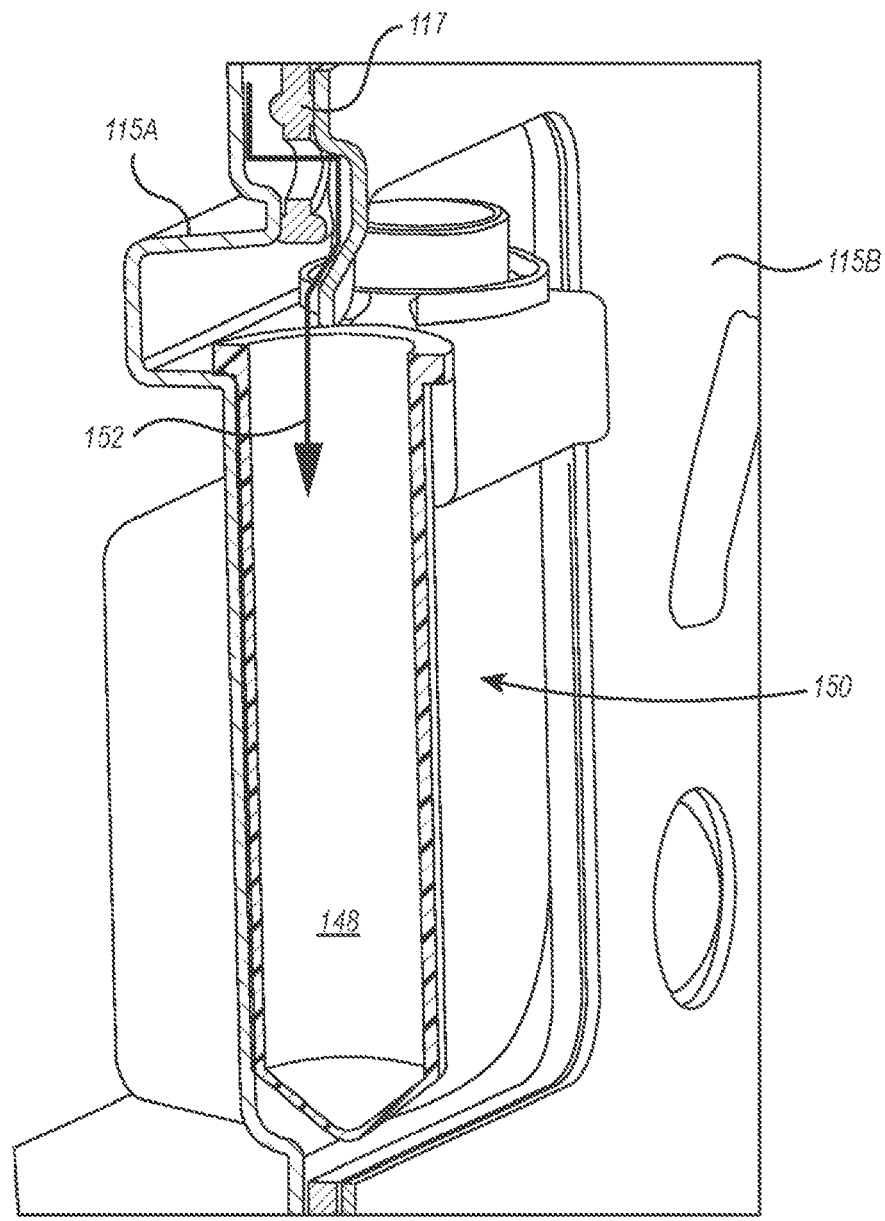
FIG. 6 illustrates an exemplary embodiment of a purification cartridge receptacle, shown as housing an output container positioned to receive the target nucleic acid in purified form.

The output container 148 can be any container suitable for receiving purified nucleic acid. For example, the output container 148 can include a standard microcentrifuge tube. To ensure that the purified nucleic acid is transferred into the output container instead of remaining associated with the cartridge, the cartridge 100 can incorporate a unique shape that overcomes the surface tension between the cartridge materials and the purified nucleic acid. In particular, the unique shape (illustrated by the arrow 152 in FIG. 6) prevents or reduces the amount of purified nucleic acid that sticks to the external walls 115a, 115b of the cartridge rather than falling into the output container.

The surface energy of the external walls 115a, 115b is generally greater than that of the elastic intermediate layer 117 (e.g., the external walls can be made of or include PVC, and the surface energy of PVC is much greater than that of most elastic intermediate materials, such as silicone), which allows the nucleic acid to preferentially adhere to the external layers instead of the elastic intermediate layer. Accordingly, the output container 148 is positioned within the cartridge 100 so as to align the middle of the external layer 115b with a center and/or central axis of the output container 148. In some embodiments, the external layer so aligned may include a small tab that promotes drop formation and deposit into the output container.

Once the purified nucleic acid is received within the output container 148, the automated nucleic acid purification protocol is complete, and the output container 148 can be removed from the cartridge 100 by a user via an easily accessible receptacle area.

Figure 7A:
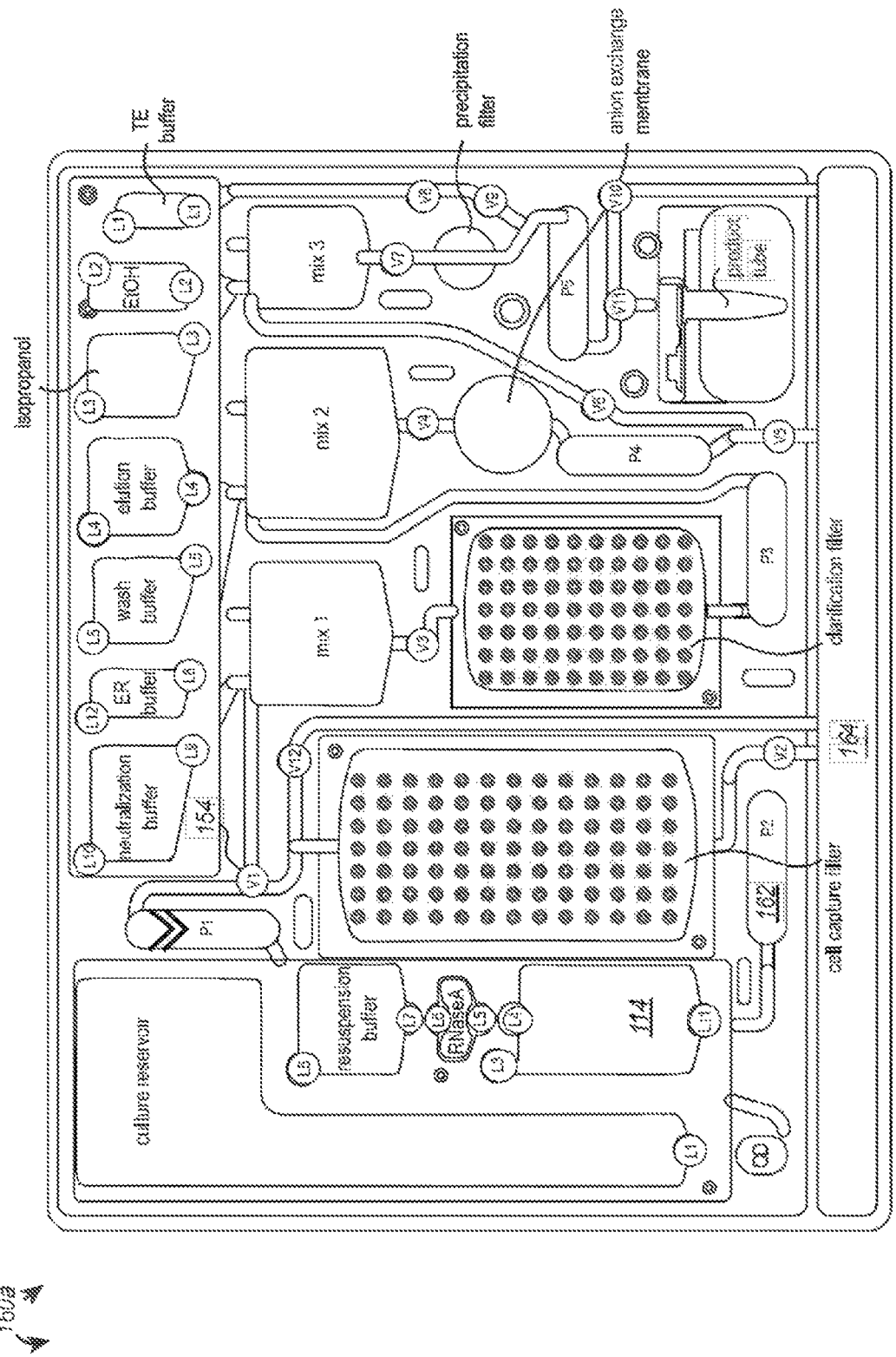
FIG. 7A illustrates another embodiment of an exemplary cartridge configured for use with a system for the automated purification a target nucleic acid from a biological sample.

It should be appreciated that the particular organization, size, and shape of the various components of the cartridge 100 illustrated and discussed in FIG. 4 and throughout FIGS. 5A-5K above are exemplary in nature, and other configurations, organizations, shapes, and sizes of the various components are included within the scope of this disclosure. For example, as shown in FIG. 7A yet another embodiment of an exemplary cartridge 160a configured for use with a system for the automated purification a target nucleic acid from a biological sample is provided. As shown, the cartridge 160a includes many of the same or similar reagents, buffers, filters, and membranes as the cartridge 100 of FIGS. 4 and 5A-5K. However, the cartridge 160a includes a single waste reservoir 164 instead of three separate waste reservoirs 108, 130, 142 provided in the cartridge 100 of FIGS. 4 and 5A-5K. In instances where the waste and cartridge are separately disposed of, a single waste reservoir, such as the waste reservoir 164 of FIG. 7A can beneficially allow the user to empty a single waste reservoir instead of accessing multiple separate waste reservoirs.

As a further example of the differences between the cartridge 160a of FIG. 7A in the cartridge 100 of FIGS. 4 and 5A-5K, the cartridge 160a includes an additional pump 162 located upstream of the lysis buffer reservoir 114 and downstream of the cell capture filter. By having pumps located on either side of the cell capture filter, there can be, for example, improved suction when passing the biological sample through the cell capture filter from the culture reservoir and additionally when backwashing the resuspension/lysis buffer solution over the cell capture filter.

Figure 7B:
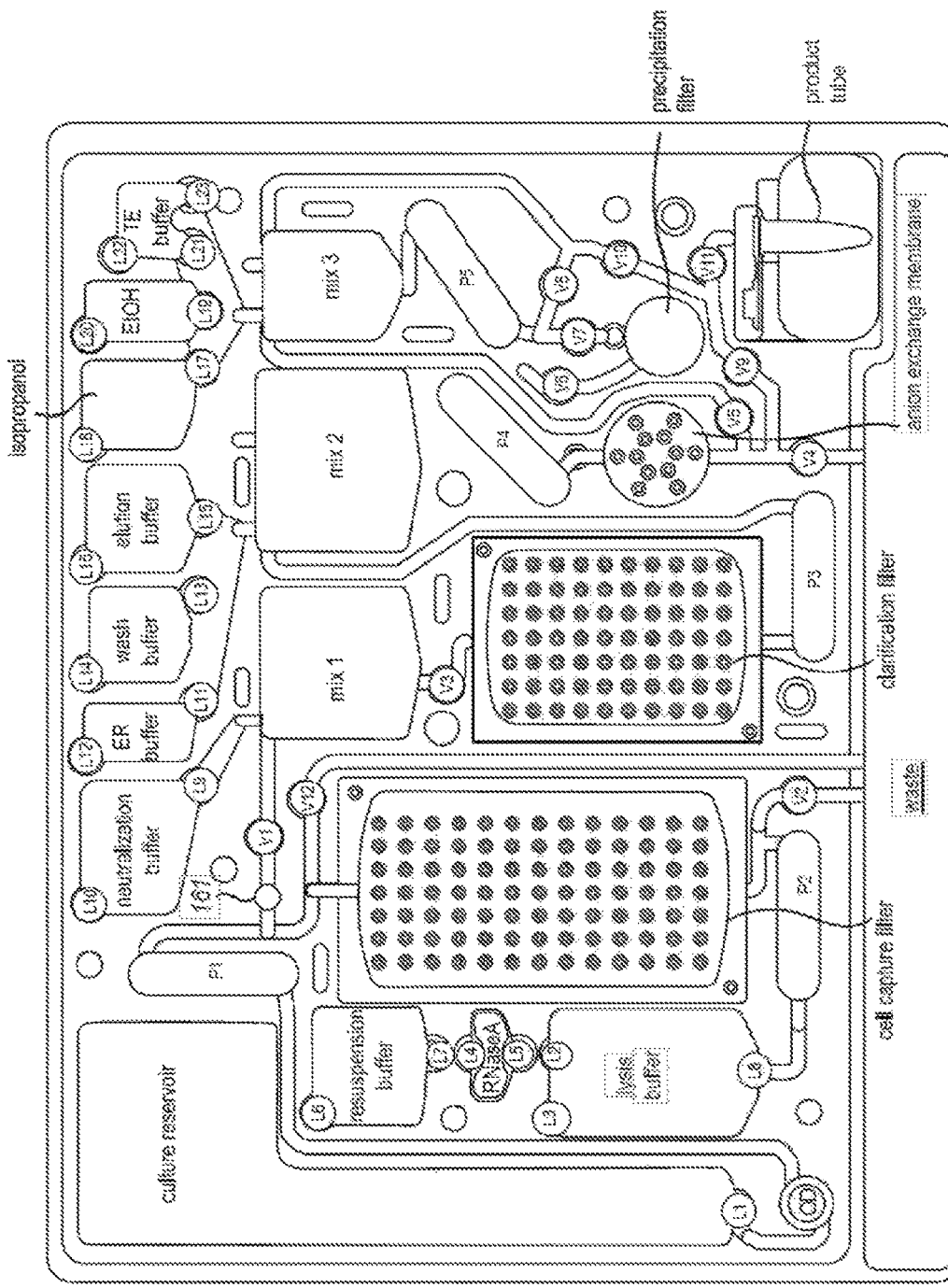
FIG. 7B illustrates yet another embodiment of an exemplary cartridge configured for use with a system for the automated purification a target nucleic acid from a biological sample.

Another embodiment of an exemplary cartridge 160b configured for use with a system for the automated purification a target nucleic acid from a biological sample is provided in FIG. 7B. As shown, the cartridge 160b includes many of the same or similar reagents, buffers, filters, and membranes as the cartridges 100 and 160a of FIGS. 4, 5A-5K, and 7A. Similar to the cartridge 160a of FIG. 7A, the cartridge 160b of FIG. 7B includes a single waste reservoir instead of three separate waste reservoirs provided in the cartridge 100 of FIGS. 4 and 5A-5K.

As a further example of the differences between the cartridge 160b of FIG. 7B and that illustrated in FIG. 7A, the cartridge 160b includes a pressure sensor 161 located between the cell capture filter and the first mixing chamber. The pressure sensor 161 can be used, for example, to monitor the pressure within the cartridge during cell capture and/or elution of cells/cellular components from the cell capture filter. As provided above, the pressure within the cartridge can build up as the cell capture filter receives more and more cells. The pressure sensor 161 can be used to prevent the pressure within the cartridge from building to a break point where the filter or other components of the cartridge fail. Additionally, the pressure sensor 161 can be used as a means for regulating the pumping action of the system. For example, the pump can be powered using a threshold-based on/off hysteresis scheme in which the pump is turned on fully until it reaches a pre-defined upper threshold (e.g., 10 psi) and then remains fully off until it reaches a pre-defined lower threshold (e.g., 2 psi), at which point the pump would be turned on again until the pressure once again reaches the upper threshold. It should be appreciated that the thresholds can be adjusted at the system level during manufacturing and/or by a user through a configurable setting (e.g., by accessing a user interface associated with the system).

As a further example, the pressure sensor can be used to regulate a pump according to a PID (proportional/integral/differential) control loop that seeks to actively control the duty cycle (e.g., speed) of the pump to maintain a pressure setpoint. In this case, instead of reaching an upper threshold and the pump being turned off entirely, the speed of the pump could be ramped down as the upper threshold is approached such that the pressure could be maintained at or near the upper threshold and pumping action would continue.

As further illustrated in FIG. 7B, the TE buffer reservoir can be partially divided with two separate exit ports. This can beneficially allow for multiple TE buffer wash cycles while maintaining a single reservoir. For example, a first volume of TE buffer can be washed through the third mixing chamber to wash any residual ethanol from the chamber and into waste. The remaining TE buffer can be washed over the precipitation filter to solubilize the retained target nucleic acid for collection in the product tube. This intermediate wash step can increase the efficiency and/or concentration of plasmid obtained from the precipitation filter.

Figure 7C:
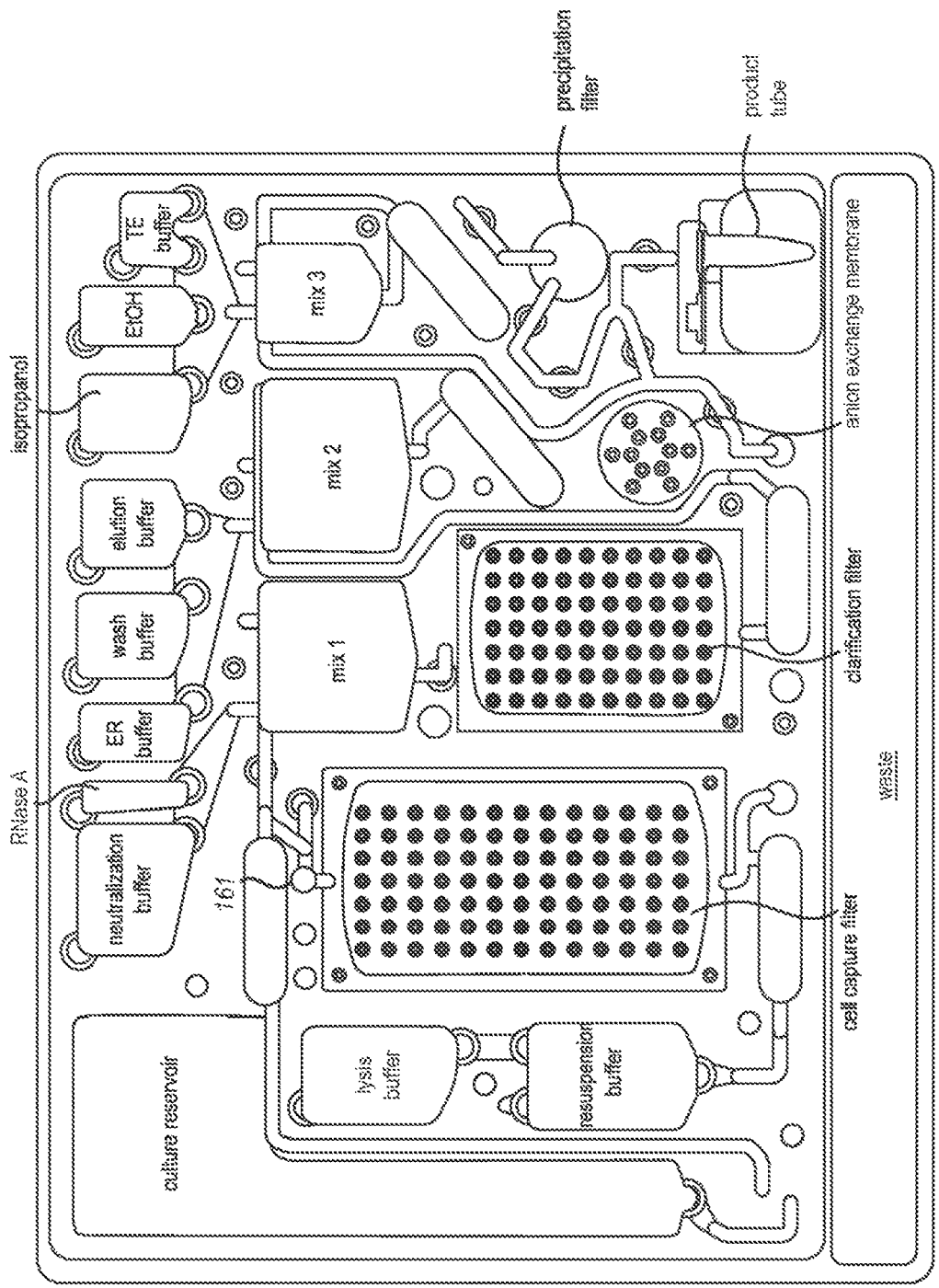
FIG. 7C illustrates still yet another embodiment of an exemplary cartridge configured for use with a system for the automated purification a target nucleic acid from a biological sample.

Another embodiment of an exemplary cartridge 160*c* configured for use with a system for the automated purification a target nucleic acid from a biological sample is provided in FIG. 7C. As shown, the cartridge 160*c* includes many of the same or similar reagents, buffers, filters, and membranes as the cartridges 100, 160*a*, and 160*b* of FIGS. 4, 5A-5K, 7A, and 7B. As shown in FIG. 7C, the cartridge 160*c* can remove the RNAse A from the triple stack of lysis buffer and resuspension buffer to be added to the first mixing chamber following resuspension of cells from the cell capture filter. For example, in an exemplary operation, cells can be captured on the cell capture filter, as described above. However, instead of washing the cells from the cell capture filter using a solution of combined lysis buffer, RNAse A, and resuspension buffer, the cells can be resuspended from the filter and into the first mixing chamber through a backwash step (similar to that described above with respect to FIG. 5A). The lysis buffer can then be pushed through the cell capture filter and into the first mixing chamber to cause cellular lysis. The RNAse A can be preloaded into the first mixing chamber, drained into the first mixing chamber at the same time the resuspension buffer brings cells from the filter to the mixing chamber, or as the lysis buffer is washed into the first mixing chamber. It should be appreciated that in some embodiments, the lysis buffer and resuspension buffer can be joined prior to resuspending the cells from the cell capture filter into the first mixing chamber.

The cartridge 160*c* of FIG. 7C can additionally have a recirculation fluid channel associated with the third mixing chamber. The recirculation channel can be used to, for example, recirculate a first TE buffer rinse through the third mixing chamber prior to moving the rinse to the waste reservoir in preparation for passing TE buffer (or other elution fluid) through to the precipitation filter. This can advantageously increase the efficiency, purity, and/or concentration of target nucleic acid eluted from the precipitation membrane.

Additionally, or alternatively, cartridges of the present disclosure can include one or more additional bypasses or vents. For example, a vent may be associated with the cell capture filter such that the pump pressure does not exceed a threshold pressure. This can beneficially prevent the cartridge from being subjected to destructive forces due to a clogged filter. A bypass valve may additionally be used to move unfiltered media to waste. In some instances, such a bypass valve could be initiated to retrieve media loaded into the cartridge that is to be recollected or otherwise not processed.

Additionally, or alternatively, a plurality of windows can be placed throughout the cartridge such that the presence of fluid can be determined (e.g., by measuring optical density of a channel coincident with one of the windows). This can be beneficial for the dynamic processing of samples, such as, for example, for processing samples that may require longer filtration times (e.g., a stool sample or dense bacterial culture versus a water or urine sample).

It should be further appreciated that the layout and design of the cartridges disclosed herein can accommodate the bespoke preparation of solutions and reagents using a series of component reservoirs. For example, instead of having a single reservoir for each of lysis buffer, resuspension buffer, etc., the cartridge may have separate reservoirs for the component parts of each buffer or reagent and may generate a specified volume of each required buffer or reagent when needed (e.g., by mixing within a mixing chamber prior to dispensing and/or dispensing directly into the sample).

Accordingly, the organization, layout, and size of various components within the purification cartridge can be adjusted and/or changed based upon the number and types of filters/membranes and/or buffers/reagents used in the purification protocol as well as the volumes and steps associated with the processing of different biological samples and/or with various different purification protocols, as can be appreciated by one having skill in the art.

Fluid Release Mechanisms

The following disclosure relates to exemplary embodiments of a system for automated nucleic acid purification that may be utilized during such automated purification processes to selectively release fluids from an input reservoir, buffer/reagent reservoir, mixing chamber, or other areas of a purification cartridge. The fluid release systems can include interacting components from disclosed purification instruments and purification cartridges. For example, an actuator portion of the fluid release system may be associated with and controlled by the purification instrument and interact with flexible regions of the purification cartridge to cause fluid to be released.

Fluid Release Systems Overview

Nucleic acid purification procedures are manual, lab processes requiring specialized skills and can take hours to perform. Owing at least in part to the many and varied fluids required at specific timepoints during the purification process, it has proven difficult to automate. Previous attempts have focused on replicating the manual process using robotics, but these approaches require a large capital investment in the expensive robotics equipment in addition to additional expenses associated with lab equipment typically utilized during the manual process (centrifuges, vacuum manifolds, etc.). These approaches additionally failed to reduce the number and type of consumables as they relied mostly on the filtration columns and buffers provided in commercial purification kits.

Additionally, prior approaches have failed to improve mechanisms for fluid release during nucleic acid purification processes. Instead, prior approaches continue to move various fluids by pipetting, similar to the manual process, or by dispensing aliquots from a large reservoir into various tubes or filtrations columns. In the former, there is additional cost and increased processing time resulting from the requisite loading and ejecting of pipette tips in addition to the need to monitor and replace these additional consumables. Regarding the latter, there is a heightened risk of cross-contamination between samples, and particular time and attention are required to wash and/or sterilize tubing or injection ports between samples. In either case, the proposed solutions fail to address the outstanding need for a self-contained fluid release system that reduces the number and/or type of consumables associated with fluid release/transfer during the nucleic acid purification process and that reduces or eliminates the risk of cross-contamination between samples preparations.

Thus, designing a system capable of selectively releasing the appropriate fluid (e.g., sample, buffer, reagent, or combinations thereof) during an automated nucleic acid purification procedure presents several challenges. As described in more detail below, the fluid release systems described herein are capable of meeting one or more of the above-mentioned challenges by including a flexible gasket positioned between a fluid reservoir on the one side and an actuator on the other. The actuator is operable to deflect the flexible gasket and cause a frangible seal retaining the fluid within the reservoir to breach, thereby selectively release the fluid from the reservoir.

In some embodiments, the flexible gasket, frangible seal, and reservoir are each components of the purification cartridge, and the actuator is a component of an associated purification instrument. This beneficially allows for the controlled release of fluids from a consumable cartridge without cross-contaminating samples. The actuator interfaces with a first side of the flexible gasket and by depressing the flexible gasket from the first side, the gasket is deformed towards the frangible seal and causing the opposing side of the gasket to interact with and disrupts the frangible seal. In this way, the actuator is separated from the fluid by the intervening gasket and never contacts the fluid directly. The actuator can be repeatedly used to puncture fluid containers without requiring cleaning or disposal between or within sample processing and with little to no risk of contamination.

As an additional benefit, the disclosed fluid release systems simplify the fluid release process and enable faster processing times while being essentially agnostic to the volumes of fluids released. That is, the disclosed fluid release systems can be used to release small or large volumes of fluids because the components and processes for fluid release are essentially independent of the reservoir size. Also, the mechanical means of releasing fluid is simple; that is, it does not require complex mechanisms that may prove to be unreliable over time. This can increase the reliability, repeatability, and long-term utility of the system, particularly in embodiments that utilize single-axis actuation.

Fluid Release Mechanisms

Referring now to FIGS. 8A-8C, illustrated is an exemplary embodiment of a fluid release system for holding and selectively releasing a fluid. As shown, the system includes an actuator 166 and a fluid reservoir 168. The fluid reservoir 168 is configured to retain a fluid and is bounded at least partially by an external layer of the cartridge (e.g., external layer 115a) and a frangible seal 170, which in an unbroken state acts to retain fluid within the reservoir 168.

As used herein, the term "frangible seal" is intended to include a pierceable material configured to tear, break, or otherwise catastrophically fail—thereby no longer acting as a seal—in response to application of a mechanical force. Frangible seals of the present disclosure can be comprised of a chemically inert material facing the reagent side of an associated channel or reservoir. In one embodiment, the frangible seal comprises a thin layer of chemically inert material configured to rupture in response to an external mechanical force while maintaining a fluid tight seal. In some instances, the inert material is a plastic such as polypropylene, polyvinylchloride, polystyrene, or similar. The frangible seal can additionally include a second reinforcing layer comprised of, for example, a metal foil. The second reinforcing layer can be fused with the inert material to functionally form a single layer such that breach of either the plastic or reinforcing layer is functionally equivalent to a breach of both layers. Other suitable materials for the frangible seal can be selected as known in the art, such as, for example, the frangible seals formed over pharmaceutically filled cavities of pre-formed plastic packages (e.g., blister packs) or other frangible seals formed over some consumer food products. For example, a foil layer, which has roughly zero moisture vapor loss can be fused and/or used with a second reinforcing layer such as Aclar to further retard and/or prevent moisture vapor loss.

Disposed between the frangible seal 170 in the actuator 166 is a flexible gasket 172. As shown in FIG. 8A, the flexible gasket 172 is a component of the purification cartridge. The flexible gasket may be part of an intermediate layer 117 disposed between two external layers 115a, 115b. For example, the flexible gasket 172 may be an extension of the elastomer layer that is sandwiched between the inner and outer thermoformed layers of the cartridge, similar to cartridges described herein. In such embodiments, the fluid reservoir 168 may be at least partially defined by the flexible gasket 172 in one of the two external layers of the cartridge. As described in greater detail herein, the external layers of the cartridge 115a, 115b can be made of or include a thermoformed plastic.

In some embodiments, and as shown in FIG. 8A, the flexible gasket 172 forms a channel or conduit 174 through which fluid can pass after being released from the fluid reservoir 168. To selectively release the fluid from the reservoir 168, the actuator 166 is caused to move from a first position (indicated by arrow A) to a second position (indicated by arrow B in FIG. 8B). In doing so, the actuator 166 contacts a first side of the flexible gasket 172, and with continued axial movement toward the flexible gasket 172, the actuator 166 causes the flexible gasket 172 to deflect toward the frangible seal 170.

As shown in FIG. 8B, the actuator 166 can be moved a distance toward the reservoir 168 and cause the deflected flexible gasket 176 to pierce or puncture the frangible seal 170. In this way, the actuator 166 does not directly contact the frangible seal 170 or the contents of the fluid reservoir 168. Instead, the surface of the deflected flexible gasket 176 contacts and ruptures the frangible seal. While some fluid from the reservoir 168 may pass between the deflected flexible gasket 176 and the breached seal 178, upon retracting the actuator 166, as shown in FIG. 8C, the flexible gasket 172 returns to its original position (e.g., because of its elastic properties) and provides a clear conduit 174 through which fluid may exit the fluid reservoir 168 via the aperture 180 formed by the breached seal 178.

It should be appreciated that the fluid reservoir 168 can be any reservoir or chamber within the purification cartridge, including, for example, the input reservoir, buffer/reagent reservoirs, mixing chambers, or the like. As such, the fluid within the fluid reservoir 168 may be any of an input sample, resuspension buffer, RNase A, proteinase K, lysis buffer, neutralization buffer, binding buffer, endotoxin removal buffer, wash buffer, elution buffer, isopropanol, 70% ethanol, TE buffer, water, combinations of the foregoing, or any other fluid, reagent, buffer, enzyme or mixture used or formed within a nucleic acid purification protocol. Additionally, the conduit 174 can provide a pathway for the released fluids to travel between the reservoir 168 and a next or final destination 182 within the purification cartridge.

The system illustrated in FIGS. 8A-8C can include components from a nucleic acid purification cartridge and from an associated instrument. The system illustrated in FIGS. 8A-8C can include components from a protein purification cartridge and from an associated instrument. For example, the actuator 166 may be a component of the purification instrument, whereas the fluid reservoir 168, associated frangible seal 170, and flexible gasket 172 mail be components of a purification cartridge, as described in greater detail herein. As such, movements of the actuator 166 may be controlled by the instrument, which as described above can include computer-executable instructions or other programmable elements that allow for time- or situation-dependent release of fluids according to a predefined or user-defined protocol. This can beneficially allow for the dynamic implementation of various nucleic acid purification protocols using any of the myriad combinations of buffers, reagents, and processing parameters without necessitating a change to the physical components of the instruments, such as the actuator. Stated another way, the disclosed fluid release systems enable a plurality of uses with a single hardware configuration.

It should be appreciated, however, that the positioning of actuators within a nucleic acid or a protein purification instrument can be dynamic as well. In some embodiments, a purification instruments may have a single actuator that is repositioned throughout a purification protocol such that it is aligned with and causes the rupture of various frangible seals at different times. Additionally, or alternatively, a purification instrument may have a plurality of actuators aligned with or movable between corresponding frangible seals on the purification cartridge.

In some embodiments, the frangible seal 170 is a foil seal. Alternatively, the frangible seal can be made of or include any suitable material that can withstand the pressures exerted upon it by fluid within the reservoir or chamber with which it is associated—but which will rupture upon a stronger force being exerted upon it by the flexible gasket via the actuator. In some embodiments, the thickness of the frangible seal can be adjusted to account for different intra-reservoir pressures and/or actuator forces.

In some embodiments, and as illustrated in FIGS. 8A-8C, the actuator may have a pointed head. This can advantageously allow the force exerted by the actuator to be focused on a smaller area of the frangible seal, thereby causing a localized catastrophic failure in the frangible seal that can be propagated outward to widen the aperture. It should be appreciated, however, that other shapes or forms of the actuator may be provided to achieve the same or similar result. For example, an exemplary actuator may have a tip diameter of 1 mm, 2 mm, 3 mm, 4 mm, 5 mm, 7 mm, 10 mm, or a tip diameter that is less than any one of the foregoing. The tip diameter can also be selected from any diameter within a range bounded by two of the foregoing diameters (e.g., between 1 mm-10 mm, between 2 mm-5 mm, between 3 mm-7 mm, between 2 mm-4 mm).

Flexible Air Vents

In some instances, releasing fluids via the mechanisms described above can cause negative pressure to build within the reservoir as the fluid escapes. This can cause incomplete voiding of fluid from the reservoir (e.g., in a closed system), or alternatively, it can cause intermittent flow from the fluid reservoir and/or gurgling of air into the fluid reservoir (e.g., in an open system). Each of the foregoing can negatively impact the efficiency of the automated purification process and/or the purity or concentration of the output target nucleic acid or output target protein.

For example, incomplete voiding can alter the desired chemistry if the fluid is mixed with a suspension, lysate, or eluate and cause a different or less optimal effect. If, for example, the incompletely voided reservoir contained wash buffer or endotoxin removal buffer, the output target nucleic acid may be contaminated or unfit for its intended purpose. As a nonlimiting example of the foregoing, the target nucleic acid may be a plasmid intended for use mammalian cell culture assays, and if the plasmid was purified from a Gram-negative bacterium and incompletely treated with the requisite volume of endotoxin removal buffer, a toxic or inflammatory concentration of lipopolysaccharide may remain associated with the purified plasmid DNA such that it cannot properly utilized for its intended purpose.

Intermittent flow and/or gurgling of air into the fluid reservoir can similarly negatively impact the efficiency of the automated purification process and/or the purity or concentration of the output target nucleic acid or target protein. For example, if the fluid contains a surfactant, gurgling of air into the fluid reservoir can cause the lower-surface-tensioned fluid to foam or bubble, which can lead to incomplete voiding of the fluid. Many lysis buffers include surfactants, and incomplete association of lysis buffer with the input biological sample can reduce the amount of target nucleic acid that can be purified.

Figure 9A:
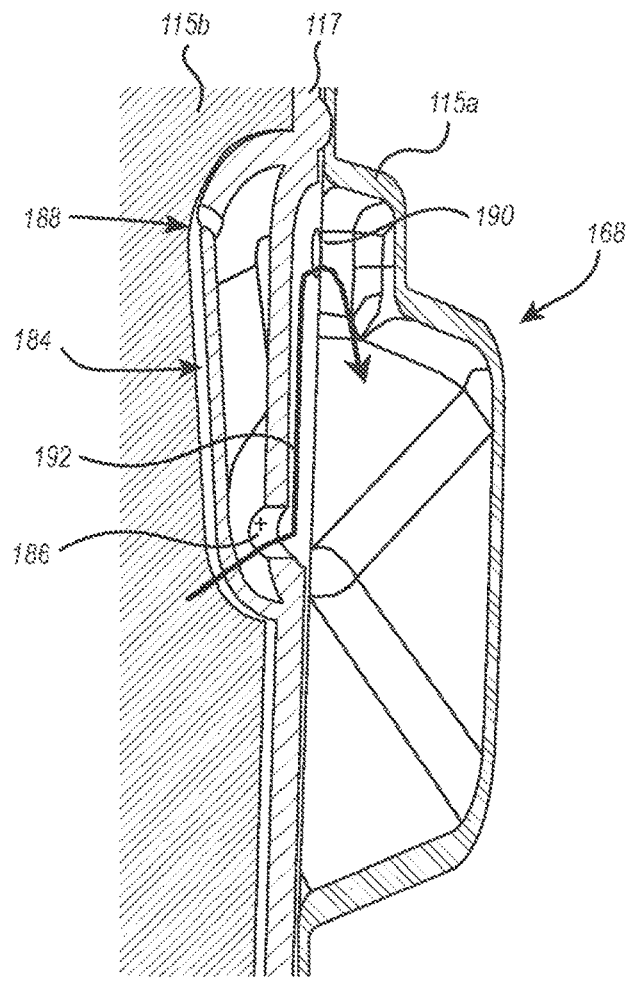
FIGS. 9A and 9B illustrate an exemplary embodiment of a flexible air vent for selectively venting air into an associated reservoir or mixing chamber of a purification cartridge.
Figure 9B:
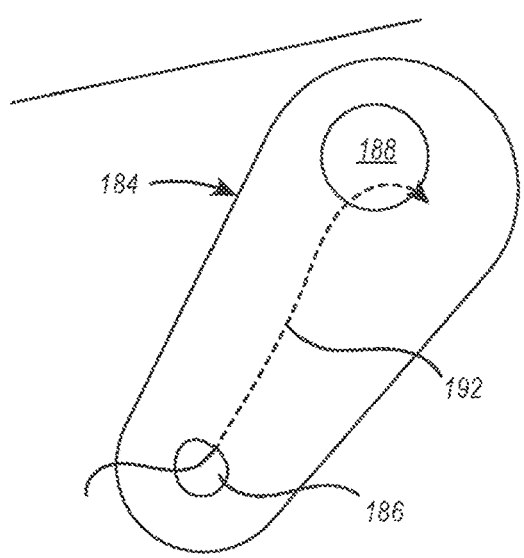

Fluid release systems of the present disclosure can solve one or more of the foregoing problems. For example, exemplary fluid release systems may be configured to vent air into the fluid reservoir to promote complete or uninterrupted voiding of fluid from the reservoir. In some embodiments, and as illustrated in FIGS. 9A and 9B, a fluid release system can include an air venting system 184 associated with the fluid reservoir 168. The air venting system 184 may be operable to rupture a frangible air seal 190 associated with the fluid reservoir 168 and thereby route air into the reservoir 168.

As shown in FIGS. 9A and 9B, the air venting system 184 can be part of the purification cartridge. The system 184 can include a flexible air vent 188, which, similar to the flexible gasket described above, may be part of an intermediate layer 117 disposed between two external layers 115a, 115b of the cartridge. In some embodiments, the flexible air vent 188 is an extension of the elastomer layer and may partially define the fluid reservoir 168.

As shown, the flexible air vent 188 is separated from fluid communication with the reservoir 168 by a frangible air seal 190. To selectively vent air into the reservoir 168, an actuator (not shown) can be moved into contact with the flexible air vent 188, and with continual axial movement toward the reservoir 168 (e.g., left to right as shown in FIG. 9A), the actuator can cause the flexible air vent 188 to deflect toward the frangible air seal 190 until the deflected air vent contacts and perforates or otherwise ruptures the frangible air seal 190. Similar to the flexible gasket described above, the flexible air vent 188 may return to its non-deflected position following removal of the deflecting force applied by the actuator.

The flexible air vent 188 can form a channel or conduit 192 between the fluid reservoir 168 and the outside air (e.g., via the ruptured air seal and the aperture 186 formed by the air vent 188). As shown, access to the conduit the conduit 192 from the outside air can begin at the aperture 186 and travel longitudinally along the fluid reservoir 168 to terminate at or beyond the frangible air seal 190. In some embodiments, the frangible air seal 190 can be positioned at the top of the fluid reservoir 168, directionally away from the force of gravity, and the frangible seal (not shown) for releasing fluid from the reservoir 168 can be positioned at the bottom of the fluid reservoir, directionally toward the force of gravity. In this orientation, breaching the frangible seal and the frangible air seal can result in fluid exiting the reservoir through the bottom of the fluid reservoir by the force of gravity with pressure equalizing air entering at the top of fluid reservoir. This can promote complete voiding of fluids from the reservoir and can also prevent blockages or gurgling resulting from unequal pressure gradients between the fluid reservoir and the outside air.

In some embodiments, the frangible air seal may be breached prior to the frangible seal so that pressure within the fluid reservoir can be equalized with the outside air before releasing any fluid therefrom. Alternatively, the frangible air seal may be breached after the frangible seal to provide equilibrated pressure as the reservoir empties. For fluid reservoirs that are at or near capacity, breaching the frangible air seal after the frangible seal may reduce the likelihood that fluid exits through the breached air seal as the fluid level may be lower and/or the available volume of the fluid reservoir headspace associated with the frangible air seal may be greater. In some embodiments, the frangible air seal may be breached by the same actuator as the frangible seal described above.

In some embodiments, the frangible air seal and frangible seal are ruptured concurrently or nearly concurrently. The frangible seals may thus be ruptured by different actuators. Additionally, movements of the actuator relative to the frangible air seal may be controlled by a purification instrument, which as described above can include computer-executable instructions or other programmable elements that allow for time- or situation-dependent venting of air according to a predefined or user-defined protocol. This can beneficially allow for controlled fluid flow throughout the nucleic acid purification process without the actuator contacting any fluid or otherwise contaminating the sample.

Protein Purification Cartridges, Instruments and Systems

The present disclosure is directed to cartridges, automated systems, and methods for purifying a target biomolecule from a biological sample. The foregoing discussion, particularly that related to FIGS. 3A-5K and FIGS. 7A-C, illustrates various exemplary cartridge designs and processing workflows for automatedly purifying a target nucleic acid. In a similar fashion, embodiments disclosed herein can include analogous cartridges and processing workflows for automatedly purifying a different target biomolecule, namely a target protein.

Protein purification is vital for the characterization of the function, structure, and interactions of proteins. The various steps in the purification process may include cell lysis, separating the soluble protein components from cell debris, and finally separating the protein of interest from product- and process-related impurities. However, many existing methods for protein extraction and purification from liquid cell cultures are time-intensive and largely manual processes. These methods require technical expertise and specialized equipment to perform various steps of the methods. For example, one typical procedure would include centrifugation of the liquid cell culture to harvest the cells, followed by resuspension of the resultant cell pellet in a lysis buffer to lyse the cells. The lysate is then clarified through an additional centrifugation step, where the clarified lysate is decanted for collection. The clarified lysate may then be run through a protein purification column (or other filter, resin, or protein capture means) to further purify the desired protein for collection in an elution buffer for further downstream workflows.

The automated systems and accompanying cartridges described herein enable automation of steps in the protein purification process and can include automation of essentially the entire protein purification process after the biological sample comprising the target protein is added to a corresponding protein purification cartridge and operable automated system. For example, the cartridges and systems disclosed herein are adapted for use in purifying and/or isolating proteins from a bacterial and/or eukaryotic culture. In one embodiment, the target protein is made by or otherwise associated with eukaryotic cells such as yeast (e.g., *Saccharomyces cerevisiae*), or insect cells, or rodent cells (e.g., mouse, rat, or hamster cells) such as CHO cells, or primate/human cells such as 293 or COS cells. In another embodiment, the target protein is made by (e.g., as a recombinant protein) or otherwise associated with prokaryotic cells, such as *E. coli*. Regardless of the cell type, the automated protein purification systems and associated cartridges and methods can be adapted to purify and collect a target protein therefrom.

Similar to the target nucleic acid purification systems and cartridges described above, automated protein purification cartridges of the present disclosure can be adapted to receive a biological sample containing the target protein via an associated culture reservoir and to process the biological sample through a number of interconnected bioprocessing assemblies to yield the purified target protein. For example, after the biological sample (e.g., culture of prokaryotic/eukaryotic cells) containing the target protein is added to the target protein purification cartridge, the cartridge can be processed, as above, in a first bioprocessing assembly configured to isolate the cellular fraction from the sample/culture supernatant. It should be appreciated that in instances where the target protein is a secreted protein, the supernatant can be further processed instead of being passed to waste. Further, in instances where the target protein is cell associated, the cellular fraction of the biological sample/culture can be captured on a cell capture membrane with the supernatant passing to waste. It should be appreciated that the bioprocessing assemblies and reagents disclosed above with respect to nucleic acid purification can be modified for protein purification.

As a non-limiting example, cells from a suspension can be added to a target protein purification cartridge and passed through a filter where the cells are captured by filtration on a first side of the filter. The filtrate passes through the filter and past a second side thereof and may be directed toward a waste receptacle. Completion of this and each subsequent step may optionally be detected by an air/bubble sensor, or by any other methods for detecting the presence/absence of fluid flow or a threshold fluid flow rate disclosed herein and/or known to one having skill in the art. As described above, the target protein purification cartridge can be associated with a complementary automated purification system that utilizes a pumping action to cause the biological sample to be drawn through the filter in a first flow direction and may additionally be followed by a second operating state to facilitate liquid flow in an opposite, second flow direction.

In some embodiments, a suitable cell capture filter system is selected for use within a target protein purification cartridge primarily based on its flow rate and filter capacity. Other filter properties, such as pore size, can be one consideration for selecting a suitable cell capture filter system (e.g., to capture the cells harboring the target protein). As a non-limiting example, an *E. coli* strain can be engineered to produce a recombinant target protein. A culture of these *E. coli* can be captured on a membrane system within an automated purification cartridge that comprises a 0.2 µm hollow fiber filter membrane. As an additional example, a cell capture filter associated with a target protein purification cartridge includes a plurality of cellulose acetate-based porous hollow fibers, bent into a series of loops. This collection of loops advantageously provides the filter with a large surface area for capturing and/or processing the biological sample and/or partially purified target protein. The open ends of these loops are potted into polyurethane or similar polymer to form an end plug (e.g., machined to ensure that the open ends of the loops remain open). In one embodiment, the hollow fiber filter may be a MEDIAKAP® filter commercially available from SPECTRUM® Laboratories, Inc., such as the MEDIAKAP-25 filter. Other filters and/or cell capture systems can be used in accordance with the size, polarity, and/or presence of affinity tags, in addition to any other characteristic or property of the target protein, as known in the art.

The bioprocessing assemblies within target protein purification cartridges of the present disclosure can additionally include fluid mixing chambers and/or may contain a solid support for processing one or more samples. The solid support can be any support for filtering, washing, staining, eluting, collecting, processing, or conducting chemical reactions or bioprocessing. In some embodiments, the solid support may be selected from one or more of filter cassettes, filter paper, precipitation membranes, precipitation filters, solid phase extraction columns, solid phase extraction cassettes, solid phase extraction disks, resins, membranes, such as blotting membranes, filter membranes, PVDF membranes, nylon membranes, positively charged nylon membranes and nitrocellulose membranes, reaction beads, such as glass beads and magnetic beads, rigid planar solid supports that contain arrays of biomolecules such as protein arrays, tissue arrays, microscopic slides, and combinations thereof.

In some embodiments, the solid support in one or more bioprocessing chambers may comprise a filter paper, a filter, or a filter cassette. The filter paper, filter, or filter cassette may include any suitable type of filter having an appropriate chemistry, pore size, shape, three dimensional configuration, such as a symmetrical or asymmetrical three dimensional configurations including "V" or funnel-shaped pore configurations, and/or surface area for the intended use. That is, the solid support can be selected based on properties of the target protein and/or the desired purification protocol. Additionally, the solid support can be constructed for flow through, cross flow, tangential flow, or any combination thereof. It should be appreciated that the filter paper, filter, or cassette can be a single layer or multiple-layer filter that is made of or includes any suitable material, such as polyethersulfone, polyethylene, ultra-high molecular weight polyethylene, polypropylene, nylon, cellulose, cellulose-triacetate, polyacrylonitrile, polyamides, glass fiber, silica, polysulfone, PVDF, and the like. In some embodiments, the solid support within one or more of the processing chamber(s) is a precipitation membrane or precipitation filter, or it may alternatively be a blotting membrane. In some embodiments, the solid support could be a solid phase extraction column, a solid phase extraction cassette, or a solid phase extraction disk. In some embodiments, the solid support may include a plurality of beads, such as coated beads, coated glass beads, glass beads, magnetic beads, or coated magnetic beads. The beads can be packed into a column or in suspension within the processing chamber.

As a non-limiting example, embodiments of the present disclosure can include cartridges for purifying a target protein that have a protein capture assembly following the cell capture subassembly. The protein capture assembly can be configured to clarify lysate or can be alternatively configured to receive and bind the target protein from the clarified lysate. As such, it should be appreciated that exemplary cartridges for purifying a target protein from a biological sample can include a clarification and/or protein capture assembly fluidically connected to a cell capture assembly and/or mixing chamber in addition to one or more buffer/wash/reagent chambers. For example, a reservoir housing protease inhibitors, pH-differentiated solutions, wash buffers, elution buffers, etc. can be included in respective fluidically connected reservoirs that are sealed as described herein. Respective omissions and/or additions of buffers and processing steps within and between bioprocessing assemblies of the envisioned cartridges (e.g., as shown in FIGS. 3A-5K and 7A-C) can be adapted in accordance with a protein purification protocol instead of a nucleic acid purification protocol.

In one embodiment, the automated protein purification cartridge includes a subassembly having one or more affinity matrices/columns (e.g., instead of nucleic-acid-purification-specific membranes/filters as provided in the automated nucleic acid purification cartridges of FIGS. 3A-5K and 7A-C). Affinity chromatography is an effective technique for protein purification that often enables a single-step purification of proteins to a purity level sufficient for analytical characterization. Affinity chromatography is a separation technique based on molecular conformation—molecules that "fit" one another bind selectively in a "lock and key" fashion (e.g., an antibody may recognize and specifically bind an antigen). The technique can use application-specific chromatography resins that have ligand-specific receptors (e.g., fragments of antibodies that contain the antigen-binding domain) attached to the resin surface. Most frequently, these receptors bind to the target protein in a manner similar to that of antibody-antigen interactions. This highly specific fit between the receptor and its target compound enables affinity column chromatography that is also highly specific. Antigens bind (usually with high affinity) to the resin-bound antibody, while other sample components and impurities do not bind and, instead, flow through the affinity column to the waste container. Any bound antigen (typically the protein of interest) can then be washed and eluted from the column, often with a pH change that breaks the molecular antigen-antibody interaction, yielding a single, highly pure elution peak representing the target protein.

Accordingly, embodiments of protein purification cartridges disclosed herein can include an affinity column contained therein that can specifically bind and capture a target protein while allowing the remaining protein and cellular products to pass through the column and into waste. The column can be washed to remove any loosely bound or residual cellular debris from the column (e.g., automatedly via opening a reservoir housing wash buffer and pumping the contents through the column). A reservoir within the cartridge can include a solution operable to change the pH of the matrix/column and thereby cause elution of the target protein (e.g., into a collection tube). Other wash steps and/or purification steps can be automatedly performed using the systems and protein purification cartridges operable for such use.

As a non-limiting example, Thermo Fisher Scientific offers a variety of products for affinity chromatography through its CaptureSelect® product portfolio. CaptureSelect® products are affinity ligands based on camelid-derived single-domain antibody fragments (VHH). The affinity receptor is a 12 kDa single domain fragment that comprises the 3 complementarity-determining regions (CDRs) that form the antigen binding domain. These affinity receptors are efficiently produced in the yeast *Saccharomyces cerevisiae* and thus are not animal-derived. The affinity receptors are then covalently bound to chromatography beads, generating resins suited for protein purification via column chromatography. These can be beneficially developed with defined specificity and high avidity to the target, enabling the creation of affinity chromatography resins well suited for single-step protein purification.

Such (and similar) products can beneficially enable selectivity, affinity, and stability during the automated protein purification processes enabled by cartridges utilizing the same and can enable the exemplary benefits of single-step purification, ease of use, minimized cost of purification, effective impurity removal, higher-quality product, and increased flexibility in the purification process.

Additional examples of protein purification products that can be included within one or more subassemblies of the automated protein purification cartridges disclosed herein include Antibody Toolbox® products for the separation of immunoglobulin formats from a wide range of environments, such as plasma, milk from transgenic animals, or supernatant from mammalian cell cultures; Proteomics Toolbox® products for protein depletion to support biomarker research applications; HPLC analytical chromatography columns—rapid, sensitive, and precise quantitation and small-scale sample preparation of proteins from complex mixtures; fast protein liquid chromatography (FPLC); and/or columns having a custom antibody ligands against a specific protein or impurity, enabling affinity purification tailored to novel applications.

In some embodiments, the protein purification cartridges disclosed herein can be used to run protocols and bioprocessing procedures selected from: immunoprecipitation, recombinant protein isolation, protein labeling, separation and isolation of target protein, and automatic bead-based separation, including automatic magnetic bead-based separation. The disclosed protein purification cartridges can additionally be adapted for use with the automated systems disclosed herein and/or the systems disclosed herein can be modified to accommodate protein purification cartridges disclosed herein. It should be appreciated that the functionality of the combined cartridges and systems disclosed herein with respect to nucleic acid purification can be realized with corresponding cartridges and systems configured for protein purification. As such, the sealing mechanisms and fluid control mechanisms related to nucleic acid cartridges and systems provided herein can additionally be used and/or associated with protein purification cartridges.

In one embodiment of an automated workflow, the entire cell lysis process—including filtration of up to at least 1 L of cell suspension, any (optional) wash steps, all steps related to loading buffers/solutions into proper reservoirs or mixing chamber for incubation and/or resuspension of captured cells and lysing of cells, and collection of the clarified lysate—can be completed in 2 hours or less, preferably in 1 hour or less. In one embodiment, all steps involved in collecting a purified target protein from the clarified lysate—including purification of the target protein through the purification column, with all wash and elution steps—can be completed in about 2 hours or less, preferably in 1 hour or less. Accordingly, in one embodiment, filtration, lysis, clarification, and purification of a target protein from up to at least 1 L of cell suspension may be completed in a single automated process in about 4 hours or less, preferably in about 2 hours or less.

In some embodiments, the process workflow may include additional processing steps that may increase the total amount of run time. For example, the purified protein may be further purified (e.g., "polished") or buffer exchanged by a complementary chromatographic strategy, which may include size exclusion, ion exchange, or affinity purification. As an additional, or alternative, example, the purified protein may be proteolytically processed to remove an affinity tags encoded in the protein sequence at the amino or carboxy terminal end, followed by a final purification step. As it should be appreciated, the workflow can be scalable to accommodate filtration and/or purification requirements for volumes of cell suspension greater or less than 1 L by increasing or decreasing the size and/or number of the various system components, as needed.

Automated Purification Instrument

The following disclosure relates to exemplary embodiments of an instrument that may be utilized to provide automated purification of a target biomolecule, such as a target nucleic acid and/or target protein. The purification instrument may be utilized with other components described herein. For example, the instrument may be configured to receive and interface with a consumable purification cartridge such as described above. While some of the features of instrument or apparatus are described using nucleic acid purification as an example, it will be understood that similar instrument (with modifications described herein) will be useful for protein purification as well.

Instrument Overview

As described above, conventional protocols for purifying a target biomolecule, such as a target nucleic acid and/or target protein, are manual lab processes requiring relatively high levels of lab technician know-how and time. While a well-trained lab technician may be able to handle the various operational parameters involved in the processes, designing an instrument capable of effectively automating large portions of the processes is challenging for several reasons. For example, a device configured to carry out an automated process should be capable of effectively moving and routing fluids of varying viscosities and densities, providing release of reagents at particular required times and in conjunction with other fluid movement operations, mixing disparate fluids together, processing relatively large volume samples, and maintaining appropriate fluid separation/seals throughout the process. Such a device should also be safe for users to operate and functional for purifying a given target biomolecule, such as a preselected target nucleic acid or preselected target protein.

As described in more detail below, the purification instrument described herein is capable of meeting one or more of the above-mentioned challenges. For example, the purification instrument may include a pump assembly configured to provide pumping action through peristaltic motion in order to effectively move fluids through an inserted consumable cartridge, may include components for controlling automated mixing of fluids within the inserted cartridge, may include components for providing or enhancing fluid-tight seals on the cartridge, and may include safety mechanisms that protect a user from accidental injury and/or limit the risk of process mistakes. In some embodiments, an instrument of the disclosure may be configured to process large volume samples (e.g., about 5 ml to 5 l, or 10 ml to 500 ml, or about 15 ml to 250 ml) It should be appreciated that the systems, apparatus, cartridges can be sized down to purify smaller volumes as well (e.g., less than 5 ml such as 0.5 ml-5 ml volumes).

Figure 10:
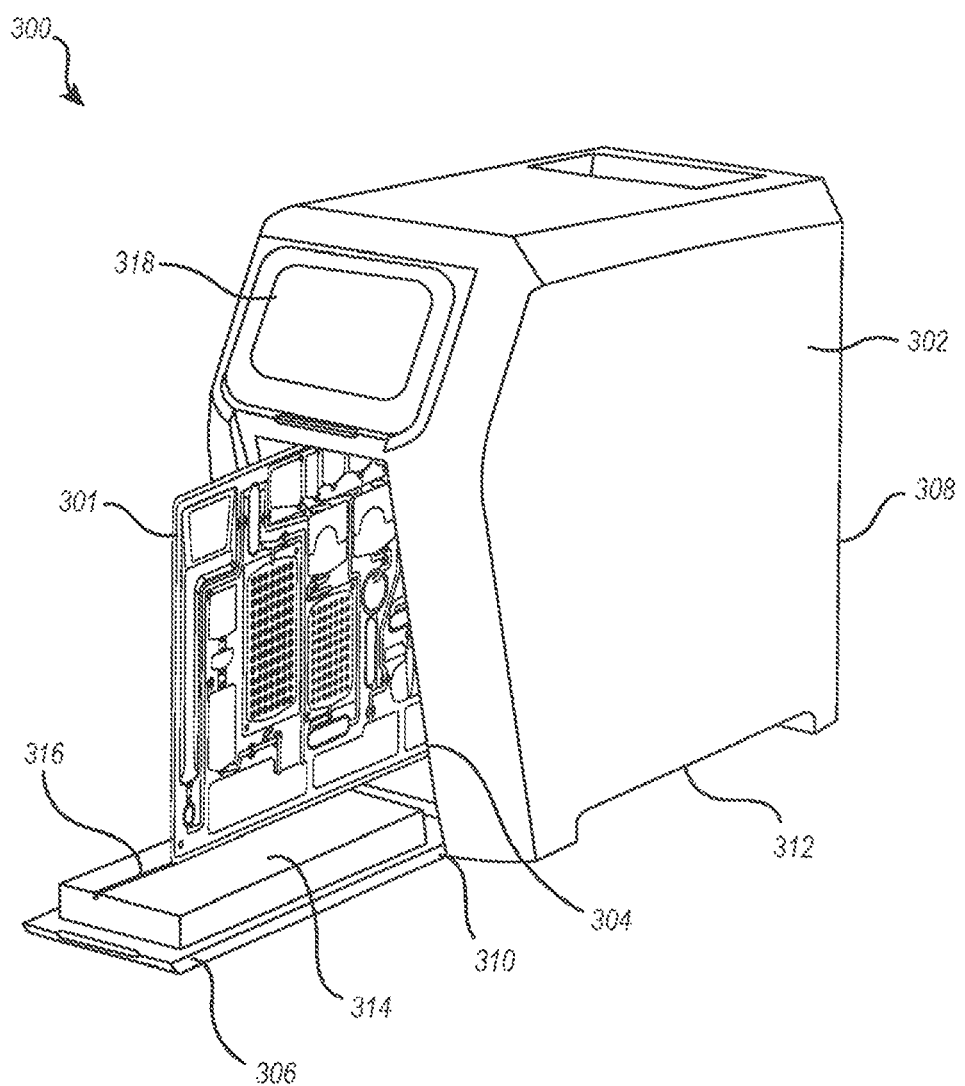
FIG. 10 illustrates an exemplary embodiment of a purification instrument capable of automated nucleic acid purification.

FIG. 10 provides an isometric view of a purification instrument 300 (which also may be referred to herein as a purification "apparatus") capable of automated nucleic acid purification. The instrument 300 includes a casing 302 that surrounds and defines an internal compartment 304. The internal compartment 304 is configured in size and shape to receive a sample purification cartridge 301. In a preferred embodiment, the purification cartridge 301 is a consumable cartridge such as a cartridge shown and described in more detail elsewhere herein. The instrument 300 includes a selectively closable access door 306 that provides access to the internal compartment 304. Other forms of inserting and/or receiving the cartridge are envisioned within the scope of this disclosure, including, for example, auto-feeding the cartridge into the instrument or other mechanisms known in the art. The instrument 300 may also include a waste tray (not shown) disposed within the internal compartment 304 and configured to collect leaks or spills from the cartridge and/or nearby areas of the instrument, such as leaks/spills of the biological sample or of the various reagents/buffers utilized. The waste tray may be selectively insertable and removeable to enable easy removal of the waste and cleaning.

The instrument 300 of FIG. 10 provides one non-limiting example of the shape the casing 302 may take. In this example, the length of the instrument 300 (from the access door 306 to a rear side 308) is about the same as the height of the instrument 300, and the width of the instrument is about half of the length. These relative dimensions appear to work well in a typical lab setup. However, it will be understood that the components and features of the instrument 300 do not necessitate a particular shape of the casing 302 so long as the internal compartment 304 is capable of receiving the cartridge 301. In other embodiments, the casing 302 may form other shapes such as with other length to height, length to width, and/or width to height ratios.

Further, while the illustrated embodiment is configured to receive cartridges in a substantially vertical orientation, other embodiments may be configured such that the cartridge is inserted at a different orientation. For example, some embodiments may be configured to receive cartridges in a substantially horizontal orientation. Moreover, while the illustrated embodiment is configured to receive one purification cartridge at a time, other embodiments may include multiple compartments each capable of receiving a purification cartridge simultaneously or in an independent manner. Such embodiments may be able to process multiple samples in parallel, for example.

As shown, the access door 306 may be configured with a hinge point 310 disposed near a bottom side 312 of the instrument 300 so that the access door 306 pivots downward to open and upward to close. This configuration allows the access door 306 to rest upon the benchtop when open and provides ready access to the internal compartment 304. Other embodiments may configure the access door 306 differently, such as by including hinge points on an upper side or on right or left sides of the instrument, or by utilizing a sliding-type door or panel assembly. Although an access door 306 is preferred, some embodiments may omit a door.

In the illustrated embodiment, when the access door 306 is open, the inner surface 314 of the access door 306 can function as a guide for directing the cartridge 301 into the internal compartment 304. For example, the user can rest the cartridge 301 on the inner surface 314 and then direct the cartridge 301 into the interior compartment 304 at the appropriate height. The inner surface 314 may also include one or more grooves 316 or other such guiding structures that allow engagement with the cartridge 301 to further assist in correctly positioning the cartridge 301 within the internal compartment 304. Other mechanisms and/or structures for guiding the cartridge into the compartment are envisioned herein, including, for example, a grip mechanism configured to secure the cartridge when it is partially inserted into the compartment followed by a translocation mechanism for further transporting the cartridge into the compartment for processing. Other mechanisms can be used, as known in the art.

The illustrated embodiment also includes a user interface 318 for receiving user input and/or displaying instrument information. The user interface 318 is communicatively coupled to a controller (described in more detail below—see FIG. 20A) to enable communication with and control over various components of the instrument 300. The user interface 318 is configured to receive user input and/or display information related to, for example, a volume of a biological sample placed within the cartridge, cartridge identification information, a selected purification protocol, creation and/or saving of a user defined protocol, sample identification information, instrument identification information, operating instructions for the selectively closable access door 306 or components associated therewith, a desired concentration of the target nucleic acid to be purified, one or more optical density measurements related to the initial sample and/or to the sample at various stages during the purification process, and/or a final volume of eluent comprising the target nucleic acid.

The user interface 318 may be configured to allow interaction with the user through a touchscreen, control pad, mouse, microphone, keyboard, and/or other computer input/output components known in the art. During processing the user interface 318 may provide for the user to observe the progress of a purification process being performed on the cartridge and may provide for alarms to indicate completion of the processing or errors or other problems that may occur during processing.

Instrument Clamping Mechanism

Figure 11A:
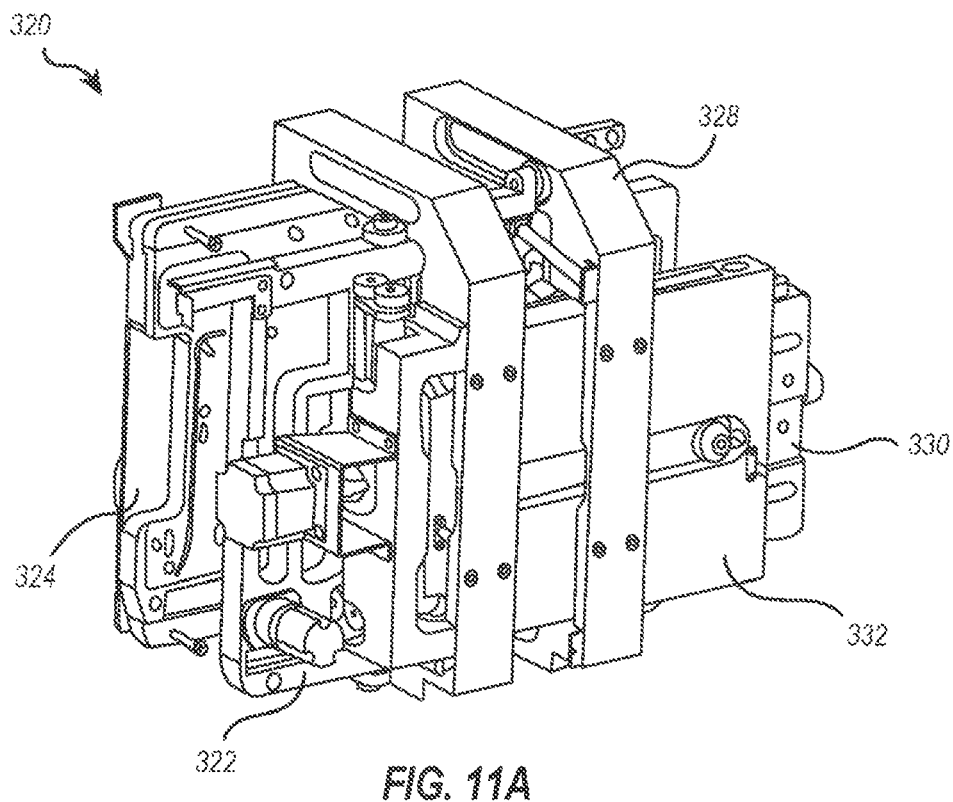
FIGS. 11A and 11B illustrate a clamping mechanism that may be included as part of the purification instrument and utilized to apply a compressive force against an inserted purification cartridge to aid in maintaining the integrity of fluid seals of the cartridge during a purification process.
Figure 11B:
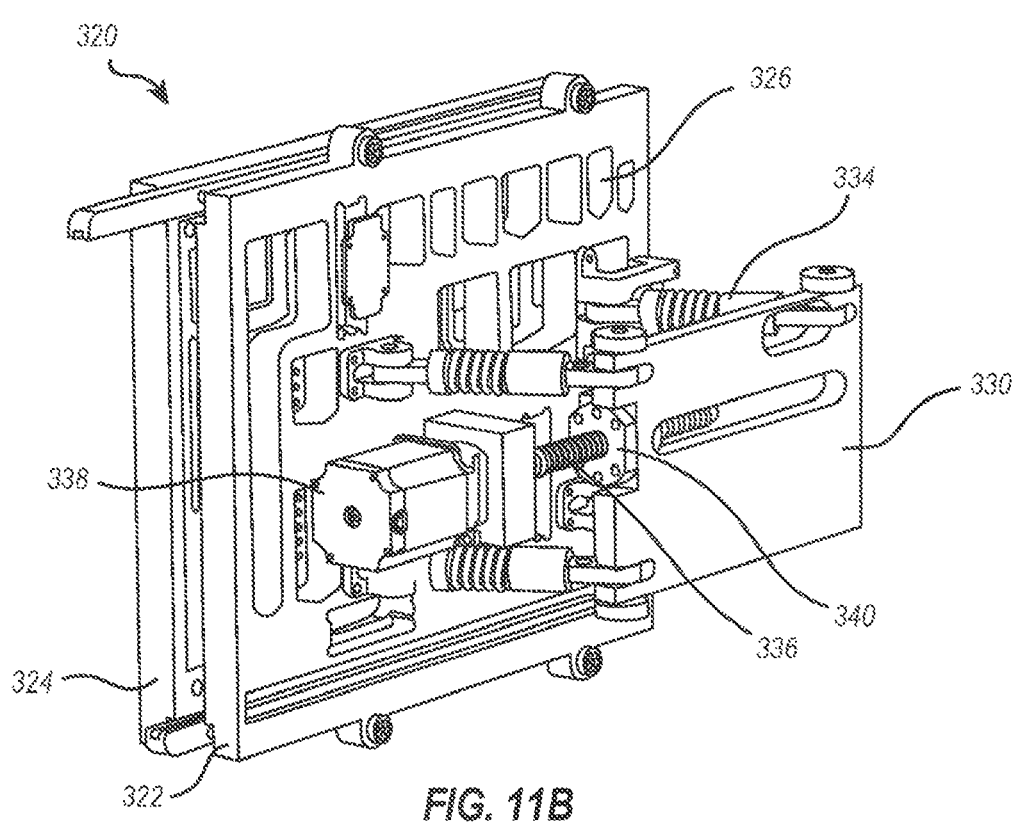

FIGS. 11A and 11B illustrate an embodiment of a clamping mechanism 320 that may be included as part of the instrument 300. In some applications, the instrument 300 may interface with a consumable cartridge having a relatively low-cost construction. That is, a consumable cartridge may be intentionally designed with minimal inherent sealing in order to lower manufacturing complexities and associated costs. For example, the consumable cartridge may be designed with sealing sufficient to maintain fluid separation at ambient pressures but not necessarily at the high pressures experienced during a purification process (e.g., as a result of passing the biological samples, reagents, and/or other fluids through the membrane(s), filter(s), resin(s), and/or bead column(s) for the various separation/filtering process steps).

The consumable cartridge may be designed instead to rely on the clamping mechanism 320 of the instrument 300 to provide sufficient sealing force to enable the cartridge to withstand the high pressures experienced during the purification process. This design approach beneficially allows costs that would otherwise be inherent to the cartridge to be offset to the instrument. It is more economically efficient to place these costs with the durable instrument than with the consumable, single use cartridge.

In FIGS. 11A and 11B, the casing 302 and other components have been removed to better illustrate the clamping mechanism 320. The clamping mechanism 320 includes a first plate 322 and a second plate 324 that are configured to move between an open position (shown in FIG. 11A) and a closed position (shown in FIG. 11B). In the closed position, the plates 322 and 324 compress a cartridge positioned therebetween and provide sufficient clamping force to allow the cartridge to withstand the relatively high pressures involved with a purification process. As best shown in FIG. 11B, one or both of the plates 322 and 324 may include apertures 326 that align with components of the cartridge such as fluid reservoir or channel components of the cartridge. The plates 322 and 324 are thus configured to align with and compress the portions of the cartridge that require compression to maintain seal integrity during the purification process.

As shown in FIG. 11A, the first and second plates 322 and 324 are supported within a frame 328. In this embodiment, the clamping mechanism 320 is configured to move the first plate 322 laterally relative to the second plate 324. That is, the first plate 322 is a translating plate and the second plate 324 is a stationary plate. A foot 330 is disposed within a socket 332 and is capable of being longitudinally translated relative to the socket 332. The socket 332 is attached to and/or is part of the frame 328 and functions to maintain the foot 330 against the perimeter of the internal compartment and prevent lateral movement of the foot 330.

In FIG. 11B, the frame 328 and socket 332 have been removed to better show the foot 330 and its associated mechanisms. As shown, the foot 330 may be coupled to the first plate 322 by one or more linkages 334. Preferably, a plurality of linkages 334 are provided to better distribute the compression force across the first plate 322. The linkages 334 may also include springs to better distribute the lateral compression force of the plates. The linkages 334 may also include various shims to adjust the amount of applied force.

A drive screw 336 is operatively coupled to a motor 338 and threaded through a receiver 340. The receiver 340 is attached to the foot 330 and is threaded so that rotation of the drive screw 336 causes the receiver 340 to longitudinally translate upon the drive screw 336. This causes the foot 330 to move longitudinally. Because the foot 330 is prevented from moving laterally by the socket 332, and because the first plate 322 is prevented from moving longitudinally by the frame 328, the longitudinal movement of the foot 330 causes corresponding lateral movement of the first plate 322.

The ends of the linkages 334 also travel in a cam path which provides additional mechanical advantage against the first plate 322.

Other embodiments may utilize other mechanisms to provide linear motion of the first plate 322. For example, rather than a drive screw, the foot 330 may be operatively coupled to a linear actuator, belt and pulley assembly, chain and sprocket assembly, gear and gear rack assembly, or combination thereof. Some embodiments may include a mechanism that directly pushes and pulls the first plate 322, such as a piston-based mechanism or some other linear actuator mechanism directly applied to the first plate 322. Some embodiments may be configured to move each plate 322, 324 relative to one another rather than have one plate as stationary.

Since some cartridges may need to withstand pressures of up to 50 to 100 psi, the clamping mechanism 320 is configured to apply a total seal force of at least about 500 lbf, or more preferably at least about 1,000 lbf, or even more preferably at least about 2,000 lbf.

Figure 12:
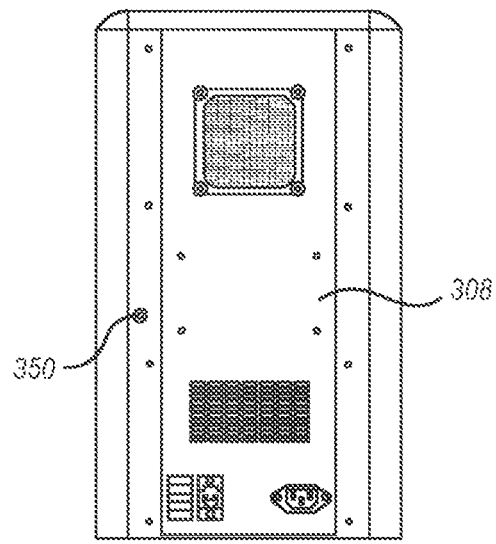
FIG. 12 illustrates a view of a rear side of the purification instrument showing an access point for a manual clamp release mechanism.

If power is lost during the middle of a purification process, the user may utilize a manual release mechanism to disengage the clamping mechanism 320 and allow the cartridge to be removed. A partially processed cartridge may contain biohazards and/or hazardous chemicals that may need to be removed prior to servicing, transport, or further use of the instrument 300. In the illustrated embodiment, as shown in FIG. 12, the manual release mechanism is accessible via an access point 350 located on the rear side 308 of the instrument 300, though the access point 350 may be located at other positions.

The manual release mechanism is configured so that a common tool (e.g., screwdriver, Allen wrench) inserted through the access point 350 contacts the mechanism and allows manual turning of the drive screw 336 by rotating the tool. The manual release mechanism may also be clutched. For example, once the clamp is disengaged, the clamp spring force may begin to push the plates apart and cause the drive screw 336 to rotate rapidly. A one-way bearing associated with the release mechanism may then begin to rotate so as to prevent uncontrolled rotation of the tool used to initiate the manual release of the clamp.

Other instrument embodiments may omit a clamping mechanism. For example, not all cartridges are necessarily manufactured to utilize additional compression from the instrument. For example, where cartridges have sufficient inherent sealing, where the biological sample includes less cells or is otherwise less viscous (e.g., water or urine samples), and/or where the biological sample volume is small relative to the capacity of the instrument (e.g., about 10 ml), the instrument need not necessarily include or use a clamping mechanism. It will be understood that although some samples may be "small" relative to the capacity of the instruments and processed described herein, such samples are still considered to be large relative to conventional purification instruments and processes.

In applications where the instrument omits or does not utilize a clamping mechanism, the associated cartridges may be constructed to inherently withstand the expected pressures involved. Such cartridges will not necessarily be capable of withstanding the high pressures described above (such as where cultures/sample volumes on the order of 50 to 150 ml may be processed through one or more cell capture membranes), but still be of sufficient construction to withstand the relatively lower pressures involved in the aforementioned scenarios. Such cartridges may be formed using polymer materials (e.g., thermoform and/or other suitable polymers) with the two separate sides fused, adhered, and/or mechanically locked together along the edges and any other desired locations.

Instrument Safety Mechanisms

Figure 13:
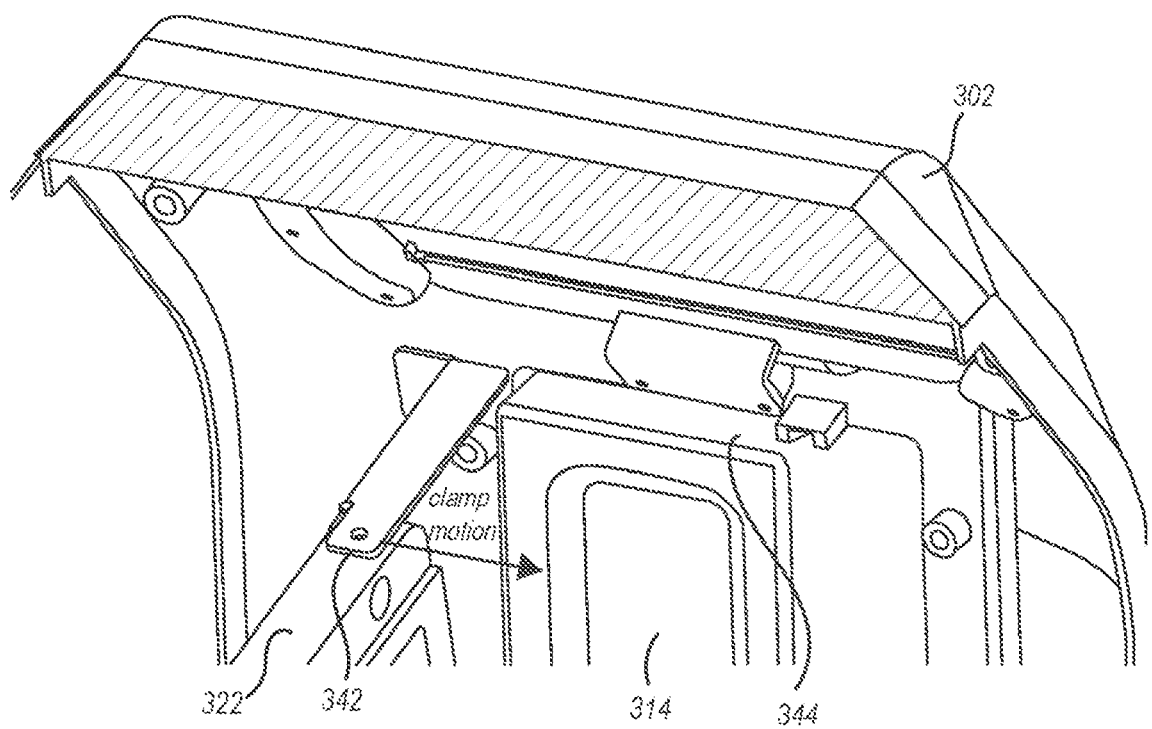
FIG. 13 illustrates an access door locking mechanism from a perspective within an interior compartment of the instrument.

FIG. 13 illustrates a view of a door locking mechanism as seen from a perspective facing the inner surface 314 of the access door 306. A locking tab 342 (also visible in FIG. 11A) is attached to the first plate 322 (i.e., the "moving plate"). A corresponding locking slot 344 is disposed at a portion of the access door 306 that resides within the internal compartment when the door is closed. When the access door 306 is closed and the clamping mechanism 320 is actuated, the locking tab 342 translates with the first plate 322 and thereby enters into the locking slot 344. This prevents the access door 306 from being opened once the clamping process has started.

The illustrated locking mechanism acts as an access barrier that beneficially prevents users from injury due to the various moving parts within the internal compartment. Preferably, the access door 306 is the only opening providing access to the internal compartment. Once closed, the access door 306 and casing 302 form a barrier that separates the user from the automated moving parts within.

Figure 14:
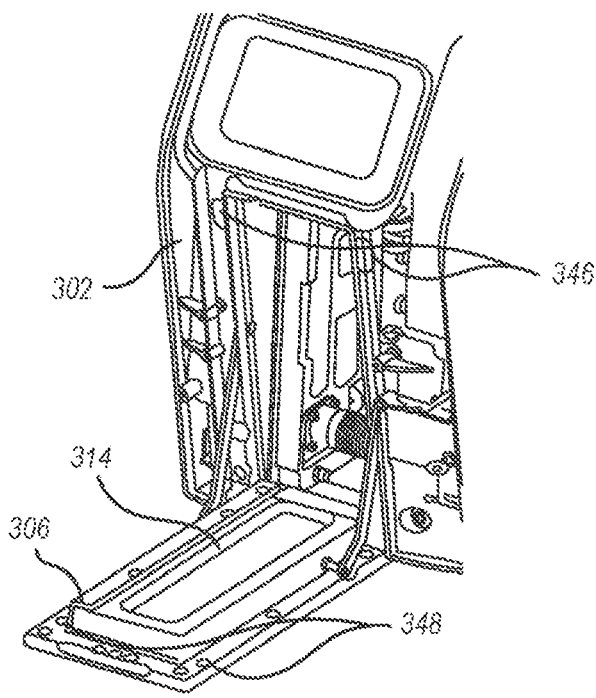
FIG. 14 illustrates an embodiment of an access door sensor assembly.

As an additional or alternative precaution, the instrument 300 may be configured to only allow the clamp motor 338 to be powered when the access door 306 is determined to be closed. This determination may be made using one or more sensors configured to detect whether the access door 306 is open or closed. In the embodiment shown in FIG. 14, the casing 302 includes a pair of redundant Hall effect sensors 346 in a portion of the casing 302 that defines an access door frame. A pair of corresponding magnets 348 are disposed in the access door 306 at positions that align with the Hall effect sensors 346 when the access door 306 is closed.

The positions of the Hall effect sensors 346 and magnets 348 may be reversed such that the magnets 348 are in the access door frame and the Hall effect sensors 346 are in the access door 306. While two pairs of sensors/magnets are shown here, some embodiments may include only a single pair or may include more than two pairs. Other embodiments may additionally or alternatively include other types of contact and/or proximity sensors such as capacitive or inductive proximity sensors, infrared proximity sensors, optical sensors, eddy-current sensors, mechanical switches (e.g., limit switches) or combinations thereof.

Instrument Process Control Mechanisms

The instrument 300 preferably includes one or more features that function to ensure proper preparation of various components prior to initiating a purification process. For example, the instrument 300 may include features that ensure proper positioning of the biomolecule purification cartridge prior to initiating clamping or other steps of the purification process, features that ensure an inserted purification cartridge is unused, and/or features that ensure an output container for receiving purified product is properly positioned.

Figure 15:
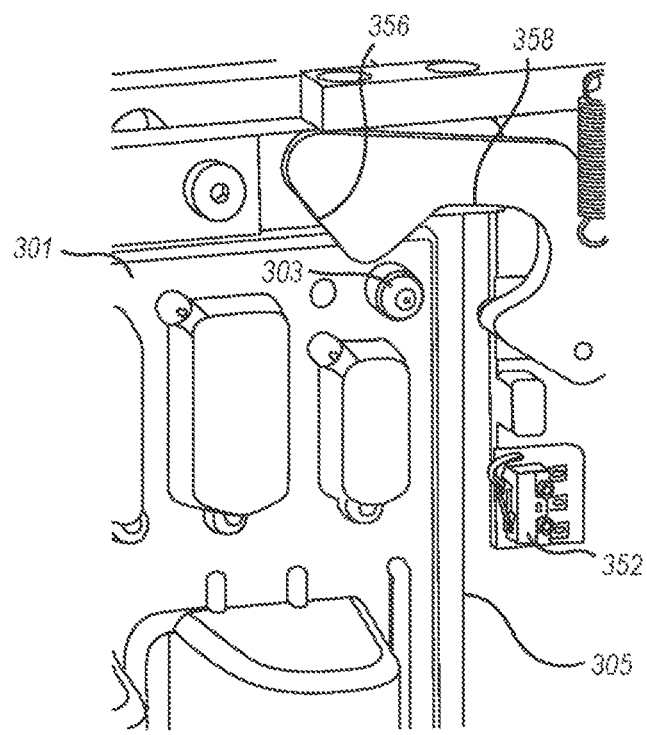
FIG. 15 illustrates a purification cartridge position sensor assembly.

FIG. 15 illustrates an embodiment of a cartridge position mechanism positioned within the internal compartment of the instrument. A contact switch 352 (e.g., a limit switch) may be positioned within the internal compartment at a position where an inserted cartridge 301 will contact the switch 352. In the illustrated embodiment, the contact switch 352 is positioned at the rear side of the internal compartment. In this position, when the cartridge 301 is inserted, its leading edge 305 will advance until it reaches the contact switch 352. The contact switch 352 is communicatively coupled to the instrument controller. The controller may be configured to prevent process initiation unless the contact switch 352 has been contacted.

Other embodiments may position the contact switch 352 at other suitable locations within the internal compartment. Other embodiments may additionally or alternatively include other contact and/or proximity sensors, such as the other types of sensors described herein in relation to other components of the instrument 300 (e.g., optical sensors, magnetic sensors, and the like).

The cartridge position mechanism may also include a latch 354 configured to engage with the cartridge 301 to assist in holding the cartridge in place once inserted to the proper position. The latch 354 may also be configured to provide tactile feedback to the user to indicate to the user that the cartridge is in the proper position. For example, the latch 354 may be spring loaded or otherwise biased toward a closed position and configured to "snap" or "click" back to the closed position after being displaced during cartridge insertion.

In the illustrated embodiment, when the cartridge 301 begins to contact the latch 354 during insertion, an engagement feature 303 of the cartridge 301 can contact an angled surface 356 of the latch 354. Further insertion of the cartridge 301 causes latch 354 to move away from the closed position. Once the engagement feature 303 has cleared the angled surface 356, the groove 358 allows the latch 354 to move back to the closed position. Other embodiments may additionally or alternatively include other latch features such as magnetic couplings, roller catches, ball tension catches, bullet catches, and other latch mechanisms known in the art.

Figure 16:
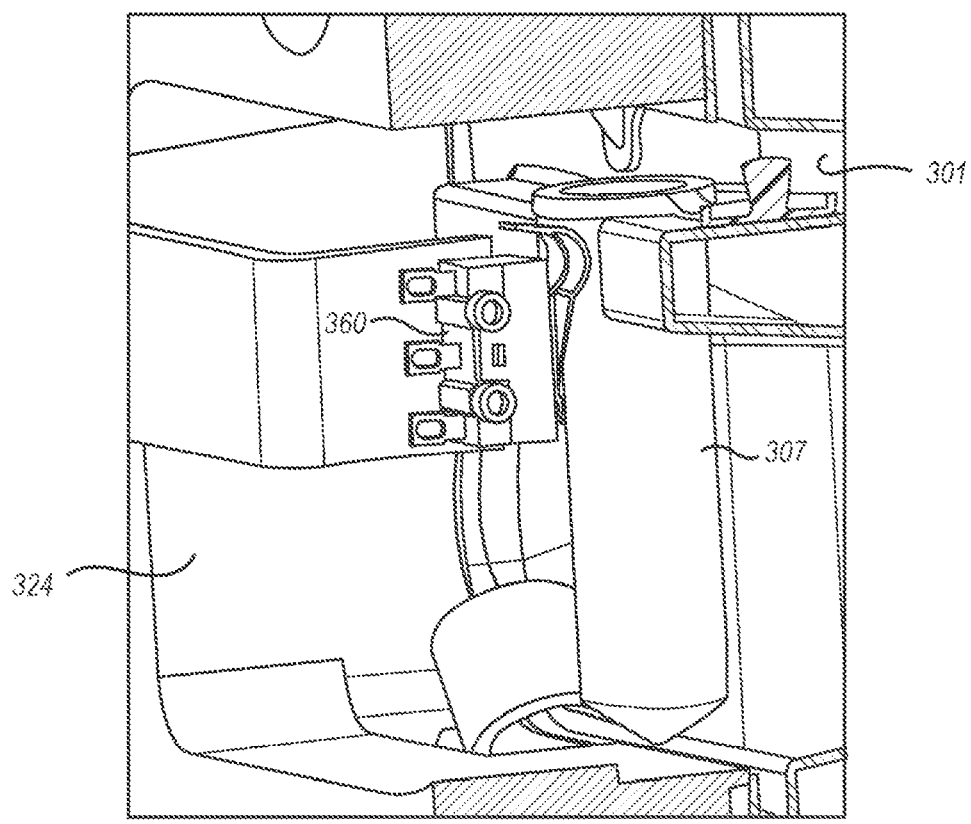
FIG. 16 illustrates an output container presence sensor assembly.

FIG. 16 illustrates another process control mechanism that the instrument 300 may include. Purification cartridges typically include an output container for collecting the purified product. Often, users will remove the output container prior to inserting the cartridge into the instrument in order to, for example, label the output container. However, if the user were to forget to reposition the output container in the cartridge and the cartridge was inserted and the purification process initiated, the valuable purified product would be dispensed onto the instrument floor. This would waste the valuable product and likely create a mess that would require cleanup before the instrument could be used again.

In the embodiment shown in FIG. 16, a contact switch 360 is mounted to one of the plates (the second plate 324 in this example) and positioned to contact an output container 307 when the output container 307 is properly positioned in the cartridge 301. The contact switch 360 ensures that the output container 307 is properly positioned before the purification protocol is started. For example, the contact switch 360 may be communicatively coupled to the controller and the controller may operate to prevent protocol initiation and/or provide a status notification to the user if the contact switch 360 determines that the output container 307 is absent. Other embodiments may additionally or alternatively include other contact and/or proximity sensors, such as the other types of sensors described herein in relation to other components of the instrument 300.

The instrument 300 may also include one or more optical density sensors configured to determine an initial optical density (e.g., OD600 or A600) of a biological sample (e.g., a bacterial culture or other cell culture) that has been inserted into the purification cartridge. The optical density may be determined by illuminating the sample using light of a known wavelength (typically about 600 nm, though other wavelengths may be utilized according to sample type, measurement target, and/or other particular application needs) and measuring the amount of light that passes through the sample and reaches a detector on the opposite side of the sample. Optical sensors may also be utilized to measure the concentration of nucleic acid in the sample (e.g., using wavelengths of 230, 260, and/or 280 nm) at the end of the purification process and/or at intermediate portions of the process.

The instrument 300 may also include one or more additional sensors to monitor protein purity or concentration by absorbance at 210 or 280 nm, or a ratio of absorbance at different wavelengths, assessment of apoenzyme vs holoenzyme status with cytochrome, heme, and other cofactors or prosthetic groups. In some embodiment, additional, or alternative, sensors may be included to monitor pH, conductivity, refractive index, osmolarity, oxidation reduction potential, or protein aggregation.

The optical density (OD) information obtained by the optical density sensor may be reported to the user and may be utilized to inform the user the whether the biological sample falls within a range suitable for processing. For example, the optical density sensor may be communicatively coupled to the controller, and the controller may operate to provide a notice to the user and/or to prevent furtherance of the protocol if the measured OD falls outside of a preferred range.

As explained in more detail further below, the OD reading may also determine and/or initiate particular purification protocols better optimized for a given biological sample type. For example, the buffers/reagents used for purification of the target nucleic acid may be dispersed in different volumes based on the determined OD of the sample. In another example, the timing/duration of sample mixing and/or of passing through one or more membranes/filters of the cartridge may also vary according to the determined OD of the sample. Optical density sensors may be situated at various locations for taking measurements of the sample at various sections of the cartridge and at various stages in the purification process. For example, an optical density sensor may be utilized to determine whether a fluid is present within a particular portion of the cartridge by, for example, comparing the measured OD to an expected air blank.

The OD information may additionally or alternatively be utilized to determine whether an inserted cartridge has been previously used. For example, certain protocols may require an OD reading prior to placing the biological sample into an input reservoir of the cartridge. An initial OD reading of the cartridge prior to placing any sample into the cartridge should be substantially equal to an air blank reading. A higher reading may indicate that the input reservoir of the cartridge has previously been unsealed/broken and filled with a biological sample. For example, the previous sample would likely leave a residue on the sample chamber windows. In such a circumstance, the controller may operate to provide a notice to the user and/or to prevent furtherance of the protocol.

Figure 17:
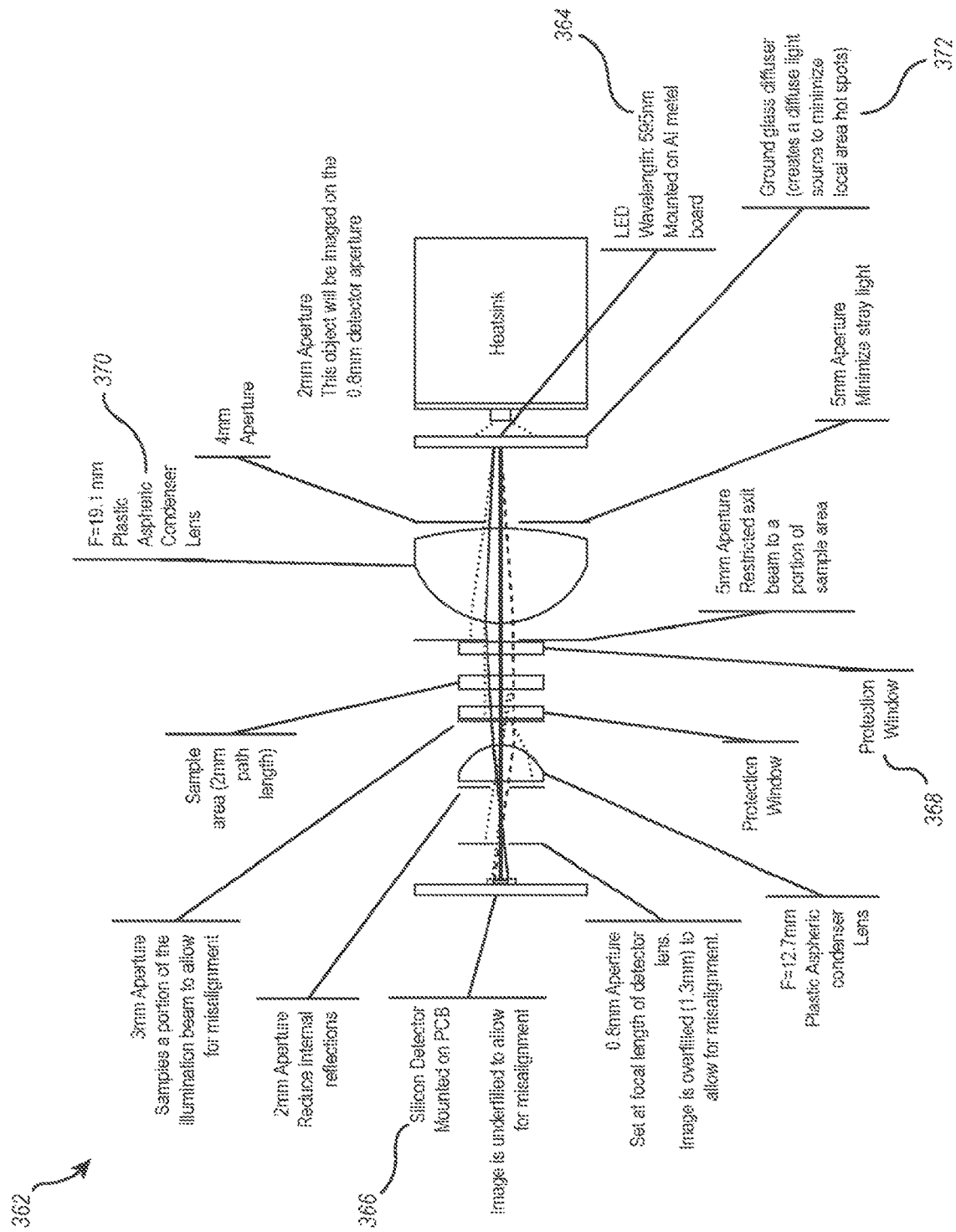
FIG. 17 illustrates an embodiment of an optical density sensor that may be included in the instrument to measure an optical density of a biological sample inserted into a purification cartridge.

FIG. 17 schematically illustrates one embodiment of an optical density sensor 362. The illustrated embodiment includes a light source 364 configured as a light-emitting diode (LED) mounted on an aluminum board and having wavelength of 595 nm. A detector 366 configured as a silicon detector mounted on a printed circuit board (PCB) is disposed opposite the light source 364. A sample chamber, in which a portion of the biological sample 309 fills, is disposed between the light source 364 and the detector 366. The sample chamber includes windows 368 through which the emitted light can pass. The optical density sensor 362 may also include one or more additional optical components such as lenses 370, diffusers 372, filters, apertures, and/or other optical components.

The illustrated embodiment is only one example of a suitable optical density sensor. Other optical density sensor configurations as known in the art may also be utilized. For example, other embodiments may include alternative light source types, alternative detector types, alternative lensing, filtering, and/or aperture arrangements, an alternative light path, or alternative sample chamber dimensions. As mentioned above, one or more optical density sensors may also be utilized at different wavelengths for providing different information about the sample. For example, one or more sensors may be utilized for measuring a concentration of nucleic acid using a suitable wavelength (e.g., 230, 260, and/or 280 nm).

Instrument Pump Assemblies

Once a purification cartridge has been inserted into the instrument 300 and a purification process has been initiated, the instrument 300 will operate to move and route fluids through the cartridge using a series of pump assemblies. The pump assemblies are disposed so as to engage with the purification cartridge (e.g., when the clamping mechanism is closed) to controllably direct fluid during the purification process. Pump assemblies may be disposed so as to be upstream and/or downstream of each processing section (e.g., each membrane or filter) of the cartridge. That is, pump assemblies may be positioned to "push" the sample, reagents, or other fluids of the process further downstream, to "pull" the sample, reagents, or other fluids of the process further downstream, or both. The pump assemblies described herein are beneficially able to move and route fluids of various viscosities and densities.

Figure 18A:
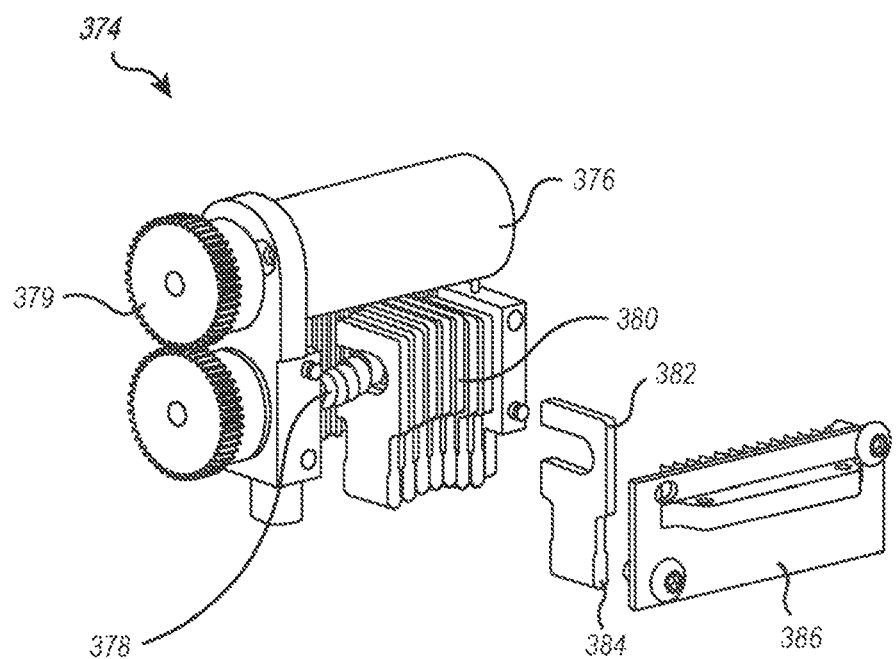
FIGS. 18A and 18B illustrate a pumping assembly that may be included as part of the purification instrument and utilized to move and route fluid along a fluid path of an inserted purification cartridge.

FIG. 18A illustrates an exemplary pump assembly 374 (in partially exploded view). The pump assembly 374 includes a motor 376 operatively coupled to a camshaft 378 via a power transmission assembly. The power transmission assembly may include gears 379, as shown, and/or may include one or more other power transmission components such as belts, pulleys, chains, sprockets, and the like.

Attached to the camshaft 378 are a plurality of cam elements 380 (i.e., "fingers"). As shown, each cam element 380 includes an attachment end 382 configured to attach to the camshaft 378 and a tip 384 that extends transversely (e.g., perpendicularly) away from the camshaft 378. The cam elements 380 are arranged on the camshaft 378 such that rotation of the camshaft 378 causes linear peristaltic motion of the cam element tips 384. The cam elements 380 and/or other components of the pump assembly 374 may be disposed within a housing 386.

Figure 18B:
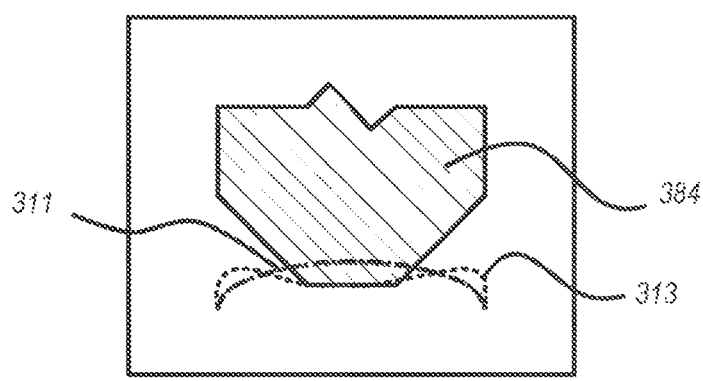

FIG. 18B is an expanded view of a cam element tip 384 in contact with a fluid channel 311/313 of a cartridge. Here, the fluid channel prior to deflection is shown as 311 and after deflection is shown as 313. The tip 384 may be beveled to provide effective engagement with the fluid channel 311/313, though other cam element shapes may be utilized depending on particular application needs and preferences. As illustrated, movement of the cam element 380 against the fluid channel 311/313 causes the fluid channel to deflect and thereby displace fluid contained within that portion of the fluid channel 311/313.

FIGS. 19A through 19F illustrate engagement of the pump assembly 374 with a fluid channel 315 of the cartridge 301 and show sequentially how the linear peristaltic motion of the cam elements 380 can drive fluid movement through the fluid channel 315. FIGS. 19A through 19D illustrate a cross-sectional plan view from a perspective normal to the side face of the pump assembly 374.

Figure 19A:
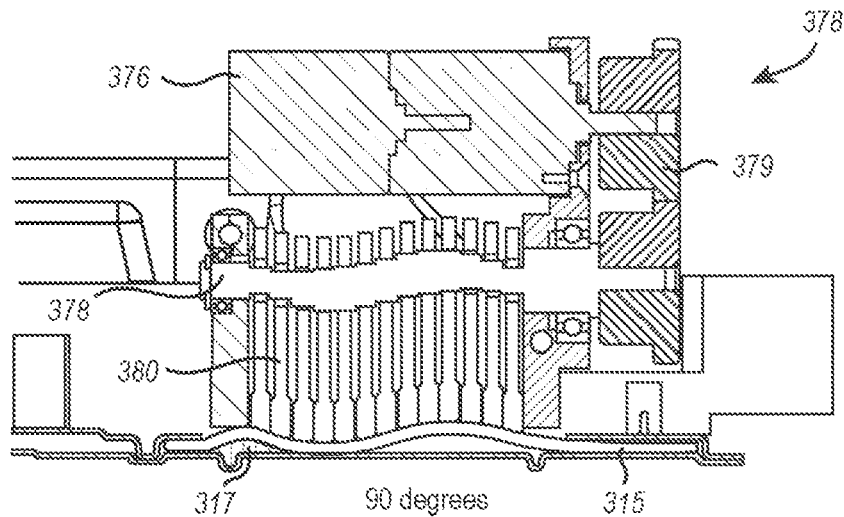
FIGS. 19A through 19F illustrate sequentially the movement of fluid through a fluid channel of a purification cartridge as a result of actuation of a pump assembly engaged with the fluid channel.
Figure 19B:
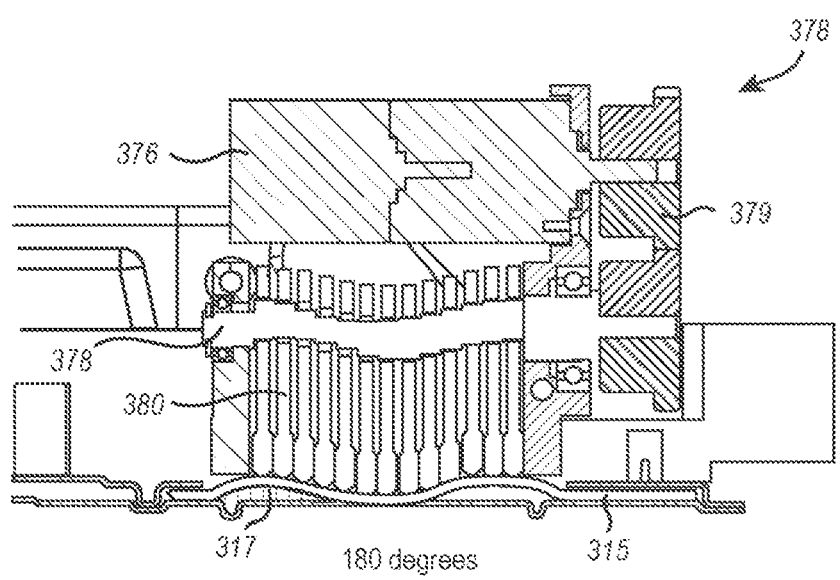
Figure 19C:
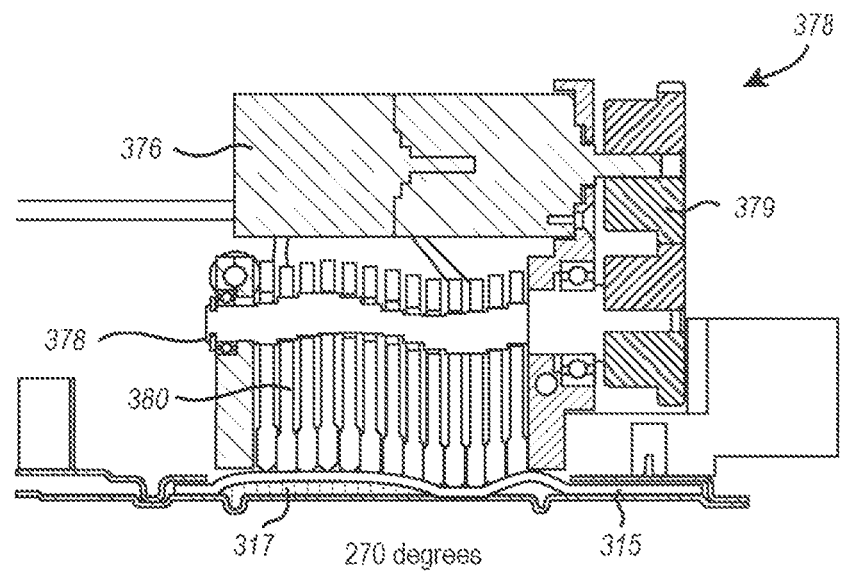
Figure 19D:
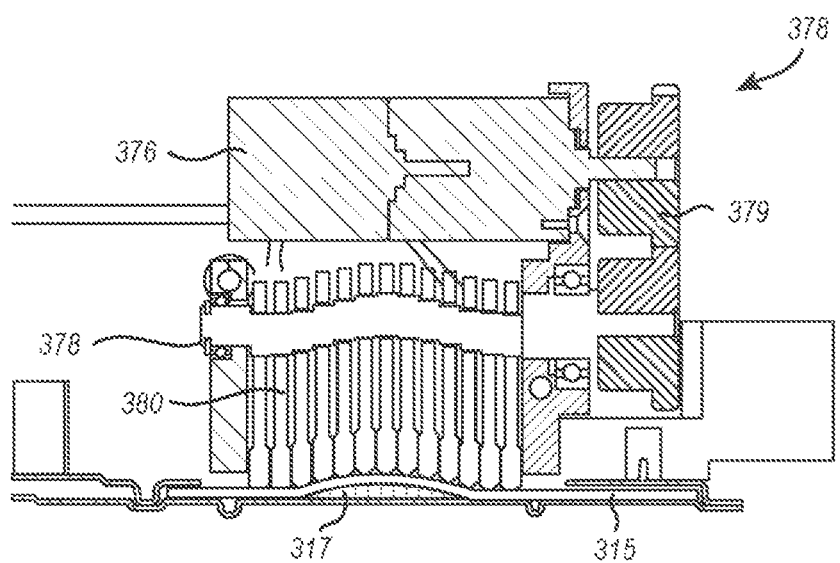
Figure 19E:
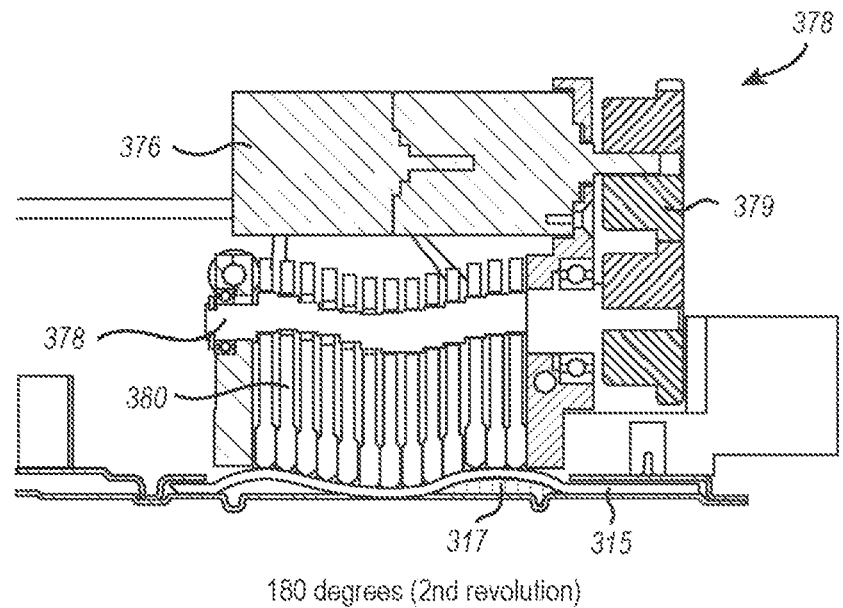
Figure 19F:
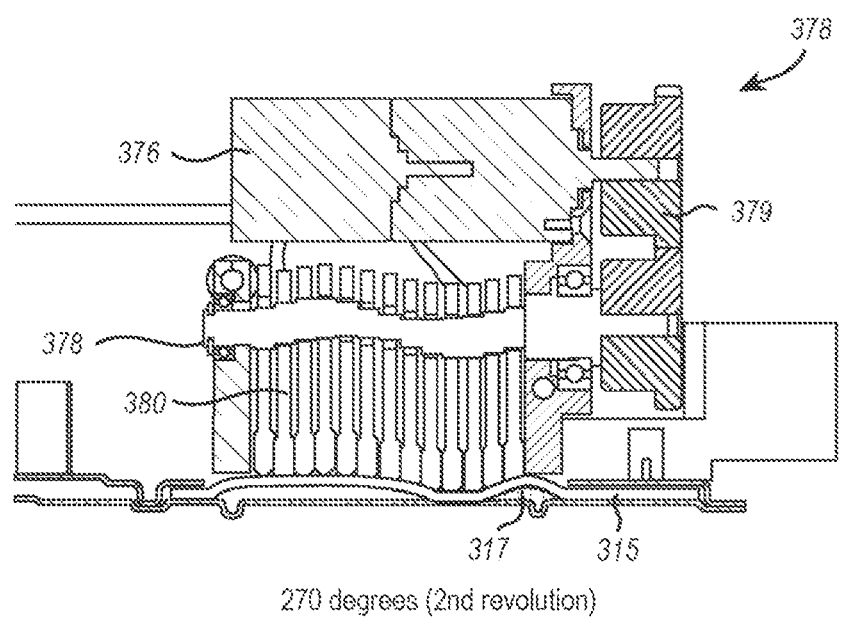

FIG. 19A shows the pump assembly 374 with the camshaft 378 at an arbitrary 90-degree position. As the camshaft 378 continues to rotate to a 180-degree position shown in FIG. 19B, a 270-degree position shown in FIG. 19C, and then to a 0 (i.e., 360) degree position shown in FIG. 19D, the sequential engagement of the cam elements 380 against the fluid channel 315 causes the fluid 317 to move through the fluid channel 315. As the camshaft 378 continues to rotate through additional rotations, the cam elements 380 continue to engage with the fluid channel 315 in a corresponding peristaltic fashion to further direct the fluid 317 through the fluid channel 315, as shown in FIGS. 19E and 19F.

One exemplary embodiment of a pump assembly was shown to move about 0.16 ml of fluid (e.g., about 0.05 to 0.45 ml) per rotation of the camshaft. At a motor RPM of 136, the generated flowrate was about 22 ml/min (e.g., about 10 to 35 ml/min). Of course, different flowrates may be achieved using different motor speeds, different fluid channel dimensions, different number or orientation of cam elements, different fluid viscosities, and the like.

The pump illustrated pump assemblies beneficially enable movement of fluids of varying viscosities and densities. However, other embodiments may additionally or alternatively include other means of fluid transport. For example, a pump assembly may utilize a roller mechanism that compresses the fluid channel and then moves linearly across the fluid channel to move fluid.

Instrument Control Systems

Figure 20A:
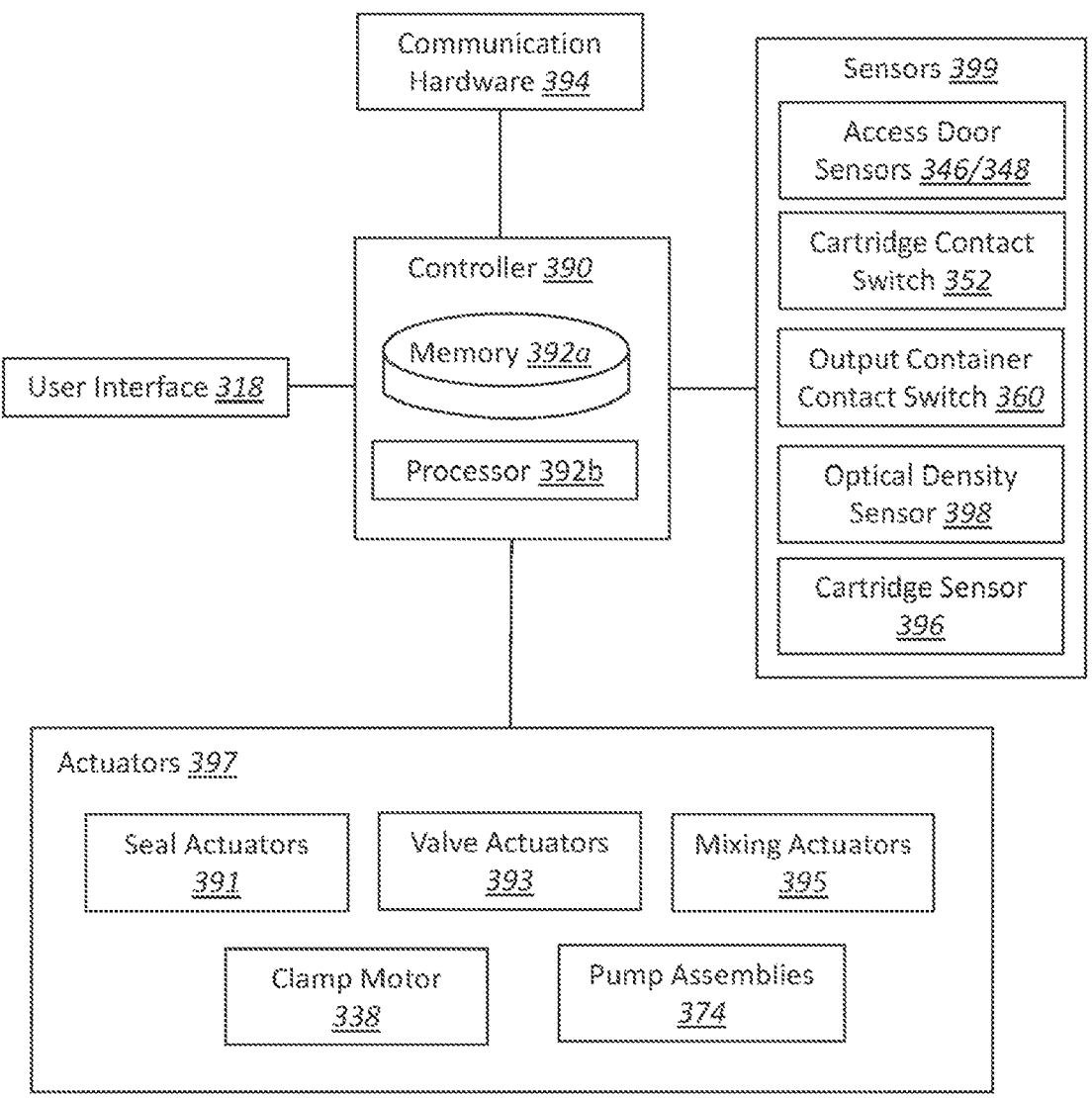
FIG. 20A illustrates a control system that may be included with the instrument and utilized to control various components of the instrument, receive user input, display data, and communicate with other computer devices and/or networks.

FIG. 20A schematically illustrates an exemplary control system 388 that may be utilized to control various components and operations of the instrument 300. The controller 390 includes memory 392a (i.e., physical storage media or hardware storage devices) and one or more processors 392b (and/or suitable microcontrollers). As described above, the controller 390 may be communicatively coupled to the user interface 318 to receive user input through the user interface 318 and to send display information to the user interface 318.

The controller 390 may also be communicatively coupled to one or more sensors 399, such as the position sensors described herein including access door sensors 346/348 (e.g., Hall effect sensors), cartridge contact switch(es) 352, output container contact switch(es) 360, and the optical density sensor 398 (or a plurality of such sensors). As described above, the controller 390 may operate to send a user notification and/or pause or stop the purification process based on the determined state of such sensors.

For example, as described above in relation to the optical density sensor 398, the controller 390 may be configured to receive OD information and send a user notification indicating the OD information and/or how the associated OD measurement relates to a preferred protocol range. In some embodiments, the controller 390 may be configured to indicate whether an inserted cartridge has been previously used based on OD information received from the optical density sensor 398 and may be configured to send a notification and/or halt a purification process accordingly.

The controller 390 may also be communicatively coupled to cartridge sensor 396 configured to interface with an inserted cartridge to obtain identification information from the cartridge. For example, the cartridge 396 may include a barcode reader and/or other suitable sensor capable of reading an identifier or code placed on the cartridge. Identification information may include a lot number, expiration date, stock keeping unit number, type of cartridge, number of uses associated with the cartridge, number of available uses associated with the cartridge, etcetera.

The instrument need not be limited to the number and/or types of sensors illustrated. For example, some embodiments may additionally or alternatively include one or more flow rate sensors, temperature sensors, time lapse sensors, volume sensors, weight sensors, and/or other sensor types for measuring other parameters of the purification process.

The controller 390 may also be communicatively coupled to one or more actuators 397 such as the clamp motor 338 to control actuation of the clamping mechanism and the pump assemblies 374 to control fluid movement through the cartridge via the pump assemblies 374. The set of actuators 397 may also include one or more seal actuators 391 and/or valve actuators 393 which are configured to selectively break fluid seals in the cartridge and control opening and closing of valves in the cartridge, respectively (and which are described in greater detail elsewhere herein). The set of actuators 397 may also include one or more mixing actuators 395. In a preferred embodiment, a mixing actuator includes a rotatable magnet positioned to align with corresponding magnetic stir elements disposed within mixing chambers of the cartridge.

The controller 390 may also be communicatively coupled to communication hardware 394. The communication hardware 394 may include a router and/or other networking hardware configured to provide communication with one or more of a network (e.g., a local area network (LAN), wide area network (WAN), cloud-based network), external server system, external computer device, distributed computer system, and the Internet through a wired or wireless connection. The communication hardware 394 may also include components that allow for upload or download of data via direct connection, such as an ethernet port, a Personal Computer Memory Card International Association (PCMCIA) slot or a universal serial bus (USB) port, or the like.

In some embodiments, the controller 390 is configured to automatically vary a purification protocol based on input received from one or more sensors as part of a "smart" purification system. For example, a determined optical density of the input sample may be utilized to adjust one or more operational parameters of the purification procedure. Such variable operational parameters may include, for example, the volume of one or more reagents moved by the instrument to be used in the purification procedure, the timing of pumping, and/or the speed of pumping via the actuation of the pumping assemblies. By way of example, a cell capture/filtering step will typically be performed as an initial part of a purification procedure. This cell capture/filtering step may preferably be carried out for a longer period of time when the optical density of the input sample is higher. As another example, the use of higher volumes of one or more reagents may be preferred when the optical density of the input sample is higher.

The control system 388 can additionally enable communication with a user inventory database to track the usage and availability of consumable products (e.g., buffers, reagents, cartridges) within the user's organization or laboratory. The control system or user inventory database may be associated with one or more rules that prompt the user to purchase additional consumable goods (or simply cause a purchase to be made) when a threshold or trigger condition is met, such as where available inventory falls below a threshold level. It should also be appreciated that any number or type of trigger conditions associated with systems described herein can be pre-determined and/or changed to meet individual user requirements or preferences.

Figure 20B:
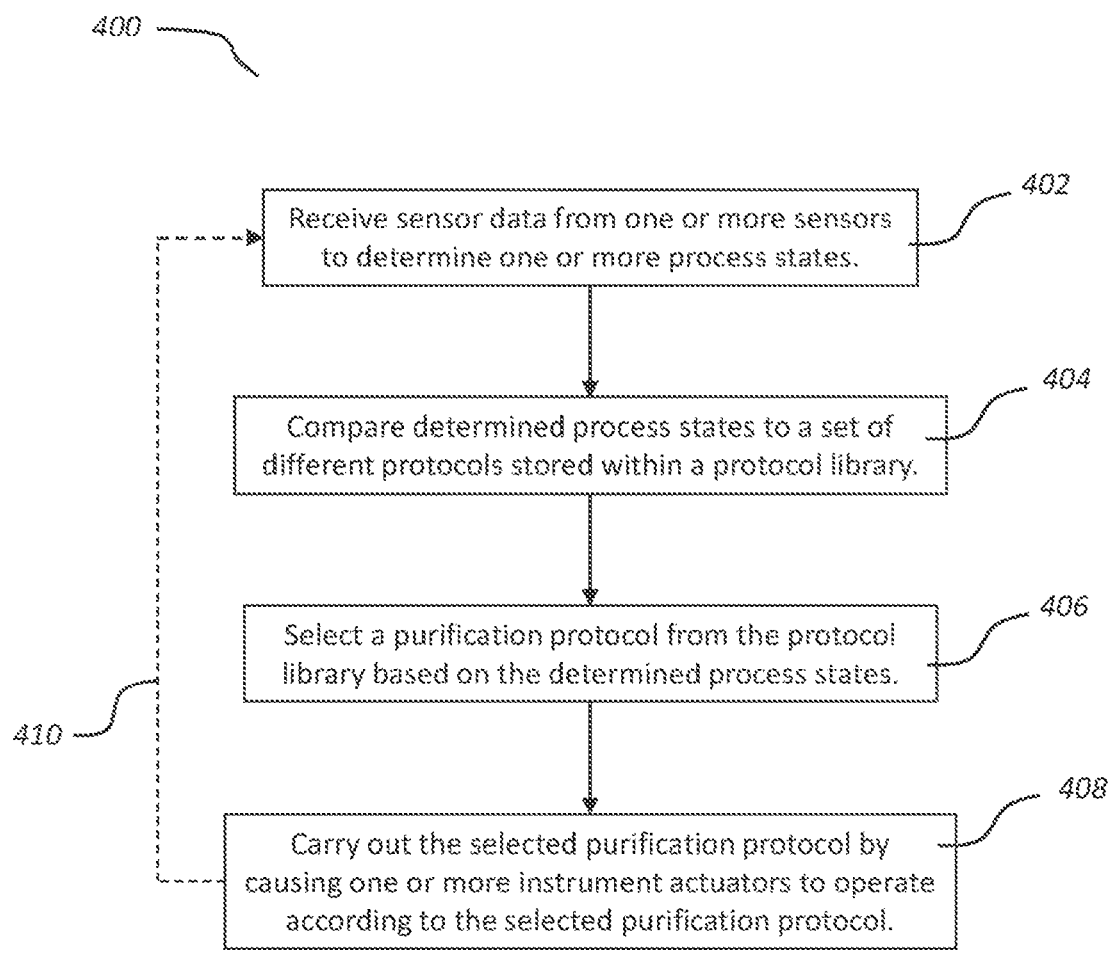
FIG. 20B illustrates an exemplary method that may be implemented by the control system of FIG. 20A to select a purification protocol based at least in part on received sensor data and to carry out the selected purification protocol.

By way of further example, FIG. 20B illustrates an exemplary method 400 for carrying out a purification procedure. The method 400 may be implemented using a suitable computer control system, such as the control system 388 shown in FIG. 20A. In the illustrated method 400, the control system may be configured to receive sensor data from one or more sensors to determine one or more process states (step 402). The one or more sensors may include, for example, any or all of the sensors 399 shown in FIG. 20A and/or other sensors described herein, such as temperature sensors, volume sensors, weight sensors, cartridge scanners (e.g., barcode or QR code scanners), etcetera. The process states may include any of the measurements made by such sensors. Process state data may additionally include information input by the user and/or obtained from the particular cartridge, such as cartridge type (e.g., anion exchange and precipitation or silica-based capture), sample type (e.g., cell culture, environmental, clinical, food, or forensic sample), and the like.

The control system may then compare the determined process states to a set of different protocols stored within a protocol library (step 404). The protocol library may be stored within the memory 392a of the controller 390, and/or may be accessed by way of network communication between the controller 390 and one or more server systems, "cloud" databases, or the like. The protocol library includes different purification protocols associated with different possible process states. For example, the protocol library may include a purification protocol associated with a "low" initial OD reading, a different purification protocol associated with a "medium" initial OD reading, and a different purification protocol associated with a "high" initial OD reading. Of course, the number of different protocols need not be limited to low/medium/high categorizations, but could, for example, be distinguished based on numerical ranges with any desired level of granularity.

Each separate purification protocol can define the desired process steps and parameters for carrying out the purification process. For example, a purification protocol may define whether cell capture and/or cell lysis is utilized, the duration of cell capture and/or cell lysis, which reagents to utilize, volumes of reagents to utilize, whether and/or when to perform mixing at one or more purification steps, duration and/or speed of one or more mixing steps, duration and/or speed of pumping between one or more purification steps, whether and/or when to open and close one or more valves within the cartridge, whether and/or when to puncture one or more seals within the cartridge to allow corresponding release of fluid or venting of gas, a type of nucleic acid capture involved, a duration of the nucleic acid capture, a type of protein to be captured, duration of target protein capture, or combinations thereof.

The control system may then select a purification protocol from the protocol library based on the determined process states (step 406). The purification protocol may be selected as a best match for the particular set of determined process states, for example, or as the only match within a set of purification protocols with mutually exclusive corresponding process states.

The control system may then carry out the selected purification protocol by causing one or more instrument actuators to operate according to the selected purification protocol (step 408). The one or more instrument actuators may include any or all of the actuators 397 illustrated in FIG. 20A. By way of example, if the selected purification protocol calls for a particular mixing speed and/or duration at a particular process step, the controller 390 causes the appropriate mixing actuator(s) 395 to operate accordingly to thereby carry out that portion of the selected purification protocol. In another example, if the selected purification protocol calls for particular volumes of reagents to be used and to be released at particular times during the purification procedure, the controller 390 causes the associated seal actuators 391, pump assemblies 374, and/or valve actuators 393 to operate accordingly to thereby appropriately route and utilize the reagents according to the selected purification protocol. In another example, if the selected purification protocol calls for a particular call capture duration (e.g., as estimated based on an initial OD reading), the controller 390 causes the associated seal actuators 391, pump assemblies 374, and/or valve actuators 393 to operate accordingly to allow the appropriate duration of the cell capture step.

In some implementations, the method 400 may operate iteratively. As indicated by arrow 410, as a selected purification protocol is being carried out, the controller 390 may continue to receive additional sensor data to determine one or more updated process states. The updated process states may then be compared to the protocol library and the purification protocol may be updated/revised "on the fly" according to the more recently obtained measurements. This beneficially allows the purification procedure to re-optimize between each process step based on the results of the previous process step. For example, if following a cell capture step the sensor data indicates that a smaller volume of lysate was collected than was expected based on the initial OD reading of the input sample, the initially selected purification protocol may be updated/revised to better align subsequent usage and/or timing of reagents, mixing, pumping, and the like with the measured amount of lysate.

The control system 388 of the present disclosure may comprise, utilize, or communicate with special purpose or general-purpose computer(s) including computer hardware. The control system 388 within the scope of the present invention can also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media (e.g., hardware storage devices). Computer-readable media that carry computer-executable instructions are transmission media. Thus, by way of example, and not limitation, embodiments of the invention can comprise at least two distinctly different kinds of computer-readable media: computer-readable hardware storage media and transmission computer-readable media.

Computer-readable hardware storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry desired program code in the form of computer-executable instructions or data structures and which can be accessed by a general purpose or special purpose computer. Combinations of the above are also included within the scope of computer-readable media.

Further, upon reaching various computer system components, program code in the form of computer-executable instructions or data structures can be transferred automatically from transmission computer-readable media to computer-readable hardware storage media (or vice versa). For example, computer-executable instructions or data structures received over a network or data link can be buffered in RAM within a network interface module (e.g., a "NIC"), and then eventually transferred to computer system RAM and/or to less volatile computer-readable hardware storage media at a computer system. Thus, computer-readable hardware storage media can be included in computer system components that also (or even primarily) utilize transmission media.

Computer-executable instructions comprise, for example, instructions and data which cause a general-purpose computer (e.g., destination computing devices), special purpose computer (e.g., sensor caps and/or destination computing devices), or special purpose processing device to perform a certain function or group of functions. The computer-executable instructions may be, for example, binaries, intermediate format instructions such as assembly language, or even source code.

The functionality described herein may additionally or alternatively be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etcetera.

Furthermore, wireless communication between any of the disclosed computer systems can be performed using any wireless protocol known in the art, including, for example, Bluetooth, ZigBee, ultra-wideband (UWB), and Wi-Fi. Accordingly, it should be appreciated that if a particular wireless protocol (or associated components) is particularly noted or described within any of the disclosed embodiments, the particular wireless protocol noted can be interchanged with any other wireless protocol known in the art while maintaining any disclosed functionality and/or performing the same or a substantially similar task associated therewith.

Fluidic Seal and Valve Mechanisms

The following disclosure relates to exemplary embodiments of a target biomolecule purification cartridge, such as a target nucleic acid purification cartridge or a target protein purification cartridge, that may be utilized in an automated purification process for the selected target biomolecule. The fluidic seal and valve embodiments may be utilized with other components described herein. For example, the seal and valve components may be integrated with a consumable (e.g., single use) purification cartridge such as described above, utilized with a target biomolecule purification instrument (such as a target nucleic acid purification instrument or a target protein purification instrument) such as described above, and/or included with one or more fluid release mechanisms as described above. In a preferred embodiment, the fluidic seals, valve mechanisms, flow path tubing and connections, fluid reservoirs, and membranes/filters are designed to minimize or eliminate leachables that may contaminate or covalently modify the purified biomolecule, particularly purified target proteins.

Seal and Valve Mechanisms Overview

The conventional nucleic acid purification procedure or protein purification procedure is a manual lab process requiring relatively high levels of lab technician know-how and time. Some previous attempts to automate steps of the purification process have turned to sample-carrying cartridges typically formed as rigid polymer cartridges. Because of the need to route fluids in particular amounts and at particular times, to mix fluids, and to control passage of the fluids through the cartridge to successfully perform the purification procedure, such cartridges are often relatively complex and expensive, and this is particularly true where large sample volumes are involved.

In particular, disparate fluid types must be fluidically sealed and kept from one another until an appropriate mixing step is called for. Challenges associated with maintaining these fluidic seals are exacerbated by the need to move fluids in relatively complex patterns and under different time parameters. For example, pumping the fluids to cause desired fluid routing causes associated pressure differentials which can stress the fluidic seals required to separate the different fluid channels of the cartridge. To prevent leaks, conventional cartridges are formed with seals able to inherently withstand these pressure differentials, which can add significantly to the component and/or manufacturing expenses of the cartridges. For example, to make long lengths of fluid tight seals often requires complex lengths of ultrasonic welds between injection molded parts. These expenses make "consumable," "disposable," "one-time use" or "single use" cartridges less economically feasible despite the potential for greater convenience and time savings such cartridges could provide to the user.

Thus, designing a purification cartridge capable of providing effective fluidic sealing and valving faces several challenges. As described in more detail below, the purification cartridges described herein are capable of meeting one or more of the above-mentioned challenges by utilizing effective seal and valve mechanisms. For example, as described in more detail below, a purification cartridge may include an elastomer layer positioned between two relatively more rigid external layers. The elastomer layer includes a plurality of ribs that fluidically seal fluid channels formed in one or both of the external layers when the elastomer layer is compressed between the two external layers.

This construction beneficially allows the use of less expensive materials and simpler manufacturing methods. For example, such a cartridge does not require long lengths of fluid tight seals and therefore does not need long, complex lengths of ultrasonic welds. By offloading compression functions to an external instrument or component, the costs are beneficially shifted from the cartridge (which typically has much more limited use) to a more permanent device.

As an additional benefit, the elastomer layer may be utilized to provide valving functionality. Thus, only one component is required to form the basis of all the cartridge valves, as opposed to separate, individual components for each valve. These benefits and the structural components capable of providing them are described in more detail below.

Sealing Ribs

Figure 21:
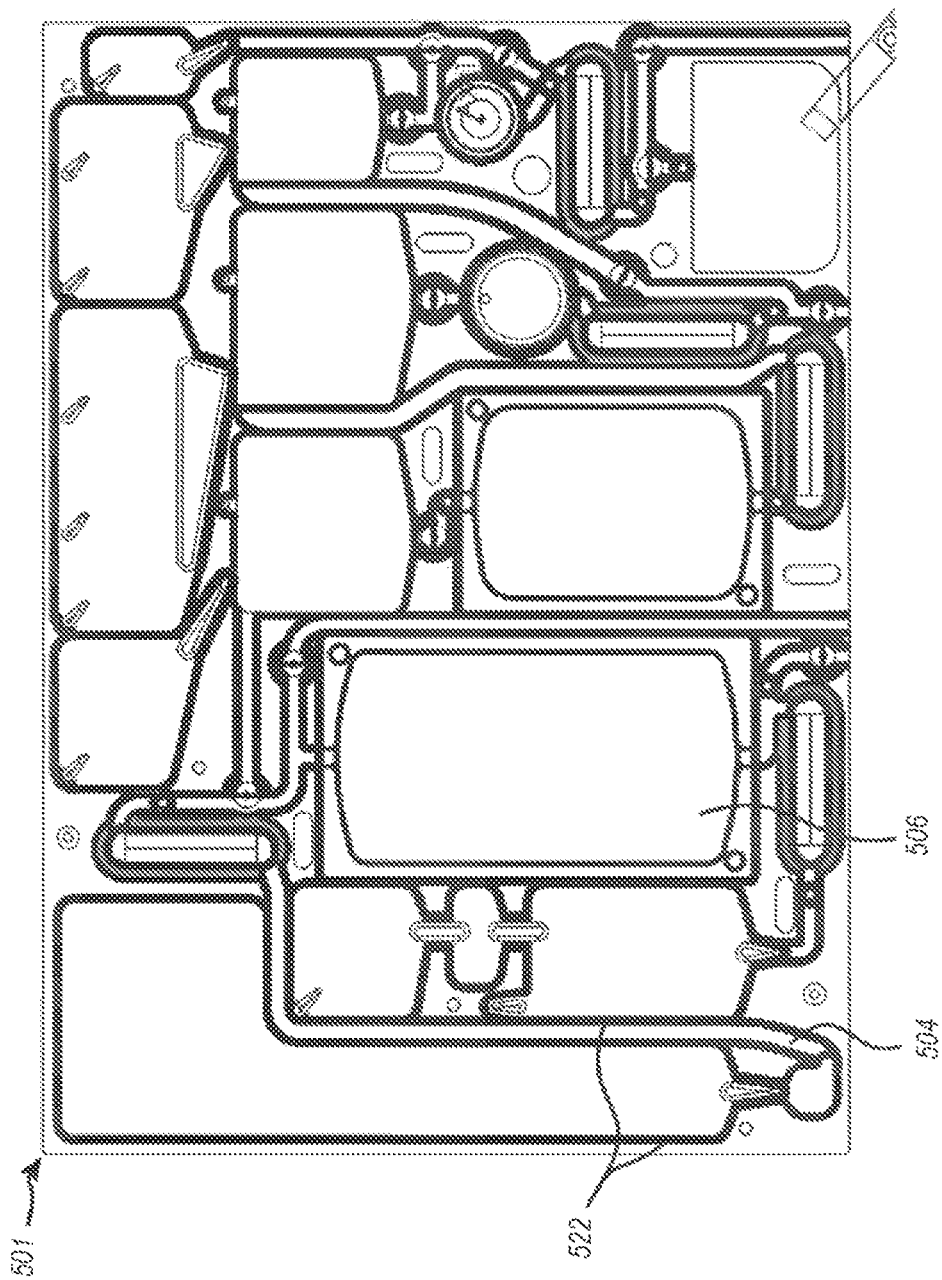
FIG. 21 illustrates a plan view of an exemplary nucleic acid purification cartridge having an arrangement of sealing ribs for defining and sealing various fluid channels of the cartridge.

FIG. 21 schematically illustrates a purification cartridge 501 having a series of fluid channels defined by the presence of a plurality of polymeric ribs 522. The ribs 522 function to separate different sections of the cartridge and thereby define the limits of separate fluid channels. As shown, some of the defined fluid channels form relatively narrow fluid paths 504 while other fluid channels form relatively wider and larger fluid reservoirs 506. As used herein, "reservoir" will typically refer to a portion of a cartridge configured to store, mix, filter, separate, and/or react a fluid whereas the narrower paths between these reservoir spaces are primarily configured for transporting fluid from one reservoir to another.

Figure 22:
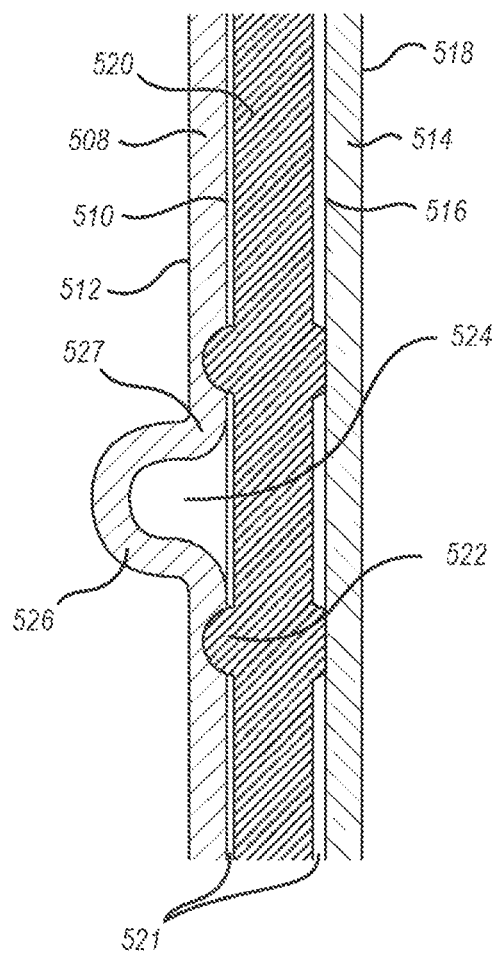
FIG. 22 is a cross-sectional view of a fluid channel of the cartridge, showing an elastomer layer with sealing ribs disposed between two external layers.

FIG. 22 illustrates a cross-sectional view of a section of the cartridge 501 to illustrate the multiple layers that may be included to form the cartridge and define the various fluid channels. The view of FIG. 22 shows a fluid channel 524 in cross-section. The cartridge section is shown here as being vertically oriented, which is the orientation the cartridge will take in preferred embodiments. However, it will be understood that the features described herein do not necessitate a vertical orientation, and other orientations may also be utilized according to particular application needs and/or preferences.

The illustrated embodiment includes a first external layer 508. The first external layer 508 includes a first side 510 (i.e., an inner side) and a second side 512 (i.e., an outer side). A second external layer 514 is disposed opposite the first side 510 of the first external layer 508. The second external layer 514 likewise includes a first side 516 (i.e., an inner side) and an outer side 518 (i.e., an outer side).

As shown, the first external layer 510 may include an outwardly extending indentation or groove that defines the wall surface 526 of the fluid channel 524. The cross-sectional shape of the fluid channel may be substantially curved such as in the illustrated example, with an inner section that is wider than a more external section (i.e., the bottom or "nadir" of the fluid channel). In the illustrated embodiment, the wall surface 526 rises and moves out from the nadir to inflection points 527 disposed on either side of the nadir. Alternative embodiments may include fluid channels with different cross-sectional shapes, including polygonal shapes such as rectangular cross-sectional shapes.

Disposed between the first external layer 510 and the second external layer 514 is an elastomer layer 520. The elastomer layer 520 includes an arrangement of sealing ribs 522. As shown, a pair of sealing ribs 522 extends toward the first side 510 of the first external layer 508 and contacts the first side 510 of the first external layer 508 so that a sealing rib 522 is disposed on each side of the fluid channel 524. The sealing ribs 522 thereby define the width of the fluid channel 524 and limit the "upward" and "downward" (from the perspective of FIG. 22) movement of fluid within the channel 524. As shown, the sealing ribs 522 may be oriented such that an apex (i.e., the inward most point) of each rib 522 is aligned at the opposing inflection points 527 or beyond the inflection points 527 relative to the channel nadir.

In the illustrated embodiment, a nominal gap 521 may exist between the elastomer layer 520 and the first external layer 508 and/or second external layer 514. The nominal gap(s) 521 allow space for the elastomer material of the sealing ribs 522 to deflect when compressed. The ribs 522 are also preferably spaced a slight distance away from the fluid channel wall 526 so that when compressed they do not deflect and overly cover the fluid channel.

The elastomer layer 520 may be formed from a variety of suitable elastomer materials, including thermoset elastomers and thermoplastic elastomers. Non-limiting examples of suitable elastomers include natural rubber, isoprene rubber, butadiene rubber, chloroprene rubber, butyl rubber, halogenated butyl rubbers such as chloro-butyl rubber and bromo-butyl rubber, styrene-butadiene rubber, nitrile rubber, ethylene propylene rubber, ethylene propylene diene rubber, epicholorohydrin rubber, polyacrylic rubber, silicone rubber, fluorosilicone, fluoroelastomers, perfluoroelastomers, polyether block amides (PEBA), chlorosulfonated polyethylene, ethylene-vinyl acetate, closed-cell foams, and combinations thereof. As an example, the elastomer layer may have a Young's modulus of about 5 to about 500 MPa, or about 10 to about 100 MPa.

The external layers 508 and 514 may be formed from a variety of suitable materials. The external layers 508 and 514 preferably have greater rigidity (e.g., higher Young's modulus) than the elastomer layer 520. Preferably, the external layers 508 and 514 are formed from a polymer material that is readily manufactured in a thermoforming process. Non-limiting examples include polyethylene, polypropylene, polycarbonate, polyethylene terephthalate, polystyrene, polyvinyl chloride, other polymers, and combinations thereof. As an example, the external layers 508 and 514 may have a Young's modulus of about 500 to about 4,000 MPa.

The embodiment shown in FIG. 22 includes a fluid channel 524 formed in the first external layer 508 and includes sealing ribs 522 that extend toward the first external layer 508. Although not shown here, the cartridge may also include one or more fluid channels formed in the second external layer 514, with associated sealing ribs that extend from the elastomer layer 520 toward the second external layer 514.

Figure 23A:
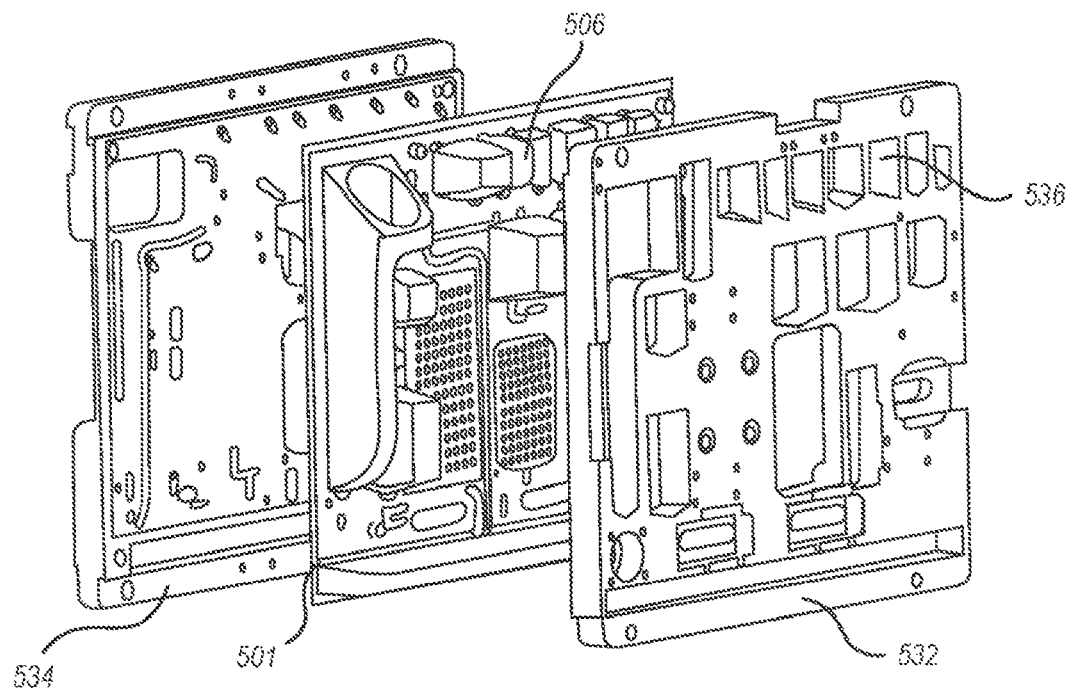
FIGS. 23A and 23B illustrate clamping of the cartridge to compress the sealing rib arrangement and provide sealing sufficient for a purification process.
Figure 23B:
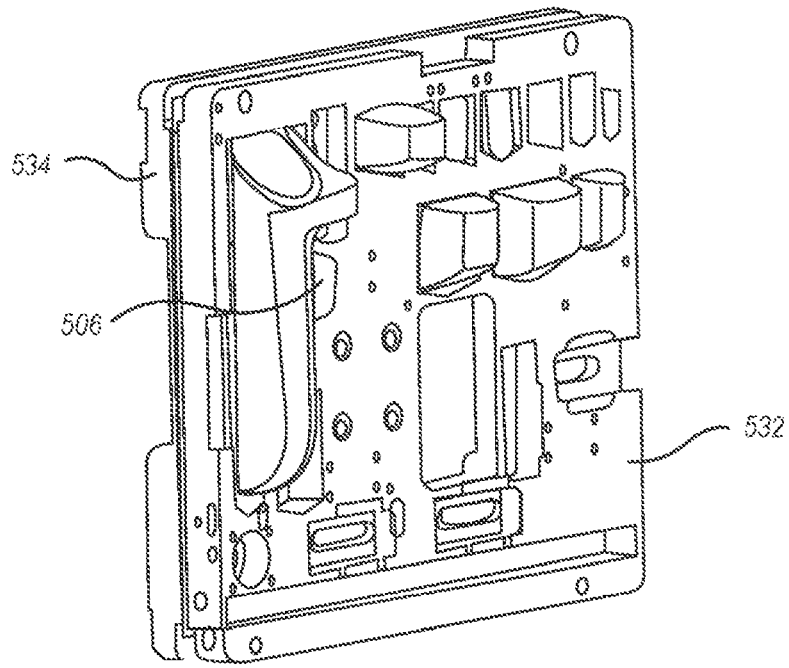

The ribs 522 are configured to seal the fluid channel 524 and thereby fluidically separate it from any other fluid channels when the elastomer layer 520 is compressed between the first and second external layers 508 and 514. FIGS. 23A and 23B illustrate an example of the cartridge 501 undergoing clamping between a first clamping plate 532 and a second clamping plate 534. FIG. 23A shows the clamping plates 532, 534 prior to compression against the cartridge 501 and FIG. 23B shows the cartridge 501 fully compressed between the clamping plates 532, 534.

The clamping plates 532 and 534 are configured in size and shape to be positioned on either side of the cartridge 501 to allow compression of the portions of the cartridge 501 containing sealing ribs while leaving other sections such as the reservoirs 506 uncompressed. For example, the plates 532 and 534 may include apertures 536 that allow the bulk of the reservoirs 506 to avoid compression while the underlying ribs are positioned so as to be subject to compression.

The sealing rib arrangement is configured to withstand at least about 500 lbf, or preferably up to about 15,000 lbf of compression, applied across an entire length of the arrangement of sealing ribs. When compressed under these types of loads, the sealing ribs may deflect by about 20% to about 30% or more. Such compression has been shown to adequately maintain a seal force of about 4.5 lbf per inch, which capable of maintaining the seals at pressures upwards of 50 to 60 psi.

The compression may be provided by a clamping mechanism of a purification instrument such as described elsewhere herein in relation to the purification instrument. However, other embodiments may utilize other clamping mechanisms that need not necessarily operate as a result of actuation by a purification instrument. For example, some embodiments may include a cartridge that has a consumable middle section and two reusable plate sections that can be positioned over the middle section and tightened to compress the middle section prior to use.

Valving

The purification cartridge 501 may include a plurality of valves at different locations that can be selectively opened and closed to direct fluid flow during a purification procedure. For example, one or more valves may be disposed near each reservoir of the cartridge and configured to control fluid movement into and/or out of the reservoir during a purification process.

Figure 24:
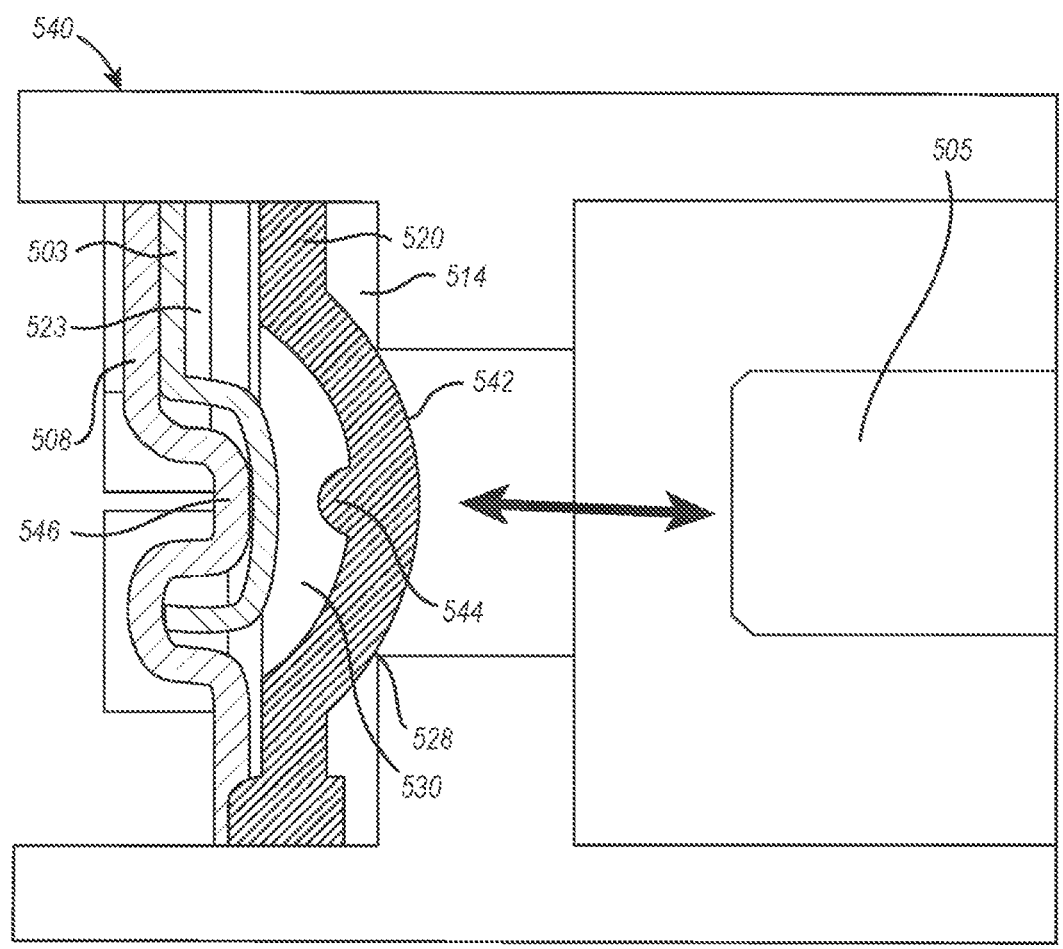
FIG. 24 illustrates a valve mechanism that utilizes the elastomer layer to provide the valving mechanism.

FIG. 24 illustrates, in cross section, an exemplary valve mechanism 540. The valve component of the valve mechanism 540 may be beneficially formed using the same elastomer layer 520 utilized elsewhere in the cartridge 501 to form sealing ribs 522, reducing the number of necessary components and simplifying manufacture of the cartridge.

As shown, the elastomer layer 520 includes a deflectable portion 542 that extends through an aperture 528 formed in the second external layer 514. The deflectable portion 542 is illustrated here as a "dome"-shaped structure. However, other embodiments may provide deflectable portions of other shapes. The deflectable portion 542 is biased outward such that an opening 530 is provided between fluid channel 523 and fluid channel 525 formed in the first external layer 508.

In the open state, fluid 503 is able to freely pass over a berm 546 formed between the fluid channels 523 and 525. The valve may be actuated and moved to a closed state when a plunger 505 or other suitable structure engages against the deflectable portion 542 and deflects it toward the berm 546. The side of the deflectable portion 542 facing the berm 546 may include a sealing rib 544 which can engage with the berm 546 under compression from the plunger 505 to aid in closing the opening 530 and sealing fluid channel 525 from fluid channel 523. When the plunger 505 is retracted, the deflectable portion 542 rebounds to its normal geometry, thereby reopening the valve.

The deflectable portion 542 is preferably able to remain closed under pressures reaching upwards of 30 psi, or even upwards of 50 to 60 psi. This translates to a required force of about 5 lbf against the deflectable portion 542 to hold it in the closed position. The deflectable portion 542 should therefore preferably be configured to withstand a force of about 3 to 7 lbf, and/or a pressure of up to about 50 to 60 psi, without failing or "cracking" to let fluid pass through.

The plunger 505 may be part of a purification instrument in which the cartridge 501 is able to be processed. For example, a plurality of plungers may be mounted to one or both of the clamp plates of the purification instrument described herein.

The cross-sectional shape of the sealing ribs 522 and 544 is illustrated in the foregoing examples as having semicircular geometry (e.g., substantially similar to O-ring geometry). Other embodiments may include other cross-sectional shapes including other curved shapes or polygonal shapes such as triangles.

It should be appreciated that any of the foregoing processing systems, valving, seals, etc. disclosed above with respect to any of the target biomolecule purification systems and cartridges can be utilized and adapted for use with systems and cartridges configured specifically for automated purification of target nucleic acids or target proteins where appropriate.

Abbreviated List of Defined Terms

To assist in understanding the scope and content of this written description and the appended claims, a select few terms are defined directly below. Unless defined otherwise, all technical and scientific terms used herein have the same meaning as commonly understood by one of ordinary skill in the art to which the present disclosure pertains.

The terms "approximately," "about," and "substantially," as used herein, represent an amount or condition close to the specific stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a specifically stated amount or condition.

The term "buffer" refers contextually to any suitable buffer, wash solution, resuspension buffer, lysis buffer, neutralization buffer, RNase (or other enzyme), binding buffer/solution, elution/collection buffer, or precipitation buffer that may be used with or without any additional suitable reagents depending on the protocol being performed. Suitable buffers, as well as their compositions and methods of use are disclosed in the following U.S. patent references: U.S. Pat. No. 6,914,137, U.S. Pat. Pub. Nos. 2006/0154247, 2007/0117972, U.S. Pat. Nos. 6,242,220, 5,990,301, 7,214, 508, 7,109,322, and 6,297,371, all of which are hereby incorporated by reference in their entirety.

Exemplary resuspension buffers in accordance with the presently described systems and methods can include any suitable biologically acceptable buffer such as, for example, Tris, TAPS, Bicine, Tricine, HEPES, TES, MOPS, PIPES, cacodylate, IVIES, acetate, or the like having pH between about 3.5 to about 9, between about 5 to about 8, or between about 6.5 to about 7.5. Additionally, resuspension buffers may include between 1 mM to 100 mM, between 5 mM to 50 mM, or between 10 mM to 20 mM of a chelating agent such as, for example, EDTA, EGTA, ALA, BAPTA, defarasirox, deferiprone, deferoxamine, DTPA, dimercaprol, DMPS, DMSA, or the like. Resuspension buffers may optionally include a ribonuclease, such as an endoribonuclease and/or exoribonuclease selected from any one or more of RNase A, RNase H, RNase I, RNase III, RNase L, RNase P, RNase PhyM, RNase T1, RNase T2, RNase U2, RNase VI, RNase V, PNPase, RNase PEI, RNase II, RNase R, RNase D, RNase T, Exoribonuclease I, Exoribonuiclease II, and the like. In some embodiments, a resuspension buffer may optionally include lysozyme and/or between about 1 mM to about 500 mM, between about 10 mM to about 200 mM, between about 20 mM to about 100 mM, between about 30 mM to about 75 mM of a carbohydrate such as a sugar. Exemplary sugars include glucose, fructose, galactose, mannose, maltose, lactose, and the like.

For example, a resuspension buffer may be an aqueous solution containing 50 mM Tris-HCl (pH 8.0) and 10 mM EDTA. As an additional example, a resuspension buffer may be an aqueous solution containing 50 mM Tris-HCl (pH 8.0), 2.4 mg/ml RNase A, and 10 mM EDTA. As yet another non-limiting example, a resuspension buffer may be an aqueous solution containing 50 mM Tris, (pH 7.4), 100 pg/ml RNase Al, 10 mM EDTA, and 5 mM glucose.

Regarding lysis solutions or buffers, a suitable lysis solutions or buffer may include, in an aqueous carrier medium, one or more denaturants in combination with one or more lipid disruptive agents. The denaturants may be nucleic acid denaturants such, for example, an alkaline salt. Suitable alkaline salts may include sodium hydroxide, potassium hydroxide, calcium hydroxide, and the like. Suitable lipid disruptive agents may include ionic surfactants. Exemplary ionic surfactants include sodium cholate, Sodium dodecylsulfate (SDS), sodium deoxycholate (DOC), N-lauroylsarcosine salts, cetyltrimethylammoniumbromide (CTAB), Bis(2-ethylhexyl)sulfosuccinate salts, and the like.

As a non-limiting example, a lysis buffer used herein may be an aqueous formulation containing 1% (v/v) SDS and 200 mM sodium hydroxide. As another non-limiting example, an exemplary lysis solution may be an aqueous solution containing between about 10 mM to about 500 mM, from about 50 mM to about 250 mM, or from about 100 mM to about 200 mM NaOH in combination with up to about 10% (v/v) SDS, up to about 5% (v/v) SDS or up to about 1% (v/v) SDS. It should be appreciated that additional agents may be present in the lysis buffer, as will be readily apparent to one skilled in the art.

Regarding neutralization solutions, suitable neutralization solutions can include, in an appropriate aqueous carrier medium, one or more agents capable of neutralizing the surfactants/alkaline solution present in the lysis solution. In some embodiments, a neutralization solution may include between about 0.5 M to about 5 M of an appropriate acetate salt, having a pH greater than 4. An exemplary neutralization solution may include an aqueous solution of about 3.1 M potassium acetate with a pH of about 5.5.

In some embodiments, such as for protein purification, non-chaotropic buffers and reagents that do not disrupt protein structure and function can be used.

A suitable wash buffer may include, in an appropriate aqueous carrier medium, between 0.1 mM to about 100 mM salt, between about 0.5 mM to about 500 mM of an appropriate biological buffer such that the pH of the wash buffer is at least about 6.0 or higher, and at least 5% (v/v), at least 10% (v/v) or at least 15% (v/v) of an appropriate alcohol such as ethanol or isopropyl alcohol. In an exemplary embodiment, the wash buffer may be an aqueous solution including 812.5 mM NaCl and 100 mM sodium acetate Trihydrate with a pH of 5.0. As another non-limiting example, the wash buffer may be a formulation including, 1.5 NaCl, 100 mm Sodium Acetate Trihydrate at a pH of 5.0. Optionally, a wash buffer may include between about 0.01% (v/v) to up to about 10% (v/v) of a suitable non-ionic detergent such as, e.g., TRITON® X-100, CHAPS, or NP-40. The addition of such a detergent may, in some embodiments, enhance the removal of unwanted endotoxins from the preparation. Accordingly, an exemplary endotoxin removal/wash buffer may include 10% (v/v) TRITON® X-100, 750 mM NaCl, and 50 mM MOPS (pH 7.0). As another non-limiting example, an endotoxin removal/wash buffer may include 1 M NaCl, 50 mM MOPS, pH>8.0, 15% (v/v) isopropyl alcohol and 0.5% (v/v) TRITON® X-100.

In some embodiments, ultrapure or distilled water can be used to elute the target nucleic acid. Alternatively, TE buffer or an elution buffer can be used. TE buffer can include, for example, an aqueous carrier medium containing 10 mM Tris (pH 8.0) and 0.1 mM EDTA. A suitable elution buffer may include, in an appropriate aqueous carrier medium, salt, up to about 150 mM of an appropriate biological buffer having a pH between 5.0-9.0, and/or up to about 10 mM of an appropriate chelating agent. An exemplary elution buffer can include, for example, 100 mM Tris-HCl (pH 8.5) and 1250 mM NaCl. Another non-limiting example of an elution buffer includes 10 mM Tris-HCl (pH 8.0) in combination with 1 mM EDTA.

In some embodiments, an equilibration buffer may optionally be passed through the membranes or filters used in any of the first or second bioprocessing assemblies prior to the use thereof. In such embodiments, an equilibration buffer may include up to 1 M of a salt, up to 500 mM of an appropriate biological buffer having a pH between 5.0-9.0, up to about 10% (v/v) of an appropriate non-ionic detergent and up to about 20% (v/v) alcohol. An exemplary equilibration buffer may include, for example, 750 mM NaCl, 50 mM MOPS (pH 7), 15% (v/v) isopropyl alcohol, and about 0.15% (v/v) TRITON® X-100.

In some embodiments, a precipitation buffer may optionally be passed through the precipitation filter prior to the use thereof. A precipitation buffer may include, for example, up to 5 M potassium acetate, up to 500 mM of an appropriate biological buffer having a pH between about 5.0-9.0. An exemplary precipitation buffer may include, for example, 3.1 M Potassium Acetate with a pH of 5.5.

As used herein, the term "large volume," includes any volume greater than about 5 mL, preferably any volume greater than about 10 mL or any value or range of values between 10 mL and 5 L. It should be appreciated that the term "large volume," as used herein, is generally made with reference to the biological sample and can include volumes up to 250 mL, between 10-250 mL, between 50-200 mL, between 100-150 mL, between 100 mL-2 L, or any range or value therebetween. For example, plasmid DNA can be purified from a large volume of bacterial culture using the disclosed systems, methods, and devices where the large volume is 150 mL. As an additional, non-limiting example, the large volume can include up to 1 L of urine. It should be appreciated that the systems, methods, and devices disclosed herein can be adjusted, as appropriate, to process different volumes of biological sample, including smaller volumes than those described above.

The term "target biomolecule," as used herein, is intended to be understood as a nucleic acid or protein—as those terms are defined herein—derived from a biological or environmental source.

The term "target nucleic acid," as used herein, is intended to be understood as a nucleic acid sequence derived from a biological or environmental source and can be one or more of a gene, a regulatory sequence, genomic DNA, plasmid DNA, cDNA, or RNA. As is outlined herein, the target nucleic acid may take any of the foregoing forms and may be any length, although in a preferred embodiment, the target nucleic acid constitutes a plasmid obtained from bacterial culture.

The term "target protein," as used herein, is intended to be understood as a protein sequence derived from a biological or environmental source and can be a polypeptide, an oligopeptide, a glycoprotein, a lipoprotein, a phosphoprotein, a membrane protein or any protein. As is outlined herein, the target protein may take any of the foregoing forms and may be any length, although in a preferred embodiment, the target protein is in its biologically active state and conformation, which can include native posttranslational modifications and can be without contamination or chemical modification.

Various aspects of the present disclosure, including devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used in the specification, a word appearing in the singular encompasses its plural counterpart, and a word appearing in the plural encompasses its singular counterpart, unless implicitly or explicitly understood or stated otherwise. Thus, it will be noted that, as used in this specification and the appended claims, the singular forms "a," "an" and "the" include plural referents unless the context clearly dictates otherwise. For example, reference to a singular referent (e.g., "a widget") includes one, two, or more referents unless implicitly or explicitly understood or stated otherwise. Similarly, reference to a plurality of referents should be interpreted as comprising a single referent and/or a plurality of referents unless the content and/or context clearly dictate otherwise. For example, reference to referents in the plural form (e.g., "widgets") does not necessarily require a plurality of such referents. Instead, it will be appreciated that independent of the inferred number of referents, one or more referents are contemplated herein unless stated otherwise.

As used herein, directional terms, such as "top," "bottom," "left," "right," "up," "down," "upper," "lower," "proximal," "distal" and the like are used herein solely to indicate relative directions and are not otherwise intended to limit the scope of the disclosure and/or claimed invention.

Conclusion

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed in part by preferred embodiments, exemplary embodiments, and optional features, modification and variation of the concepts herein disclosed may be resorted to by those skilled in the art, and such modifications and variations are considered to be within the scope of this invention as defined by the appended claims. The specific embodiments provided herein are examples of useful embodiments of the present invention and various alterations and/or modifications of the inventive features illustrated herein, and additional applications of the principles illustrated herein that would occur to one skilled in the relevant art and having possession of this disclosure, can be made to the illustrated embodiments without departing from the spirit and scope of the invention as defined by the claims and are to be considered within the scope of this disclosure.

It will also be appreciated that systems, devices, products, kits, methods, and/or processes, according to certain embodiments of the present disclosure may include, incorporate, or otherwise comprise properties or features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

All references cited in this application are hereby incorporated in their entireties by reference to the extent that they are not inconsistent with the disclosure in this application. It will be apparent to one of ordinary skill in the art that methods, devices, device elements, materials, procedures, and techniques other than those specifically described herein can be applied to the practice of the invention as broadly disclosed herein without resort to undue experimentation. All art-known functional equivalents of methods, devices, device elements, materials, procedures, and techniques specifically described herein are intended to be encompassed by this invention.

When a group of materials, compositions, components, or compounds is disclosed herein, it is understood that all individual members of those groups and all subgroups thereof are disclosed separately. When a Markush group or other grouping is used herein, all individual members of the group and all combinations and sub-combinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All changes which come within the meaning and range of equivalency of the claims are to be embraced within their scope.

EXAMPLES

The following examples are provided to illustrate implementations of various embodiments disclosed herein and are intended to be exemplary in nature and not unnecessarily limiting of the scope and/or content of the disclosure provided herewith.

Example 1

An instrument and accompanying single use cartridge as disclosed herein were utilized for a fully automated plasmid DNA purification protocol directly from bacterial culture.

To grow bacterial culture with the target nucleic acid (e.g., plasmid DNA), a single colony of bacteria containing the plasmid of interest was picked from a freshly streaked selective plate and a 1 mL starter culture of LB medium (containing the appropriate selective antibiotic, in this case ampicillin) was inoculated. The culture was incubated at 37° C. for 8 hours with vigorous shaking (300 rpm). Next, the starter culture was diluted 1:1000 in LB medium containing the appropriate selective antibiotic, in a 5 L flask. The 1 L culture was incubated at 37° C. for about 14 hours with vigorous shaking (300 rpm) to promote growth and amplification of bacteria. The bacterial culture was then checked to ensure it had reached a cell density of approximately $2-6\times10^9$ cells/mL or an absorbance of 2.0-6.0 at 600 nm ($A_{600}$) followed by processing towards plasmid DNA purification.

Bacterial cells used in this particular example were Top 10 and DH5α *Escherichia coli*, but other *E. coli* strains were utilized as well in additional studies yielding similar results. Plasmid utilized in this particular example was a high copy pGL 4.50, but other plasmids with various backbones, and inserts of various sizes, high and low copy, were utilized as well in the similar experiments with similar results.

The instrument prototype and accompanying single use cartridge prototype (e.g., the cartridge 160b of FIG. 7b) were utilized for a fully automated plasmid DNA purification from 150 ml of bacterial culture (maxi scale). PureLink™ Expi Endotoxin-Free Maxi Plasmid Purification Kit was utilized side by side, strictly following the manufacturers protocol as a control.

Figure 25:
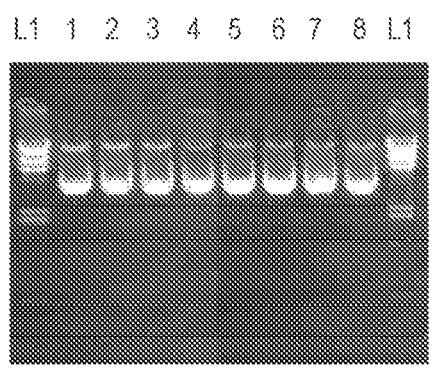
FIG. 25 illustrates an agarose gel analysis of plasmid product isolated using an exemplary system and nucleic acid purification cartridge disclosed herein.

FIG. 1 shows results for three instrument runs and one manual preparation with PureLink kit for pGL4.50 plasmid/Top 10 cells, culture $OD_{600}$=3.0, and three instrument runs and one manual preparation with PureLink kit for pGL4.50 plasmid/DH5a cells, culture $OD_{600}$=4.5. Table 1 below captures plasmid DNA yield (micrograms), plasmid concentration in the output tube with about 1 ml elution volume, and plasmid purity as measured by Nanodrop (A260/280, A260/230). Agarose gel analysis of the plasmid product is shown in FIG. 25.

TABLE 1

| Well ID | Run/Sample ID | Sample Description | Culture Input (mL) | pDNA (ng/µg) | pDNA (µg) | A260/A280 | A260/A230 |
|---|---|---|---|---|---|---|---|
| 1 | NE 144 | TOP10/pGL4.50, | 150 | 708.8 | 755 | 1.9 | 2.28 |
| 2 | NE 145 | OD 3.0 | | 710.9 | 803 | 1.91 | 2.3 |
| 3 | NE 146 | | | 629.6 | 756 | 1.94 | 2.37 |
| 4 | MP 100719 | PureLink manual prep* | 100 | 681.6 | 682 | 1.91 | 2.23 |
| 5 | NE 147 | DH5a/pGL4.50, | 150 | 824.9 | 982 | 1.92 | 2.3 |
| 6 | NE 148 | OD 4.53 | | 852.2 | 906 | 1.93 | 2.3 |
| 7 | NE 149 | | | 782.6 | 881 | 1.92 | 2.29 |
| 8 | MP 100819 | PureLink manual prep* | 100 | 1079.3 | 1079 | 1.9 | 2.26 |
| L1 | | Lambda Hind III DNA Markers (125 bp-23.1 Kb) | | | | | |

For pGL4.50 plasmid/Top 10 cells, plasmid yield for the automated purification was 755-803 micrograms, and pGL4.50 plasmid/DH5a cells—881-982 micrograms, very similar to the manual prep with PureLink anion exchange column-based kit. A260/280 purity for all samples was high (e.g., greater than 1.9). A260/230 purity for all samples was high (e.g., greater than 2.2). Agarose gel analysis demonstrated high purity and integrity of the purified plasmid product.

Table 2 below shows results for a total of 25 plasmid purification runs on two instrument prototypes. Average yield for a high copy plasmid, obtained from 150 ml of input bacterial culture, was 796 micrograms, which is commensurate with a manual maxi-prep. Plasmid purity was as described above for FIG. 25 and met the requirements. The instrument prototype total run time was about 50 minutes, which was significantly faster than the manual preparation, which takes at least 1.5 hours or longer for the typical anion exchange membrane-based columns.

As shown, instrument prototypes and accompanying cartridge prototypes enable fully automated plasmid DNA purification, straight from bacterial culture (without centrifugation), and deliver high yield of clean plasmid DNA, significantly faster than the "classic" manual purification kits.

Additional Embodiment Descriptions

The following are exemplary, non-limiting embodiments incorporating one or more of the features described by the foregoing.

Embodiment 1. An apparatus for automated purification of a biomolecule, such as a target nucleic acid or a target protein, from a biological sample comprises: an input reservoir for receiving the biological sample; a first bioprocessing assembly in fluid communication with the input reservoir and a lysis buffer reservoir, the first bioprocessing assembly configured to generate a lysate comprising a target biomolecule, such as a target nucleic acid or a target protein; a second bioprocessing assembly in fluid communication with the first bioprocessing assembly and a first elution buffer reservoir, the second bioprocessing assembly including a target-biomolecule-binding filter, such as a target-nucleic-acid-binding filter or a target-protein-binding filter, configured to retain the target biomolecule; and a receptacle in fluid communication with the second bioprocessing assembly, the receptacle configured to receive an output container for receiving the target biomolecule, such as the target nucleic acid or the target protein, from the second bioprocessing assembly.

Embodiment 2. The apparatus of Embodiment 1, wherein the apparatus comprises a consumable cartridge.

Embodiment 3. The apparatus of any one of Embodiments 1-2, wherein the input reservoir is configured to receive a large volume clinical sample, a large volume environmental sample, a food sample, or a beverage sample.

TABLE 2

Summary for a total of 25 plasmid purification runs on cartridges #1 and #2 (each cartridge having a design as shown in FIG. 7B; results based on 150 ml of bacterial culture input).

| | Plasmid Conc. (ng/µL) | Eluate Volume (µL) | Plasmid Yield (µg) | #1 Total Yield (µg) | #2 Total Yield (µg) | A260/A280 | A260/A230 | Total Run Time (min) |
|---|---|---|---|---|---|---|---|---|
| Avg | 761 | 1091 | 796 | 802 | 789 | ✓ | ✓ | 50.7 |
| SD | 86 | 66 | 84 | 102 | 56 | N/A | N/A | 9.4 |
| CV (%) | 11 | N/A | 11 | 13 | 7 | N/A | N/A | N/A |
| N | 25 | 25 | 25 | 14 | 11 | 24 | 24 | 16 |

Embodiment 4. The apparatus of any one of Embodiments 1-3, further comprising an optical density detector window disposed between the input reservoir and the first bioprocessing assembly, the optical density detector window being configured to allow detection of an optical density of the biological sample.

Embodiment 5. The apparatus of any one of Embodiments 1-4, wherein the first bioprocessing assembly comprises a clarification filter.

Embodiment 6. The apparatus of Embodiment 5, wherein the clarification filter is in fluid communication with the input reservoir and the lysis buffer reservoir, the clarification filter being configured to separate a target-nucleic-acid-containing portion of the biological sample from a first waste portion of the biological sample.

Embodiment 7. The apparatus of Embodiments 5 or 6, wherein the first bioprocessing assembly comprises a cell capture filter, wherein the cell capture filter is disposed upstream of the clarification filter.

Embodiment 8. The apparatus of Embodiment 7, wherein the cell capture or concentration filter is in fluid communication with the input reservoir and the lysis buffer reservoir, the cell capture or concentration filter being configured to separate a target-nucleic-acid-containing portion of the biological sample from a first waste portion of the biological sample.

Embodiment 9. The apparatus of Embodiment 7 or 8, wherein the lysis buffer reservoir is fluidically coupled to the cell capture filter to enable backwashing of the cell capture filter and passage of backwash to the clarification filter.

Embodiment 10. The apparatus of Embodiment 9, further comprising a first mixing chamber disposed between the clarification filter and the cell capture filter, the first mixing chamber configured to receive the backwash.

Embodiment 11. The apparatus of Embodiment 10, further comprising a neutralization buffer reservoir in fluid communication with the first mixing chamber, the first mixing chamber being configured to receive the backwash and a neutralization buffer and to provide mixing of the backwash and the neutralization buffer to form a neutralized lysate.

Embodiment 12. The apparatus of Embodiment 11, wherein the clarification filter is in fluid communication with the first mixing chamber, the clarification filter being configured to separate a second waste portion from the target-nucleic-acid-containing portion of the biological sample.

Embodiment 13. The apparatus of any one of Embodiments 9-12, wherein the clarification filter comprises the cell capture filter, the cell capture filter being configured to concentrate a cellular component of the biological sample at a first purification step and to clarify the neutralized lysate at a second, later purification step.

Embodiment 14. The apparatus of any one of Embodiments 1-13, wherein the target-biomolecule-binding filter of the second bioprocessing assembly comprises a silica-based filter or a column of beads having affinity for the target nucleic acid.

Embodiment 15. The apparatus of Embodiment 14, wherein the second bioprocessing assembly further comprises a purification reagent reservoir in fluid communication with the target-biomolecule-binding filter, such as the nucleic-acid-binding filter.

Embodiment 16. The apparatus of Embodiment 14 or 15, wherein the target-biomolecule-binding filter, such as the nucleic-acid-binding filter, is in fluid communication with the elution buffer reservoir and the output container.

Embodiment 17. The apparatus of any one of Embodiments 1-16, wherein the second bioprocessing assembly comprises a second mixing chamber disposed between the first bioprocessing assembly and the target-biomolecule-binding filter.

Embodiment 18. The apparatus of Embodiment 17, wherein the second mixing chamber is in fluid communication with an endotoxin removal buffer reservoir.

Embodiment 19. The apparatus of any one of Embodiments 1-18, wherein the target-biomolecule-binding filter is the nucleic-acid binding filter comprising an anion exchange membrane.

Embodiment 20. The apparatus of Embodiment 19, wherein the second bioprocessing assembly comprises a precipitator membrane disposed downstream of the anion exchange membrane.

Embodiment 21. The apparatus of Embodiment 20, wherein the anion exchange membrane is configured to separate a third waste portion from the target-nucleic-acid-containing portion of the biological sample.

Embodiment 22. The apparatus of Embodiment 20 or 21, further comprising a second elution buffer reservoir, the first elution buffer reservoir being fluidically coupled to the anion exchange membrane to enable elution of the target nucleic acid from the anion exchange membrane, and the second elution buffer reservoir being fluidically coupled to the precipitator membrane to enable elution of the target nucleic acid from the precipitator membrane.

Embodiment 23. The apparatus of any one of Embodiments 20-22, wherein the precipitator membrane is configured to separate a fourth waste portion from the target-nucleic-acid-containing portion of the biological sample.

Embodiment 24. The apparatus of any one of Embodiments 20-23, wherein the precipitator membrane is in fluid communication with a precipitation reagent reservoir, the precipitation reagent reservoir optionally comprising isopropanol.

Embodiment 25. The apparatus of any one of Embodiments 20-24, wherein the precipitator membrane is in fluid communication with a wash/desalting solution reservoir, the wash/desalting solution reservoir optionally comprising about 70% ethanol.

Embodiment 26. The apparatus of any one of Embodiments 20-25, wherein the second bioprocessing assembly comprises a third mixing chamber disposed between and in fluid communication with the anion exchange membrane and the precipitator membrane, wherein the third mixing chamber is fluidically coupled to the precipitation reagent reservoir and/or the desalting solution reservoir and is disposed between the precipitator membrane and the precipitation reagent reservoir and/or the desalting solution reservoir.

Embodiment 27. The apparatus of any one of Embodiments 1-26, wherein the output container is selectively detachable from the apparatus.

Embodiment 28. The apparatus of any one of Embodiments 1-27, wherein the input reservoir is sized and shaped to receive at least 5 mL, preferably at least 100 ml, or up to 2 L of biological sample.

Embodiment 29. An embodiment of an apparatus for automated purification of a target nucleic acid from a biological sample, comprises: an input reservoir for receiving the biological sample; a first bioprocessing assembly in fluid communication with the input reservoir and a lysis buffer reservoir, the first bioprocessing assembly configured to generate a lysate comprising a target nucleic acid; a second bioprocessing assembly in fluid communication with the first bioprocessing assembly and a first elution buffer reservoir, the second bioprocessing assembly including a nucleic-acid-binding filter configured to retain the target nucleic acid; and a receptacle in fluid communication with the second bioprocessing assembly, the receptacle configured to receive an output container for receiving the target nucleic acid in purified form. Another embodiment of an apparatus for automated purification of a target nucleic acid from a biological sample comprises: a first bioprocessing assembly configured to receive the biological sample, the first bioprocessing assembly comprising a waste separation filter and a plurality of reservoirs fluidically coupled to the waste-separation filter; a second bioprocessing assembly comprising an anion exchange membrane, a washing solution reservoir fluidically coupled to the anion exchange membrane and a first elution buffer reservoir fluidically coupled to the anion exchange membrane; and a third bioprocessing assembly comprising a precipitation filter and a second elution buffer reservoir fluidically coupled to the precipitation filter.

Embodiment 30. The apparatuses of Embodiment 29, wherein the first bioprocessing assembly additionally comprises a cell capture filter, and wherein a first reservoir of the plurality of reservoirs comprises a resuspension buffer reservoir.

Embodiment 31. The apparatus of Embodiment 30, wherein an input reservoir is fluidically coupled to a first side of the cell capture filter and the resuspension buffer reservoir is fluidically coupled to a second side of the cell capture filter.

Embodiment 32. The apparatus of any one of Embodiments 1-31, wherein the apparatus is a consumable cartridge for use in an automated nucleic acid purification system, the consumable cartridge being configured to associate with an automated nucleic acid purification system to enable automatic purification of the target nucleic acid without human interaction.

Embodiment 33. A method for automated purification of target nucleic acid from a biological sample, comprising: receiving the biological sample at an input reservoir; and without further human interaction, generating a lysate from the biological sample at a first bioprocessing assembly, the lysate comprising the target nucleic acid; receiving a target-nucleic-acid-containing portion of the lysate at a second bioprocessing assembly; retaining the target nucleic acid on a nucleic-acid binding filter at the second bioprocessing assembly; and eluting a purified form of the target nucleic acid from the nucleic-acid binding filter into an output container.

Embodiment 34. The method of Embodiment 33, further comprising capturing a cellular content of the biological sample at a first membrane of the first bioprocessing assembly.

Embodiment 35. The method of Embodiment 33 or 34, further comprising measuring an optical density of the biological sample before generating the lysate, optionally wherein the optical density is measured before capturing the cellular content at the first membrane.

Embodiment 36. The method of Embodiment 35, wherein the biological sample comprises a bacterial culture and measuring the optical density of the biological sample comprises automatedly measuring the absorbance of the bacterial culture at about 600 nm.

Embodiment 37. The method of any one of Embodiments 33-36, further comprising resuspending at least a portion of the cellular content in one or more of a resuspension buffer, an RNAse solution, or a lysis buffer, optionally wherein resuspending the at least a portion of the cellular content comprises backwashing the first membrane.

Embodiment 38. The method of Embodiment 37, wherein backwashing the first membrane comprises transferring a resuspension solution comprising one or more of a resuspension buffer, an RNAse solution, or a lysis buffer from a fluidic channel disposed on a second side of the first membrane and through the first membrane.

Embodiment 39. The method of any one of Embodiments 33-38, further comprising mixing the lysate with a neutralization buffer to form a neutralized lysate and separating the target-nucleic-acid-containing portion from a waste portion of the neutralized lysate.

Embodiment 40. The method of any one of Embodiments 33-39, further comprising mixing an endotoxin removal buffer with the target-nucleic-acid containing portion of the lysate.

Embodiment 41. The method of any one of Embodiments 33-40, wherein retaining the target nucleic acid on the nucleic-acid binding filter at the second bioprocessing assembly comprises passing the target-nucleic-acid containing portion of the lysate through an anion exchange membrane.

Embodiment 42. The method Embodiments 41, further comprising removing the target-nucleic-acid containing portion of the lysate from the anion exchange membrane and precipitating the target nucleic acid to desalt and/or concentrate the target nucleic acid, and optionally capturing the precipitated target nucleic acid at a precipitator membrane.

Embodiment 43. The method of any one of Embodiments 33-42, wherein retaining the target nucleic acid on the nucleic-acid binding filter at the second bioprocessing assembly comprises passing the target-nucleic-acid containing portion of the lysate through a precipitator membrane to capture the target nucleic acid at the precipitator membrane.

Embodiment 44. The method of any one of Embodiments 33-43, wherein retaining the target nucleic acid on the nucleic-acid binding filter at the second bioprocessing assembly comprises passing the target-nucleic-acid containing portion of the lysate through a silica-based filter, and mixing the target-nucleic-acid containing portion of the lysate with a chaotropic salt buffer prior to passing the target-nucleic-acid containing portion of the lysate through the silica-based filter, and optionally washing the silica-based filter with alcohol-based wash solutions.

Embodiment 45. The method of Embodiments 44, wherein eluting the purified form of the target nucleic acid from the nucleic-acid binding filter comprises eluting under low-salt conditions using water or TE buffer.

Embodiment 46. The method of any one of Embodiments 33-45, carried out using the apparatus as in any one of Embodiments 1-32.

Embodiment 47. An apparatus for automated purification of a target nucleic acid or target protein from a biological sample comprises: a casing having an internal compartment configured in size and shape for receiving a purification cartridge; optionally, a selectively closable access door providing access to the internal compartment; and a pump assembly disposed within the interior chamber and configured to provide pumping action through peristaltic motion.

Embodiment 48. The apparatus of Embodiment 47, further comprising a clamp mechanism disposed within the internal compartment and configured to move between an open position in which the internal compartment is accessible and a closed position in which the clamp mechanism is clamped against an inserted purification cartridge to enable processing of the biological sample, optionally wherein when in the closed position, the clamp mechanism operates to fluidically seal the biological sample cartridge.

Embodiment 49. The apparatus of Embodiment 48, further comprising a controller, wherein the controller routes power to the clamping mechanism only upon determining that the access door is closed.

Embodiment 50. The apparatus of Embodiment 48 or 49, further comprising a locking mechanism configured to lock the access door in a closed position when the clamp mechanism is moved to the closed position.

Embodiment 51. The apparatus of any one of Embodiments 48-50, wherein the clamp mechanism is powered by a motor, optionally wherein the motor is operatively coupled to a worm gear or drive screw which is rotatable to cause movement of the clamping mechanism.

Embodiment 52. The apparatus of Embodiment 51, further comprising a manual release mechanism operatively coupled to the clamp mechanism to enable manual release of the clamp mechanism independent of the motor.

Embodiment 53. The apparatus of any one of Embodiments 48-52, wherein the casing comprises an open end to which the access door is attached, and a closed end opposite the open end, the open end and closed ends defining a longitudinal direction, wherein the clamp mechanism is configured to move in a direction transverse to the longitudinal direction.

Embodiment 54. The apparatus of any one of Embodiments 47-53, further comprising: an optical density sensor for measuring optical density of a biological sample received within the biological sample cartridge, an optical density sensor for measuring target biomolecule concentration, such as target nucleic acid concentration or target protein concentration, of a purified product, or both.

Embodiment 55. The apparatus of any one of Embodiments 47-54, further comprising a user interface for displaying instrument information and for receiving user input, the user interface configured to receive user input related to one or more of a volume of biological sample, a selected purification protocol, operating instructions for the selectively closable door, a desired concentration of target biomolecule, such as target nucleic acid or target protein, or a final volume of eluent comprising the target biomolecule.

Embodiment 56. The apparatus of any one of Embodiments 47-55, wherein the interior compartment comprises a position sensor for determining that a purification cartridge has been fully inserted within the interior compartment, the limit switch being positioned such that it is actuated upon contact with a leading edge of a purification cartridge when the purification cartridge is fully inserted within the interior compartment.

Embodiment 57. The apparatus of any one of Embodiments 47-56, further comprising one or more access door sensors configured to determine whether the access door is in an open or closed position, wherein the one or more access door sensors optionally comprise one or more Hall effect sensors and one or more corresponding magnets.

Embodiment 58. The apparatus of any one of Embodiments 47-57, further comprising an output container sensor configured to detect a presence of an output container at an inserted purification cartridge.

Embodiment 59. The apparatus of any one of Embodiments 47-58, further comprising one or more rotatable magnets disposed so as to direct an electromagnetic field inward to the interior compartment.

Embodiment 60. The apparatus of any one of Embodiments 47-59, wherein the pump assembly comprises a camshaft coupled to a motor via a power transmission assembly, a plurality of cam elements being attached to the camshaft and extending transversely therefrom toward the purification cartridge when inserted, the cam elements optionally including beveled tips for engaging the purification cartridge when inserted.

Embodiment 61. The apparatus of Embodiment 60, wherein the cam elements are arranged such that rotation of the camshaft causes linear peristaltic motion of cam element tips.

Embodiment 62. A system comprising the apparatus of any one of Embodiments 47-62 and the purification cartridge, wherein the purification cartridge is the apparatus according to any one of Embodiments 1-32.

Embodiment 63. A method for automated purification of a target nucleic acid from a biological sample, comprising: providing an apparatus (or system) as in any one of Embodiments 47-62; loading a purification cartridge through the access door and into the interior compartment of the apparatus; and initiating a purification procedure at the apparatus, wherein initiation of the purification procedure causes the apparatus to automatedly purify the target nucleic acid without further human interaction.

Embodiment 64. The method of Embodiment 63, further comprising closing the access door of the apparatus and moving the clamp mechanism to the closed position to clamp and fluidically seal the loaded purification cartridge.

Embodiment 65. The method of Embodiment 64, further comprising determining that the purification cartridge is fully loaded and/or determining that the access door is fully closed prior to initiating the purification procedure.

Embodiment 66. The method of any one of Embodiments 63-65, further comprising determining that an output container is properly positioned and providing a warning upon determining that an output container is absent.

Embodiment 67. The method of any one of Embodiments 63-66, further comprising determining an optical density of a biological sample within the purification cartridge, optionally wherein the determined optical density of the input sample is utilized to adjust one or more parameters of the purification procedure, the one or more parameters comprising a volume of one or more reagents used in the purification procedure, duration of pumping via the pump assembly, or speed of pumping via the pump assembly.

Embodiment 68. The method of Embodiment 67, wherein a higher optical density reading causes, relative to a lower optical density reading, one or more of: a higher volume of the one or more reagents to be used, a longer pumping time of one or more fluid movement steps, and higher fluid flow rate during one or more fluid movement steps.

Embodiment 69. The method of any one of Embodiments 63-68, wherein an initial optical density reading is taken prior to initiating the purification procedure to determine whether the purification cartridge has been previously used, wherein an optical density reading substantially equal to an air blank reading indicates that a culture input reservoir of the biological sample cartridge remains unbroken.

Embodiment 70. The method of any one of Embodiments 63-69, further comprising loading the purification cartridge with a large volume biological sample having a volume of about 5 ml to 5 L, or 10 ml to 500 ml, or about 15 ml to 250 ml.

Embodiment 71. A control system for controlling an automated purification apparatus (or system) as in any one of Embodiments 47-62, comprising: one or more processors; and one or more hardware storage devices having stored thereon computer-executable instructions which are executable by the one or more processors to cause the control system to at least: receive sensor data from one or more sensors to determine one or more process states of the automated purification apparatus; compare the determined process states to a set of different protocols stored within a protocol library; select a purification protocol from the protocol library based on the determined process states; and carry out the selected purification protocol by causing one or more instrument actuators of the automated purification apparatus to operate according to the selected purification protocol.

Embodiment 72. The control system of Embodiment 71, wherein the one or more sensors include an optical density sensor, an access door sensor, a cartridge proximity or contact sensor, an output container proximity or contact sensor, a cartridge scanner, a timer, a temperature sensor, a weight sensor, a volumetric sensor, or combinations thereof.

Embodiment 73. The control system of Embodiment 71 or 72, wherein the determined process states includes at least a determined optical density of an initial input sample, and optionally wherein the selected purification protocol provides a cell capture duration that is based on the determined optical density of the initial input sample.

Embodiment 74. The control system of any one of Embodiments 71-73, wherein the selected purification protocol defines: whether cell capture and/or cell lysis is utilized, the duration of cell capture and/or cell lysis, which reagents to utilize, volumes of reagents to utilize, whether and/or when to perform mixing at one or more purification steps, duration and/or speed of one or more mixing steps, duration and/or speed of pumping between one or more purification steps, whether and/or when to open and close one or more valves within the cartridge, whether and/or when to puncture one or more seals within the cartridge to allow corresponding release of fluid or venting of gas, a type of target biomolecule capture involved, a duration of the target biomolecule capture, or a combination thereof.

Embodiment 75. A fluid release system for holding and selectively releasing a fluid, comprising: a flexible gasket; a reservoir disposed on a first side of the flexible gasket, the reservoir being configured to hold the fluid; a frangible seal disposed between the flexible gasket and the fluid reservoir; and an actuator disposed on a second side of the flexible gasket, wherein the actuator is operable to deflect the flexible gasket to cause the frangible seal to breach and selectively release the fluid from the reservoir.

Embodiment 76. The system as in Embodiment 75, wherein the flexible gasket is an elastomer.

Embodiment 77. The system as in Embodiment 75 or 76, wherein the flexible gasket is part of an intermediate layer disposed between two external layers, the reservoir optionally being at least partially defined by the flexible gasket and one of the two external layers.

Embodiment 78. The system as in any one of Embodiments 75-77, wherein the frangible seal comprises a chemically inert material, the frangible seal also optionally comprising a reinforcing layer, wherein the chemically inert material is associated with or fused to a face of the reinforcing layer such that the chemically inert material is disposed towards and/or forms a sidewall defining the reservoir.

Embodiment 79. The system as in any one of Embodiments 75-78, wherein the frangible seal comprises a pierceable material configured to catastrophically fail in response to application of a mechanical force exerted by the actuator.

Embodiment 80. The system as in any one of Embodiments 75-79, wherein the fluid comprises a nucleic acid purification reagent, protein purification reagent, input sample, resuspension buffer, RNase A, DNase, proteinase K, lysis buffer, neutralization buffer, chaotropic salt buffer, non-chaotropic salt buffers, binding buffer, endotoxin removal buffer, wash buffer, elution buffer, isopropanol, ethanol, water, or TE buffer.

Embodiment 81. The system as in any one of Embodiments 75-80, further comprising a fluid channel in fluid communication with the reservoir, the fluid channel being configured to receive the fluid upon release of the fluid from the reservoir.

Embodiment 82. The system as in any one of Embodiments 75-81, further comprising a flexible air vent, a frangible air seal disposed on a first side of the flexible air vent, and a venting actuator disposed on a second side of the flexible air vent, optionally wherein the venting actuator is operable to selectively deflect the flexible air vent toward the frangible air seal and thereby breach the frangible air seal to vent air into the reservoir.

Embodiment 83. An automated system for selectively releasing a fluid comprises: the fluid release system as in any one of Embodiments 75-82; and a biological sample cartridge for use with the automated target biomolecule purification system, the biological sample cartridge comprising the apparatus as in any one of Embodiments 1-32, the automated system also optionally comprising the control system of any one of Embodiments 71-74 and optionally comprising the automated purification apparatus or system as in any one of Embodiments 47-62.

Embodiment 84. A method for selectively releasing a fluid from a reservoir in an automated process comprises: contacting a flexible gasket with an actuator; moving the actuator to deflect the flexible gasket toward a frangible seal associated with the reservoir; and causing the flexible gasket to breach the frangible seal, thereby releasing the fluid from the reservoir.

Embodiment 85. The method of Embodiment 84, wherein the fluid is released from the reservoir without the actuator making direct contact with the fluid.

Embodiment 86. The method of Embodiment 84 or 85, further comprising retracting the actuator away from the breached frangible seal and the flexible gasket moving away from the breached frangible seal in response to the actuator retracting away.

Embodiment 87. The method of any one of Embodiments 84-86, further comprising: contacting a flexible air vent with a venting actuator; moving the venting actuator to deflect the flexible air vent toward a frangible air seal; and causing the flexible air vent to breach the frangible air seal, wherein breaching the frangible air seal causes air to vent into the reservoir.

Embodiment 88. The method of any one of Embodiments 84-87, performed using the system of any one of Embodiments 75-83.

Embodiment 89. An apparatus for controlled movement of fluids comprises: a first external layer comprising a first side and a second side, the first side comprising a series of channels; a second external layer disposed opposite the first side of the first external layer; and an elastomer layer disposed between the first and second external layers, the elastomer layer comprising an arrangement of sealing ribs that corresponds to the series of channels and is configured to fluidically separate the channels when the elastomer layer is compressed between the first and second external layers.

Embodiment 90. The apparatus of Embodiment 89, wherein a first channel of the series of channels comprises a reservoir, and optionally wherein one or more of the first external layer or the second external layer is a thermoform polymer.

Embodiment 91. The apparatus of Embodiment 89 or 90, further comprising a nominal gap between the elastomer layer and one or both of the first external layer or the second external layer such that when the elastomer layer is compressed between the first and second external layers, a compressed portion of the sealing ribs is displaced within the nominal gap.

Embodiment 92. The apparatus of any one of Embodiments 89-91, further comprising a valve associated with the series of channels, the valve being selectively moveable between a closed position and an open position to respectively restrict or allow fluid flow across the valve.

Embodiment 93. The apparatus of any one of Embodiments 89-92, wherein the valve comprises an aperture in the second external layer.

Embodiment 94. The apparatus of Embodiment 93, wherein the aperture provides access to a deflectable portion of the elastomer layer, the deflectable portion comprising a valve sealing rib extending from the elastomer layer toward the first external layer.

Embodiment 95. The apparatus of Embodiment 94, wherein the valve sealing rib contacts the first external layer when the valve is in the closed position and is separated from the first external layer when the valve is in the open position.

Embodiment 96. The apparatus of Embodiment 94 or 95, further comprising a plunger in contact with the deflectable portion of the valve, the plunger being configured in size and shape to be passable into the aperture to deflect the deflectable portion and move the valve toward the closed position.

Embodiment 97. The apparatus of any one of Embodiments 94-96, wherein the valve further comprises a berm formed in the first external layer and extending toward the aperture, optionally wherein the berm contacts the valve sealing rib when the valve is in the closed position.

Embodiment 98. The apparatus of any one of Embodiments 94-98, wherein the deflectable portion extends out of and beyond the aperture when the valve is fully moved to the open position.

Embodiment 99. The apparatus of any one of Embodiments 89-98, wherein the second external layer comprises a second series of channels disposed on a first side of the second external layer, the first side of the second external layer facing the first side of the first external layer.

Embodiment 100. The apparatus of Embodiment 99, wherein the arrangement of sealing ribs comprises a first set of sealing ribs that extend toward the first external layer and a second set of sealing ribs that extend toward the second external layer.

Embodiment 101. The apparatus of any one of Embodiments 89-100, wherein the arrangement of sealing ribs is disposed so as to follow a contour of the series of channels.

Embodiment 102. The apparatus of Embodiment 101, wherein each channel comprises a nadir and forms a surface that rises from the nadir to inflection points disposed on opposite sides of the nadir, and optionally wherein the sealing ribs include an apex, the sealing ribs being arranged such that the apex is disposed at the inflection points of the channels or beyond the inflection points relative to the respective channel nadir.

Embodiment 103. A method for controlling movement of fluid comprises: providing the apparatus as in any one of Embodiments 89-102 to a system for automated purification of a target nucleic acid or target protein; causing one or more plungers to open a valve within the apparatus, the open valve allowing fluid communication between an upstream and downstream section of the series of channels; and causing a pump to move fluid from the upstream section to the downstream section.

Embodiment 104. The method of Embodiment 103, further comprising one or more of: the arrangement of sealing ribs is compressed to withstand at least 30 psi, preferably at least 60 psi, of fluid pressure before leaking; the apparatus is configured to withstand at least 500 lbf, preferably up to 15,000 lbf, applied across an entire length of the arrangement of sealing ribs; or when the elastomer layer is compressed between the first and second external layers, the sealing ribs are compressed at least 20%, preferably at least 30%.

Embodiment 105. A biological sample cartridge comprising at least two of: the apparatus of any one of Embodiments 1-32; the apparatus of any one of Embodiments 47-62; the control system of any one of Embodiments 71-74; the system of any one of Embodiments 75-83; and the apparatus of any one of Embodiments 89-102.

Embodiment 106. An apparatus for automated purification of a target protein from a biological sample comprising: an input reservoir for receiving the biological sample; a first bioprocessing assembly in fluid communication with the input reservoir and a lysis buffer reservoir, the first bioprocessing assembly configured to generate a lysate comprising a target protein; a second bioprocessing assembly in fluid communication with the first bioprocessing assembly and a first elution buffer reservoir, the second bioprocessing assembly including a protein-binding support configured to retain the target protein; and a receptacle in fluid communication with the second bioprocessing assembly, the receptacle configured to receive an output container for receiving the target protein.

Embodiment 107. The apparatus of Embodiment 106, wherein the apparatus comprises a consumable cartridge.

Embodiment 108. The apparatus of Embodiment 106 or 107, wherein the first bioprocessing assembly comprises a clarification filter.

Embodiment 109. The apparatus of Embodiment 108, wherein the clarification filter is in fluid communication with the input reservoir and the lysis buffer reservoir, the clarification filter being configured to separate a target-protein-containing portion of the biological sample from a first waste portion of the biological sample.

Embodiment 110. The apparatus of any one of Embodiments 106-109, wherein the first bioprocessing assembly comprises a cell capture or concentration filter, optionally wherein the cell capture or concentration filter is disposed upstream of a clarification filter.

Embodiment 111. The apparatus of Embodiment 110, wherein the cell capture or concentration filter is in fluid communication with the input reservoir and the lysis buffer reservoir, the cell capture or concentration filter being configured to separate a target-protein-containing portion of the biological sample from a first waste portion of the biological sample.

Embodiment 112. The apparatus of any one of Embodiments 106-111, further comprising one or more additional bioprocessing chambers having reagents for protein purification.

Embodiment 113. The apparatus of any one of Embodiments 106-112, further comprising one or more filters within the apparatus, wherein the one or more filters comprises a hollow fiber filter.

Embodiment 114. A method comprising automatedly isolating or purifying a target protein from the cellular lysate using an apparatus as in any one of Embodiments 106-113.

Embodiment 115. The method of Embodiment 114, wherein the target protein is isolated by one or more of a cell lysis step, a column chromatography, an affinity chromatography, a gel filtration chromatography, an ion exchange chromatography, a fast protein liquid chromatography, or a combination thereof.

Embodiment 116. The method of Embodiment 114 or 115, wherein the sample comprises a biological sample, tissue, biopsy, cell culture, cell, cell suspension, urine, saliva, cerebrospinal fluid, blood, serum, plasma, an aqueous solution of fecal matter, other bodily fluids or exudates, eukaryotic cells selected from the group consisting of rodent, insect, primate, and human cells, prokaryotic cells or cell suspensions comprising prokaryotic cells.

Embodiment 117. The method of any one of Embodiments 114-116, wherein the biological sample is a cell-line or tissue comprising a plurality of cells, the target-protein-containing portion comprises a protein in the cell-line or tissue and the first waste portion comprises lysed cells and optionally culture media.

Embodiment 118. A biological sample cartridge comprising at least two of: the apparatus of any one of embodiments 106-117; the apparatus of any one of Embodiments 47-62; the control system of any one of Embodiments 71-74; the system of any one of Embodiments 75-83; and the apparatus of any one of Embodiments 89-102.

What is claimed is:

1. An instrument for automated purification of a target biomolecule from a biological sample, comprising:
    a purification cartridge comprising an apparatus that includes:
        an input reservoir for receiving the biological sample;
        a first bioprocessing assembly in fluid communication with the input reservoir and a lysis buffer reservoir, the first bioprocessing assembly configured to generate a lysate comprising the target biomolecule;
        a second bioprocessing assembly in fluid communication with the first bioprocessing assembly and a first elution buffer reservoir, the second bioprocessing assembly including a target-biomolecule-binding filter configured to retain the target biomolecule; and
        a receptacle in fluid communication with the second bioprocessing assembly, the receptacle configured to receive an output container for receiving the target biomolecule from the second bioprocessing assembly,
    the purification cartridge further comprising:
        a first external layer comprising a first side and a second side, and
        a second external layer disposed opposite the first side of the first external layer;
    a casing having an internal compartment configured in size and shape for receiving the purification cartridge;
    wherein the internal compartment comprises a position sensor for determining that the purification cartridge has been fully inserted within the internal compartment;
    optionally, a selectively closable access door providing access to the internal compartment;
    a pump assembly disposed within the internal compartment and configured to provide pumping action through peristaltic motion; and
    a clamp mechanism disposed within the internal compartment and configured to move between an open position in which the internal compartment is accessible and a closed position in which the clamp mechanism is clamped against an inserted purification cartridge to enable processing of the biological sample, wherein when in the closed position, the clamp mechanism operates to fluidically seal the purification cartridge by exerting the first external layer and the second external layer towards one another.

2. The instrument of claim 1, further comprising a user interface for displaying instrument information and for receiving user input, the user interface configured to receive user input related to one or more of a volume of biological sample, a selected purification protocol, operating instructions for the selectively closable door, a desired concentration of the target biomolecule, or a final volume of eluent comprising the target biomolecule.

3. The instrument of claim 1, further comprising one or more access door sensors configured to determine whether the access door is in an open or closed position, wherein the one or more access door sensors optionally comprise one or more Hall effect sensors and one or more corresponding magnets.

4. The instrument of claim 1, wherein the pump assembly comprises a camshaft coupled to a motor via a power transmission assembly, a plurality of cam elements being attached to the camshaft and extending transversely therefrom toward the purification cartridge when inserted, the cam elements optionally including beveled tips for engaging the purification cartridge when inserted.

5. The instrument of claim 1, wherein the biological sample is a bacterial culture, a cell culture, a prokaryotic cell culture, a eukaryotic cell culture, a clinical sample, an environmental sample, a food sample, or a beverage sample.

6. The instrument of claim 1, wherein the apparatus further comprises an optical density detector window disposed between the input reservoir and the first bioprocessing assembly, the optical density detector window being configured to allow detection of an optical density of the biological sample.

7. The instrument of claim 1, wherein the first bioprocessing assembly comprises a clarification filter.

8. The instrument of claim 7, wherein the first bioprocessing assembly comprises a cell capture filter, wherein the cell capture filter is disposed upstream of the clarification filter.

9. The instrument of claim 1, wherein the target-biomolecule-binding filter of the second bioprocessing assembly comprises a silica-based filter or a column of beads having affinity for the target biomolecule.

10. The instrument of claim 9, wherein the second bioprocessing assembly further comprises a purification reagent reservoir in fluid communication with the target-biomolecule-binding filter or a protein binding filter.

11. The instrument of claim 1, wherein the second bioprocessing assembly comprises a mixing chamber disposed between the first bioprocessing assembly and the target-biomolecule-binding filter.

12. The instrument of claim 11, wherein the mixing chamber is in fluid communication with an endotoxin removal buffer reservoir.

13. The instrument of claim 1, wherein the output container is selectively detachable from the apparatus.

14. The instrument of claim 1, wherein the input reservoir is sized and shaped to receive up to 2 L of the biological sample.

15. The instrument of claim 1, wherein the target biomolecule is a target nucleic acid, wherein:
- the first bioprocessing assembly is configured to receive the biological sample, the first bioprocessing assembly comprising a waste-separation filter and a plurality of reservoirs fluidically coupled to the waste-separation filter;
- the second bioprocessing assembly comprising an anion exchange membrane, a washing solution reservoir fluidically coupled to the anion exchange membrane and the first elution buffer reservoir being fluidically coupled to the anion exchange membrane; and
- the purification cartridge comprising a third bioprocessing assembly comprising a precipitation filter and a second elution buffer reservoir fluidically coupled to the precipitation filter,
- wherein the first bioprocessing assembly additionally comprises a cell capture filter, and wherein a first reservoir of the plurality of reservoirs comprises a resuspension buffer reservoir, and wherein the input reservoir is fluidically coupled to a first side of the cell capture filter and the resuspension buffer reservoir is fluidically coupled to a second side of the cell capture filter.

16. The instrument of claim 1, wherein the instrument includes a selectively closable access door providing access to the internal compartment and wherein when in the closed position, the clamp mechanism operates to fluidically seal the purification cartridge and further comprising a controller, wherein the controller routes power to the clamp mechanism only upon determining that the access door is closed.

17. The instrument of claim 1, wherein the input reservoir is sized and shaped to receive between about 5 mL and 5 L of the biological sample.

18. The instrument of claim 1, wherein the input reservoir is sized and shaped to receive between about 100 mL and 1 L of the biological sample.

* * * * *